United States Patent [19]

Morrow et al.

[11] Patent Number: 6,063,384
[45] Date of Patent: May 16, 2000

[54] ENCAPSIDATED RECOMBINANT VIRAL NUCLEIC ACID AND METHODS OF MAKING AND USING SAME

[75] Inventors: Casey D. Morrow; Donna C. Porter, both of Birmingham; David C. Ansardi, Warrior, all of Ala.

[73] Assignee: The UAB Research Foundation, Birmingham, Ala.

[21] Appl. No.: 08/987,867

[22] Filed: Dec. 9, 1997

Related U.S. Application Data

[60] Division of application No. 08/389,459, Feb. 15, 1995, Pat. No. 5,817,512, which is a continuation-in-part of application No. 08/087,009, Jul. 1, 1993, abandoned.

[51] Int. Cl.$^7$ .......................... C12P 21/02; C12N 15/43; A61K 39/13
[52] U.S. Cl. ................................ 424/199.1; 424/217.1; 424/208.1; 435/69.3; 435/172.1; 435/320.1
[58] Field of Search .............................. 424/199.1, 217.1, 424/208.1; 435/69.3, 172.1, 320.1

[56] References Cited

PUBLICATIONS

Ansardi, D.C. et al. (1994) "Characterization of Poliovirus Replicons Encoding Carcinoembryonic Antigen" *Cancer Research* 54:6359–6364.

Kantor, J. et al. (1992) "Antitumor Activity and Immune Responses Induced by a Recombinant Carcinoembryonic Antigen–Vaccinia Virus Vaccine" *J. Natl. Cancer Institute* 84:1084–1091.

Ansardi, D.C. et al. (1994) "Characterization of Poliovirus Replicons Encoding Carcinoembryonic Antigen" *Cancer Research* 54:6359–6364.

Ansardi, D.C. et al. (1991) "Coinfection with Recombinant Vaccinia Viruses Expressing Poliovirus P1 and P3 Proteins Results in Polyprotein Processing and Formation of Empty Capsid Structures" *J. Virol.* 65(4):2088–2092.

Ansardi, D.C. et al. (1993) "Complementation of a Poliovirus Defective Genome by a Recombinant Vaccinia Virus Which Provides Poliovirus P1 Capsid Precursor in trans" *J. Virol.* 67(6):3684–3690.

Ansardi, D.C. et al. (1993) "Molecular Analysis of Poliovirus Assembly Using Recombinant Vaccinia Viruses to Complement a Poliovirus Genome with a Capsid Gene Deletion" *J. Cell Biochem. Suppl. 17 D*:22, M301.

Choi, W.S. et al. (1991) "Expression of Human Immunodeficiency Virus Type 1 (HIV–1) gag, pol, and env Poliovirus Minireplicons" *J. Virol.* 65(6):2875–2883.

Evans, D.J. et al. (1989) "An Engineered Poliovirus Chimaera Elicits Boradly Reactive HIV–1 Neutralizing Antibodies" *Nature* 339:385–388.

Fox, J.L. (1994) "No Winners Against AIDS" *Bio/Technology* 12:128.

Haynes, B.F. (1993) "Scientific and Social Issues of Human Immunodeficiency Virus Vaccine Development" *Science* 260:1279–1286.

Jenkins, O. et al. (1990) "An Anitgen Chimera of Polivirus Induces Antibodies against Human Papillomavirus Type 16" *J. Virol.* 64(3):1201–1206.

Knuth, A. et al. (1991) "Cellular and Humoral Immune Responses Against Cancer: Implications for Cancer Vaccines" *Current Opinion in Immunology* 3:659–664.

Ledley, F. (1991) "Clinical Considerations in the Design of Protocols for Somatic Gene Therapy" *Human Gene Therapy* 2:77–83.

McGhee, J.R. and Mestecky, J. (1992) "The Mucosal Immune System in HIV Infection and Prospects for Mucosal Immunity to AIDS" *AIDS Research Reviews*, W.C. Koff et al. (eds.), New York: Marcel Dekker, Inc., 2:Ch. 15, 289–312.

Moldoveanu, Z. et al. (1995) "Immune Responses Induced by Administration of Encapsidated Poliovirus Replicons Which Express H

OTHER PUBLICATIONS

Porter, D.C. et al. (1993) "Encapsidation of Chimeric HIV–1–Poliovirus Minireplicons" *J. Cell Biochem. Suppl. 17 D*:26, M317.

Porter, D.C. et al. (1993) "Encapsidation of Genetically Engineered Poliovirus Minireplicons Which Express Human Immunodeficiency Virus Type 1 Gag and Pol Proteins upon Infection" *J. Virol. 67(7)*:3712–3719.

Porter, D. et al. (1995) "Encapsidation of Poliovirus Replicons Encoding the Complete Human Immunodeficiency Virus Type 1 gag Gene by Using a Complementation System Which Provides the P1 Capsid Protein in trans" *Journal of Virology 69(3)*:1548–1555.

Porter, D.C. et al. (1993) "Expression of Poliovirus P3 Proteins Using a Recombinant Vaccinia Virus Results in Proteolytically Active 3CD Precursor Protein Without Further Processing to $3C^{pro}$ and $3D^{pol}$" *Virus Research 29*:241–254.

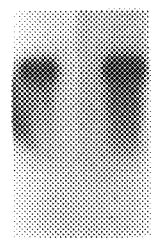
FIG.5
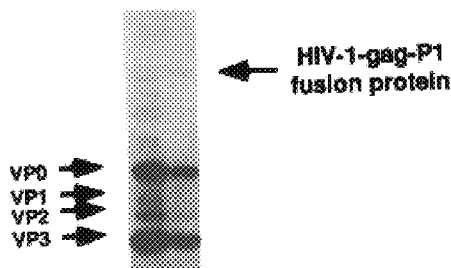
FIG.6
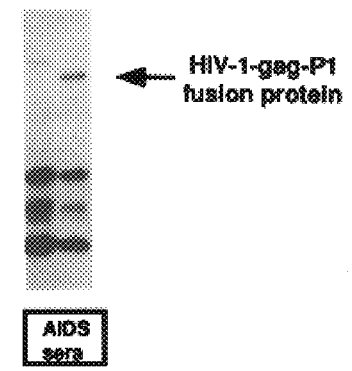
FIG.7A
FIG.7B
FIG.7C pT7-IC:

pT7-IC-Pr55 gag:

pT7-IC-Pr55 gag(VP4/2A):

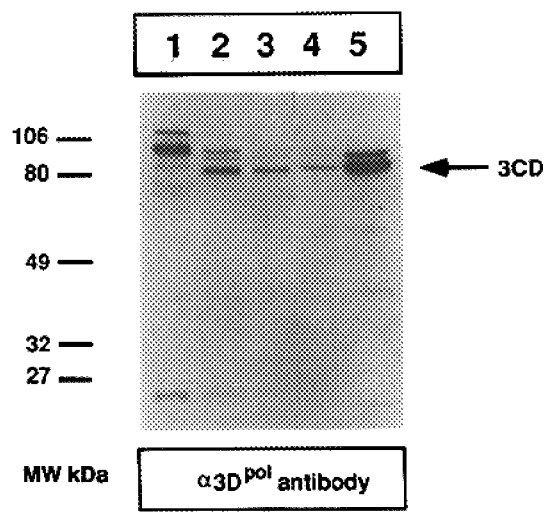 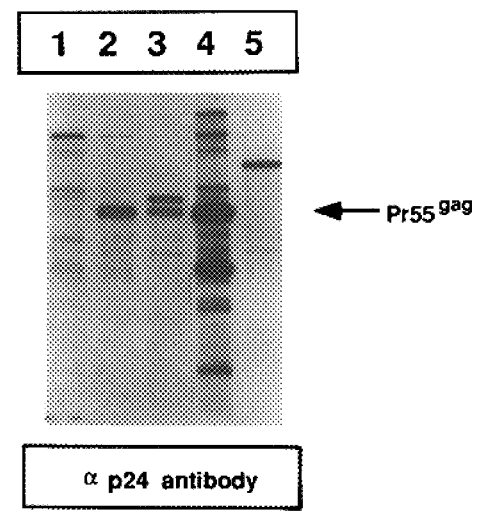
FIG. 18A   FIG. 18B

Phosphorimagery Quantitation of Samples
Analyzed by Northern Blot

| Samples | Values |
|---|---|
| pT7-IC-Pr55 $^{gag}$ | 19,062 |
| pT7-IC-Pr55 $^{gag}$ (VP4/2A) | 18,430 |
| pT7-IC-Gag 1 | 98,800 |

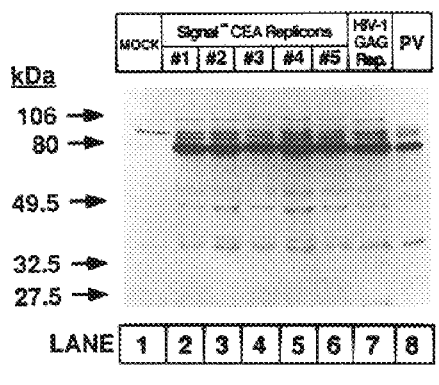 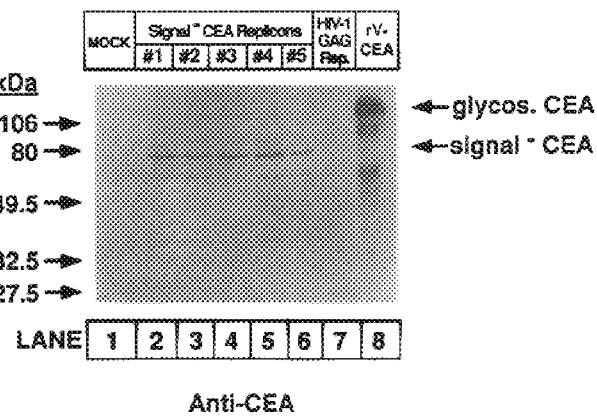
*FIG. 24A*  *FIG. 24B*

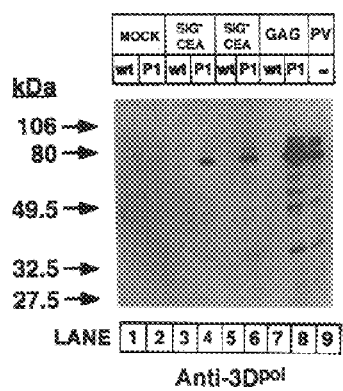 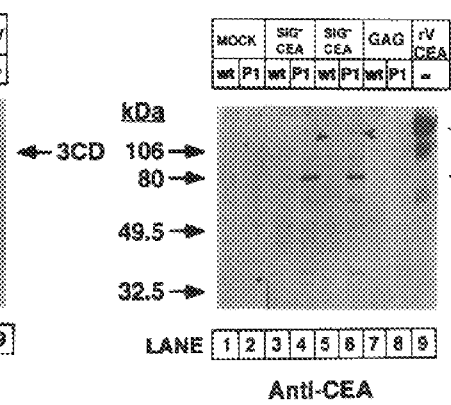 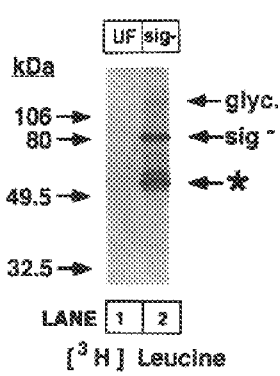
*FIG. 25A*  *FIG. 25B*  *FIG. 25C*

ENCAPSIDATED RECOMBINANT VIRAL NUCLEIC ACID AND METHODS OF MAKING AND USING SAME

RELATED APPLICATIONS

This application is a divisional of U.S. Ser. No. 08/389,459, filed Feb. 15, 1995, now U.S. Pat. No. 5,817,512, which is a-continuation-in-part application of U.S. Ser. No. 08/087,009, filed Jul. 1, 1993, now abandoned, the contents of which are incorporated herein by reference.

GOVERNMENT SUPPORT

The work described herein was supported by Public Health Service contract (Mucosal Immunology Group) AI 15128, Public Health Service grant AI25005 from the National Institutes of Health, and National Cooperative Vaccine Development Grant (NCVDG) 2 UOI AI28147-06.

BACKGROUND OF THE INVENTION

The present invention relates to methods of encapsidating a recombinant viral nucleic acid having a foreign nucleotide sequence substituted for the nucleotide sequence of the virus encoding at least a portion of a protein necessary for encapsidation. More particularly, the invention relates to methods and compositions for generating an immune response in a subject by using such a recombinant virus.

Live or attenuated viruses have long been used to stimulate the immune system in a subject. Poliovirus is an attractive candidate system for delivery of antigens to the mucosal immune system because of several biological features inherent to the virus. First, the pathogenesis of the poliovirus is well-studied and the important features identified. The poliovirus is naturally transmitted by an oral-fecal route and is stable in the harsh conditions of the intestinal tract. Primary replication occurs in the oropharynx and gastro-intestinal tract, with subsequent spread to the lymph nodes. Horstmann, D. M. et al. (1959)*JAMA* 170:1–8. Second, the attenuated strains of poliovirus are safe for humans, and are routinely administered to the general population in the form of the Sabin oral vaccine. The incorporation of foreign genes into the attenuated strains would be an attractive feature that should pose no more of a health risk than that associated with administration of the attenuated vaccines alone. Third, the entire poliovirus has been cloned, the nucleic acid sequence determined, and the viral proteins identified. An infectious cDNA is also available for poliovirus which has allowed further genetic manipulation of the virus. Further, previous studies using the attenuated vaccine strains of poliovirus have demonstrated that a long-lasting systemic and mucosal immunity is generated after administration of the vaccine. Sanders, D. Y. and Cramblett, H. G. (1974)*J. Ped.* 84:406–408; Melnick, J. (1978)*Bull. World Health Organ.* 56:21–38; Racaniello, V. R. and Baltimore, D. (1981)*Science* 214:916–19; Ogra, P. L. (1984)*Rev. Infect. Dis.* 6:S361-S368.

Recent epidemiological data suggest that worldwide more than seventy percent of infections with human immunodeficiency virus (HIV) are acquired by heterosexual intercourse through mucosal surfaces of the genital tract and rectum. Most HIV vaccines developed to date have been designed to preferentially stimulate the systemic humoral immune system and have relied on immunization with purified, whole human immunodeficiency virus type 1 (HIV-1) and HIV-1 proteins (Haynes, B. F. (May 1993) *Science* 260:1279–1286.), or infection with a recombinant virus or microbe which expresses HIV-1 proteins (McGhee, J. R., and Mestecky, J. (1992)*AIDS Res. Rev.* 2:289–312). A general concern with these studies is that the method of presentation of the HIV-1 antigen to the immune system will not stimulate systemic and mucosal tissues to generate effective immunity at mucosal surfaces. Given the fact that the virus most often encounters a mucosal surface during sexual (vaginal or anal) transmission, a vaccine designed to stimulate both the systemic and mucosal immune systems is essential. McGhee, J. R., and Mestecky, J. (1992) *AIDS Res. Rev.* 2:289–312; Forrest, B. D. (1992)*AIDS Research and Human Retroviruses* 15 8:1523–1525.

In 1991, a group of researchers reported the construction and characterization of chimeric HIV-1-poliovirus genomes. Choi, W. S. et al. (June 1991)*J. Virol.* 65(6):2875–2883. Segments of the HIV-1 proviral DNA containing the gag, pol, and env gene were inserted into the poliovirus cDNA so that the translational reading frame was conserved between the HIV-1 and poliovirus genes. The RNAs derived from the in vitro transcription of the genomes, when transfected into cells, replicated and expressed the appropriate HIV-1 protein as a fusion with the poliovirus P1 protein. Choi, W. S. et al. (June 1991)*J Virol.* 65(6):2875–2883. However, since the chimeric HIV-1-poliovirus genomes were constructed by replacing poliovirus capsid genes with the HIV-1 gag, pol, or env genes, the chimeric HIV-1-genomes were not capable of encapsidation after introduction into host cells. Choi, W. S. et al. (June 1991)*J. Virol.* 65(6):2875–2883. Furthermore, attempts to encapsidate the chimeric genome by cotransfection with the poliovirus infectious RNA yielded no evidence of encapsidation. Choi, W. S. et al. (June 1991)*J. Virol.* 65(6):2875–2883.

In 1992, another group of researchers reported the encapsidation of a poliovirus replicon which incorporated the reporter gene, chloramphenicol acetyltransferase (CAT), in place of the region coding for capsid proteins VP4, VP2, and a portion of VP3 in the genome of poliovirus type 3. Percy, N. et al. (Aug. 1992)*J. Virol.* 66(8):5040–5046. Encapsidation of the poliovirus replicon was accomplished by first transfecting host cells with the poliovirus replicon and then infecting the host cells with type 3 poliovirus. Percy, N. et al. (Aug. 1992) *J. Virol.* 66(8):5040, 5044. The formation of the capsid around the poliovirus genome is believed to be the result of interactions between capsid proteins and the poliovirus genome. Therefore, it is likely that the yield of encapsidated viruses obtained by Percy et al. consisted of a mixture of encapsidated poliovirus replicons and encapsidated nucleic acid from the type 3 poliovirus. The encapsidated type 3 poliovirus most likely represents a greater proportion of the encapsidated viruses than does the encapsidated poliovirus replicons. The Percy et al. method of encapsidating a poliovirus replicon is, therefore, an inefficient system for producing encapsidated recombinant poliovirus nucleic acid.

Accordingly, it would be desirable to provide a method of encapsidating a recombinant poliovirus genome which results in a stock of encapsidated viruses substantially composed of the recombinant poliovirus genome. Such a method would enable the efficient production of encapsidated poliovirus nucleic acid for use in compositions for stimulating an immune response to foreign proteins encoded by the recombinant poliovirus genome.

SUMMARY OF THE INVENTION

The present invention pertains to methods of encapsidating a recombinant poliovirus nucleic acid to obtain a yield of encapsidated viruses which substantially comprises encapsidated recombinant poliovirus nucleic acid. The methods of encapsidating a recombinant poliovirus nucleic acid include providing a recombinant poliovirus nucleic acid which lacks the nucleotide sequence encoding at least a portion of a protein necessary for encapsidation and an expression vector lacking an infectious poliovirus genome, the nucleic acid of which encodes at least a portion of one protein necessary for encapsidation; contacting a host cell with the recombinant poliovirus nucleic acid and the expression vector under conditions appropriate for introduction of the recombinant poliovirus nucleic acid and the expression vector into the host cell; and obtaining a yield of encapsidated viruses which substantially comprises an encapsidated recombinant poliovirus nucleic acid. The nucleic acid of the expression vector does not interact with the capsid proteins or portions of capsid proteins which it encodes, thereby allowing encapsidation of the recombinant poliovirus nucleic acid and avoiding encapsidation of the nucleic acid of the expression vector. The invention further pertains to encapsidated recombinant poliovirus nucleic acids produced by the methods of this invention.

In a preferred embodiment, the methods of encapsidating a recombinant poliovirus nucleic acid include providing a recombinant poliovirus nucleic acid in which the VP2 and VP3 genes of the P1 capsid precursor region of the poliovirus genome are replaced by a foreign nucleotide sequence encoding, in an expressible form, a protein or fragment thereof, such as an immunogenic protein or fragment thereof. Examples of immunogenic proteins which can be encoded by the foreign nucleotide sequence include human immunodeficiency virus type 1 proteins and tumor-associated antigens. A host cell, e.g., a mammalian host cell, is then contacted with this recombinant poliovirus nucleic acid and an expression vector lacking an infectious poliovirus genome, such as a vaccinia virus, which encodes the poliovirus P1 capsid precursor protein. Because the expression vector nucleic acid, e.g., vaccinia viral nucleic acid nucleic acid, does not compete with the recombinant poliovirus nucleic acid for the poliovirus capsid proteins, a yield of encapsidated viruses which substantially comprises encapsidated poliovirus nucleic acid is obtained. Further, the resulting encapsidated recombinant poliovirus nucleic acid is able to direct expression of the foreign protein or fragment thereof.

In another preferred embodiment, the methods of encapsidating a recombinant poliovirus nucleic acid include providing a recombinant poliovirus nucleic acid in which the entire P1 capsid precursor region of the poliovirus genome is replaced by a foreign nucleotide sequence encoding, in an expressible form, a protein or fragment thereof, such as an immunogenic protein or fragment thereof. A host cell, e.g., a mammalian host cell, is then contacted with this recombinant poliovirus nucleic acid and an expression vector lacking an infectious poliovirus genome, such as a vaccinia virus, which encodes the poliovirus P1 capsid precursor protein to thereby generate a yield of encapsidated viruses which substantially comprises encapsidated recombinant poliovirus nucleic acid. By these methods of encapsidating recombinant poliovirus nucleic acids, the upper size limit of the foreign nucleotide which can be inserted into the poliovirus nucleic acid is increased, thereby allowing expression of entire proteins, as well as fragments or portions of proteins. The present invention also pertains to encapsidated recombinant poliovirus nucleic acids which lack the entire P1 capsid precursor region.

The present invention further pertains to compositions for stimulating an immune response to an immunogenic protein or fragment thereof and a method for stimulating the immune response by administering the compositions to a subject. The compositions typically contain an encapsidated recombinant poliovirus nucleic acid, in a physiologically acceptable carrier, which encodes an immunogenic protein or fragment thereof and directs expression of the immunogenic protein, or fragment thereof. The compositions are administered to a subject in an amount effective to stimulate an immune response to the immunogenic protein or fragment thereof, e.g., in an amount effective to stimulate the production of antibodies against the immunogenic protein or fragment thereof in the subject.

The invention still further pertains to methods for generating cells that produce a foreign protein or fragment thereof. These methods include contacting host cells with an encapsidated recombinant poliovirus nucleic acid having a foreign nucleotide sequence substituted for the nucleotide sequence which encodes at least a portion of a protein necessary for encapsidating the recombinant poliovirus nucleic acid and an expression vector lacking an infectious poliovirus genome but which encodes and directs expression of at least a portion of a protein necessary for encapsidation of the recombinant poliovirus nucleic acid and directs expression of at least a portion of a protein necessary for encapsidating the recombinant poliovirus nucleic acid and maintaining the cultured host cells under conditions appropriate for introduction of the recombinant poliovirus nucleic acid and the expression vector into the host cells, thereby generating modified cells which produce a foreign protein or fragment thereof. Such modified cells can be reintroduced into the subject from which they were obtained to stimulate an immune response in the subject to the foreign protein or fragment thereof produced by the cells.

BRIEF DESCRIPTION OF THE DRAWINGS

FIG. 5 shows a Northern blot analysis of RNA isolated from a stock of encapsidated recombinant poliovirus nucleic acid.

FIG. 6 shows an SDS-polyacrylamide gel on which the neutralization of the poliovirus nucleic acid encapsidated by VV-P1 with anti-poliovirus antibodies was analyzed.

FIGS. 7A, 7B, and 7C show SDS-polyacrylamide gels on which poliovirus- and HIV-1-specific protein expression from cells infected with a stock of poliovirus nucleic acid encapsidated by type 1 Sabin poliovirus was analyzed.

Figure 1:
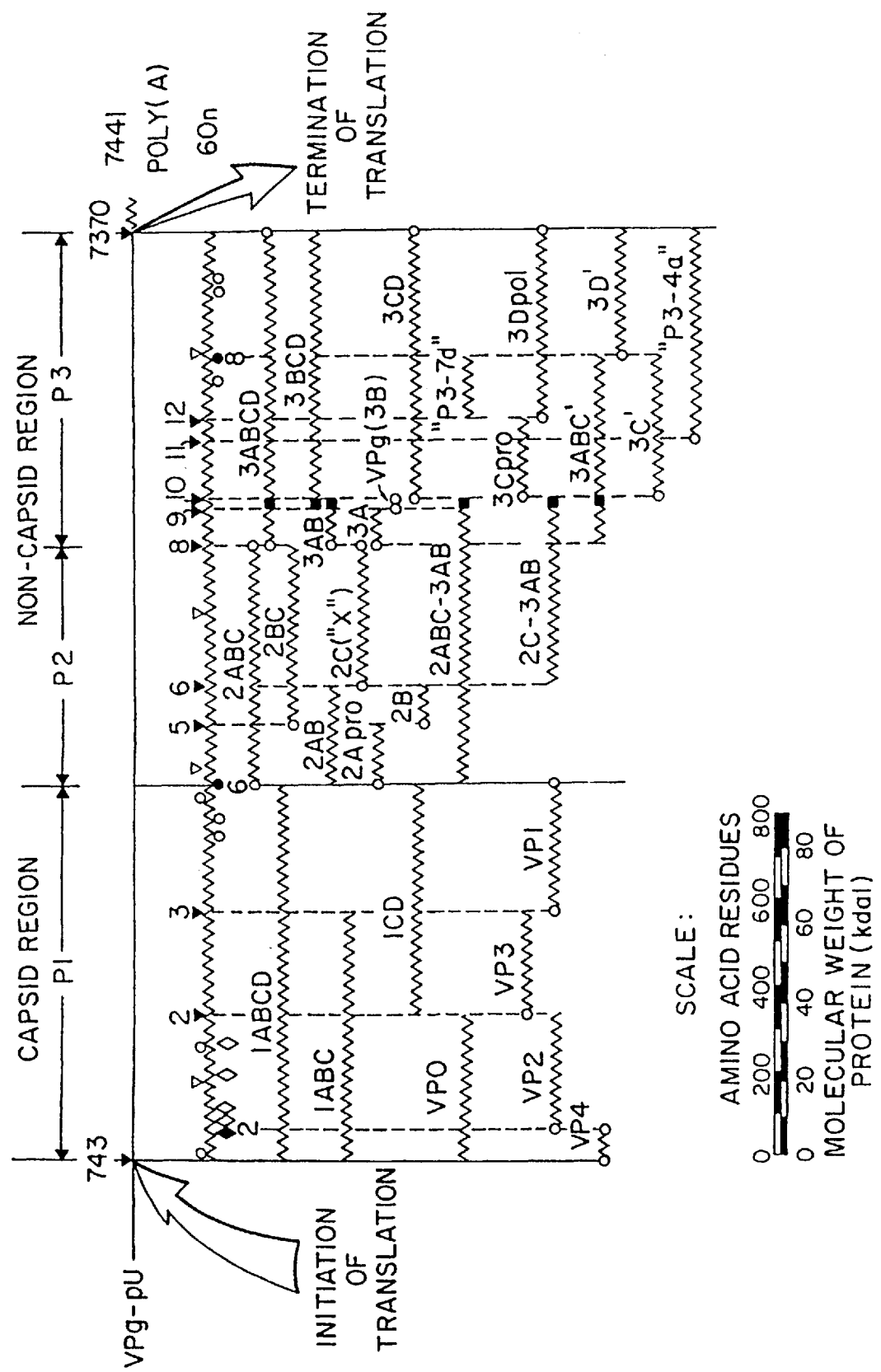
FIG. 1 shows a schematic of the translation and proteolytic processing of the poliovirus polyprotein.

FIGS. 11A, 11B, and 11C show anti-poliovirus IgA in feces from mice after intragastric, intrarectal, and intramuscular administration of an encapsidated recombinant poliovirus nucleic acid encoding and expressing at least a portion of the gag protein of human immunodeficiency virus type 1.

FIGS. 12A, 12B, and 12C show anti-HIV-1-Gag IgG in serum from mice after intragastric, intrarectal, and intramuscular administration of an encapsidated recombinant poliovirus nucleic acid encoding and expressing at least a portion of the gag protein of human immunodeficiency virus type 1.

FIGS. 13A, 13B, and 13C show anti-HIV-1-Gag IgA in saliva from mice after intragastric, intrarectal, and intramuscular administration of an encapsidated recombinant poliovirus nucleic acid encoding and expressing at least a portion of the gag protein of human immunodeficiency virus type 1.

FIGS. 14A and 14B show anti-HIV-1-Gag IgA in vaginal lavages from mice after intragastric, intrarectal, and intramuscular administration of an encapsidated recombinant poliovirus nucleic acid encoding and expressing at least a portion of the gag protein of human immunodeficiency virus type 1.

FIGS. 15A, 15B, and 15C show anti-HIV-1-Gag IgA in feces from mice after intragastric, intrarectal, and intramuscular administration of an encapsidated recombinant poliovirus nucleic acid encoding and expressing at least a portion of the gag protein of human immunodeficiency virus type 1.

FIG. 16 shows anti-poliovirus IgG from serum of a Pigtail macaque after intrarectal administration of an encapsidated recombinant poliovirus nucleic acid encoding and expressing at least a portion of the gag protein of human immunodeficiency virus type 1.

FIGS. 17A, 17B, and 17C show recombinant poliovirus nucleic acids which contain the complete gag gene of HIV-1.

FIGS. 18A and 18B show an analysis of protein expression from cells transfected with RNA derived from recombinant poliovirus nucleic acid containing the gag gene of HIV-1.

FIGS. 19A and 19B show quantitation of recombinant poliovirus RNA from transfected cells by Northern blot.

FIG. 20 shows an analysis of poliovirus and HIV-1 specific protein expression from cells infected with recombinant poliovirus nucleic acid encapsidated in trails using VV-P1.

FIGS. 21A and 21B show an analysis of protein expression from cells infected with normalized amounts of encapsidated recombinant poliovirus nucleic acid stocks and material derived from serial passage of equivalent amounts of encapsidated recombinant poliovirus nucleic acid virus stocks with VV-P1.

FIG. 22 shows an analysis of protein expression from cells infected with material derived from the serial passage of encapsidated recombinant poliovirus nucleic acid with wild-type poliovirus.

FIGS. 23A, 23B, and 23C show construction of recombinant poliovirus nucleic acid containing the gene for carcinoembryonic antigen.

FIGS. 24A and 24B show expression, in transfected cells, of carcinoembryonic protein encoded by recombinant poliovirus nucleic acid containing the gene for carcinoembryonic antigen.

FIGS. 25A, 25B, and 25C show an analysis of poliovirus and carcinoembryonic expression from cells infected with recombinant poliovirus nucleic acid containing the gene for carcinoembryonic antigen; the recombinant poliovirus nucleic acid was encapsidated and serially passaged with capsid proteins provided by VV-P1.

FIGS. 26A and 26B show antibody response to encapsidated recombinant poliovirus nucleic acid expressing carcinoembryonic antigen.

DETAILED DESCRIPTION OF THE INVENTION

The genome of poliovirus has been cloned and the nucleic acid sequence determined. The genomic RNA molecule is 7433 nucleotides long, polyadenylated at the 3' end and has a small covalently attached viral protein (VPg) at the 5' terminus. Kitamura, N. et al.(1981) *Nature* (London) 291:547–553; Racaniello, V. R. and Baltimore, D. (1981) *Proc. Natl. Acad. Sci.* USA 78:4887–4891. Expression of the poliovirus genome occurs via the translation of a single protein (polyprotein) which is subsequently processed by virus encoded proteases (2A and 3C) to give the mature structural (capsid) and nonstructural proteins. Kitamura, N. et al.(1981)*Nature (London)* 291:547–553; Koch, F. and Koch, G. (1985) The Molecular Biology of Poliovirus (Springer-Verlag, Vienna). Poliovirus replication is catalyzed by the virus-encoded RNA-dependent RNA polymerase ($3D^{pol}$), which copies the genomic RNA to give a complementary RNA molecule, which then serves as a template for further RNA production. Koch, F. and Koch, G. (1985) The Molecular Biology of the Poliovirus (Springer-Verlag, Vienna); Kuhn, R. J. and Wimmer, E. (1987) in D. J. Rowlands et al. (ed.) Molecular Biology of Positive Strand RNA viruses (Academic Press, Ltd., London).

The translation and proteolytic processing of the poliovirus polyprotein is depicted in FIG. 1 which is a figure from Nicklin, M. J. H. et al. (1986)*Bio/Technology* 4:33–42. With 25 reference to the schematic in FIG. 1, the coding region and translation product of poliovirus RNA is divided into three primary regions (P1, P2, and P3), indicated at the top of the figure. The RNA is represented by a solid line and relevant nucleotide numbers are indicated by arrows. Protein products are indicated by waved lines. Cleavage sites are mapped onto the polyprotein (top waved line) as filled symbols; open symbols represent the corresponding sites which are not cleaved. (▽,▽) are QG pairs, (0,0) are YG pairs, and (◇,◇) are NS pairs. Cleaved sites are numbered according to the occurrence of that amino-acid pair in the translated sequence. Where the amino acid sequence of a terminus of a polypeptide has been determined directly, an open circle has been added to the relevant terminus.

The mature poliovirus proteins arise by a proteolytic cascade which occurs predominantly at Q-G amino acid pairs. Kitamura, N. et al. (1981)*Nature (London)* 291:547–553; Semler, B. L. et al. (1981)*Proc. Natl. Acad. Sci.* USA 78:3763–3468; Semler, B. L. et al. (1981)*Virology* 114:589–594; Palmenberg, A. C. (1990)*Ann. Rev. Microbiol.* 44:603–623. A poliovirus-specific protein, $3C^{pro}$, is the protease responsible for the majority of the protease cleavages. Hanecak, R. et al. (1982)*Proc. Natl. Acad. Sci.* USA:79–3973–3977; Hanecak, R. et al. (1984)*Cell* 37:1063–1073; Nicklin, M. J. H. et al. (1986) *Bio/*

*Technology* 4:33–42; Harris, K. L et al. (1990)*Seminars in Virol.* 1:323–333. A second viral protease, 2A$^{pro}$, autocatalytically cleaves from the viral polyprotein to release P1, the capsid precursor. Toyoda, H. et al. (1986)*Cell* 45:761–770. A second, minor cleavage by 2A$^{pro}$ occurs within the 3D$^{pol}$ to give 3C' and 3D'. Lee, Y. F. and Wimmer, E. (1988) *Virology* 166:404–414. Another role of the 2A$^{pro}$ is the shut off of host cell protein synthesis by inducing the cleavage of a cellular protein required for cap-dependent translation. Bernstein, H. D. et al. (1985)*Mol. Cell Biol.* 5:2913–2923; Krausslich, H. G. et al. (1987)*J. Virol.* 61:2711–2718; Lloyd, R. E. et al. (1988)*J. Virol.* 62:4216–4223.

Previous studies have established that the entire poliovirus genome is not required for RNA replication. Hagino-Yamagishi, K., and Nomoto, A. (1989)*J. Virol.* 63:5386–5392. Naturally occurring defective interfering particles (DIs) of poliovirus have the capacity for replication. Cole, C. N. (1975)*Prog. Med. Virol.* 20:180–207; Kuge, S. et al. (1986)*J. Mol. Biol.* 192:473–487. The common feature of the poliovirus DI genome is a partial deletion of the capsid (P1) region that still maintains the translational reading frame of the single polyprotein through which expression of the entire poliovirus genome occurs. In recent years, the availability of infectious cDNA clones of the poliovirus genome has facilitated further study to define the regions required for RNA replication. Racaniello, V. and Baltimore, D. (1981)*Science* 214:916–919. Specifically, the deletion of 1,782 nucleotides of P1, corresponding to nucleotides 1174 to 2956, resulted in an RNA which can replicate upon transfection into tissue culture cells. Hagino-Yamagishi, K. and Nomoto, A. (1989)*J. Virol.* 63:5386–5392.

Early studies identified three poliovirus types based on reactivity to antibodies. Koch, F. and Koch, G. The Molecular Biology of Poliovirus (Springer-Verlag, Vienna 1985). These three serological types, designated as type I, type II, and type III, have been further distinguished as having numerous nucleotide differences in both the non-coding regions and the protein coding regions. All three strains are suitable for use in the present invention. In addition, there are also available attenuated versions of all three strains of poliovirus. These include the Sabin type I, Sabin type II, and Sabin type III attenuated strains of poliovirus that are routinely given to the population in the form of an oral vaccine. These strains can also be used in the present invention.

The recombinant poliovirus nucleic acid of the present invention lacks the nucleotide sequence encoding at least a portion or a protein necessary for encapsidation of the recombinant poliovirus nucleic acid. The nucleotide sequence that is absent from the recombinant poliovirus nucleic acid can be any sequence at least a portion of which encodes at least a portion of a protein necessary for encapsidation, and the lack of which does not interfere with the ability of the poliovirus nucleic acid to replicate or to translate, in the correct reading frame, the single polyprotein through which expression of the entire poliovirus genome occurs. The recombinant poliovirus nucleic acid can be deoxyribonucleic acid (DNA) or ribonucleic acid (RNA). As the poliovirus genome is comprised of RNA which replicates in the absence of a DNA intermediate, it is typically introduced into a cell in the form of RNA. This avoids integration of the poliovirus genome into that of the host cell.

Proteins or portions of proteins necessary for encapsidation of a recombinant poliovirus nucleic acid include, for example, proteins or portions of proteins that are part of the capsid structure. Examples of such proteins are the proteins encoded by the VP 1, VP2, VP3, and VP4 genes of the poliovirus P1 capsid precursor region, the Vpg protein, and those proteins that are necessary for proper processing of structural proteins of the capsid structure, such as the proteases responsible for cleaving the viral polyprotein.

The nucleotide sequence lacking from the recombinant poliovirus nucleic acid can be the result of a deletion of poliovirus nucleotide sequences or a deletion of poliovirus nucleotide sequences and insertion of a foreign nucleotide sequence in the place of the deleted sequences. Generally, the nucleotide sequence lacking from the recombinant poliovirus nucleic acid is the P1 region of the poliovirus genome or a portion thereof, which is replaced by a foreign gene. As used herein, the phrase "which lacks the entire P1 capsid precursor region" when used to refer to a recombinant poliovirus nucleic acid is intended to include recombinant poliovirus nucleic acids in which the nucleotide sequence encoding the P1 capsid precursor protein has been deleted or altered such that the proteins which are normally encoded by this nucleotide sequence are not expressed or are expressed in a form which does not function normally. The proteins that are normally encoded by the P1 capsid precursor region of the poliovirus genome include the proteins encoded by the VP1, VP2, VP3, and VP4 genes. A recombinant poliovirus nucleic acid which lacks the entire P1 capsid precursor region, therefore, either does not include a nucleotide sequence which encodes the proteins encoded by the VP1, VP2, VP3, and VP4 genes or includes a nucleotide sequence which encodes, in unexpressible form or in expressible but not functional form, the proteins encoded by the VP1, VP2, VP3, and VP4 genes. In the present invention, it is specifically contemplated that recombinant poliovirus nucleic acids which lack the entire P1 capsid precursor region can include nucleotide sequences which encode amino acids which are included in the proteins encoded by the VP1, VP2, VP3, and VP4 genes so long as the nucleotide sequence encoding these amino acids of the capsid proteins do not encode the capsid proteins in expressible form or if in expressible form, not functional form. For example, in one embodiment of the invention, the entire P1 capsid precursor region of the poliovirus genome, with the exception of a nucleotide sequence which encodes the first two amino acids (i.e., Met-Gly) of the poliovirus P1 capsid precursor protein, is deleted and replaced with a foreign nucleotide sequence. It is also specifically contemplated that additional nucleotide sequences from the poliovirus genome, e.g., nucleotide sequences which encode amino acid sequences which provide cleavage sites for poliovirus enzymes, e.g., 2A protease, or nucleotide sequences which encode other proteins required for proper processing of a protein encoded by the poliovirus nucleic acid, can be included in recombinant poliovirus nucleic acids which lack the entire P1 capsid precursor region.

Additional nucleotide sequences which encode amino acids which are used as spacers within the poliovirus polyprotein to provide an amino acid sequence of the proper length and of the proper sequence for processing of the poliovirus polyprotein can also be included in recombinant poliovirus nucleic acids which lack the entire P1 capsid precursor region.

The foreign nucleotide sequence (or gene) which is substituted for a poliovirus nucleotide sequence preferably is one that encodes, in an expressible form, a foreign protein or fragment thereof. For example, foreign genes that can be inserted into the deleted region of the poliovirus nucleic acid can be those that encode immunogenic proteins. Such immunogenic proteins include, for example, tumor-associated antigens, e.g., human tumor-associated antigens, such as carcinoembryonic antigen (CEA), the ganglioside antigens GM2, GD2, and GD3 from melanoma cells, the antigen Jen CRG from colorectal and lung cancer cells, synthetic peptides of immunoglobulin epitope from B cell malignancies, antigens which are products of oncogenes such as erb, neu, and sis, or any other tumor-associated antigen, antigens obtained from various pathogens, such as hepatitis B surface antigen, influenza virus hemaglutinin and neuraminidase, human immunodeficiency viral proteins, such as gag, pol, and env, respiratory syncycial virus G protein, and the VP4 and VP1 proteins of rotavirus, bacterial antigens such as fragments of tetanus toxin, diphtheria toxin, and cholera toxin, mycobactcrium tuberculosis protein antigen B, and urease protein from *Heliobactor pylori*. In addition, portions of the foreign genes which encode immunogenic proteins can be inserted into the deleted region of the poliovirus nucleic acid. These genes can encode linear polypeptides consisting of B and T cell epitopes. As these are the epitopes with which B and T cells interact, the polypeptides stimulate an immune response. It is also possible to insert chimeric foreign genes into the deleted region of the poliovirus nucleic acid which encode fusion proteins or peptides consisting of both B cell and T cell epitopes. Similarly, any foreign nucleotide sequence encoding an antigen from an infectious agent can be inserted into the deleted region of the poliovirus nucleic acid.

The foreign gene inserted into the deleted region of the poliovirus nucleic acid can also encode, in an expressible form, immunological response modifiers such as interleukins (e.g. interleukin-1, interleukin-2, interleukin-6, etc.), tumor necrosis factor (e.g. tumor necrosis factor-α, tumor necrosis factor-β), or additional cytokines (granulocyte-monocyte colony stimulating factor, interferon-γ). As an expression system for lymphokines or cytokines, the encapsidated poliovirus nucleic acid encoding the lymphokine or cytokine provides for limited expression (by the length of time it takes for the replication of the genome) and can be locally administered to reduce toxic side effects from systemic administration. In addition, genes encoding antisense nucleic acid, such as antisense RNA, or genes encoding ribozymes (RNA molecules with endonuclease or polymerase activities) can be inserted into the deleted region of the poliovirus nucleic acid. The antisense RNA or ribozymes can be used to modulate gene expression or act as anti-viral agents. Genes encoding herpes simplex thymidine kinase, which can be used for tumor therapy, SV40 T antigen, which can be used for cell immortalization, and protein products from herpes simplex virus, e.g., ICP-27, or adeno-associated virus, e.g., Rep, which can be used to complement defective viral genomes can be inserted into the deleted region of the poliovirus nucleic acid.

Foreign genes encoding, in an expressible form, cell surface proteins, secretory proteins, or proteins necessary for proper cellular function which supplement a nonexistent, deficient, or nonfunctional cellular supply of the protein can also be inserted into the deleted region of the poliovirus nucleic acid. The nucleic acid of genes encoding secretory proteins comprises a structural gene encoding the desired protein in a form suitable for processing and secretion by the target cell. For example, the gene can be one that encodes appropriate signal sequences which provide for cellular secretion of the product. The signal sequence can be the natural sequence of the protein or exogenous sequences. In some cases, however, the signal sequence can interfere with the production of the desired protein. In such cases, the nucleotide sequence which encodes the signal sequence of the protein can be removed. See Example 7, below. The structural gene is linked to appropriate genetic regulatory elements required for expression of the gene product by the target cell. These include a promoter and optionally an enhancer element along with the regulatory elements necessary for expression of the gene and secretion of the gene encoded product.

In one embodiment, the foreign genes that are substituted for the capsid genes of the P1 capsid precursor region of the poliovirus genome are the gag (SEQ ID NO: 3; the sequence of the corresponding gag protein is represented by SEQ ID NO: 4), pol (SEQ ID NO: 5; the sequence of the corresponding pol protein is represented by SEQ ID NO: 6), or env (SEQ ID NO: 7; the sequence of the corresponding env protein is represented by SEQ ID NO: 8) genes, or portions thereof, of the human immunodeficiency virus type 1 (HIV-1). See Example 5, below. Portions of these genes are typically inserted in the poliovirus between nucleotides 1174 and 2956. The entire genes are typically inserted in the poliovirus between nucleotides 743 and 3359. The translational reading frame is thus conserved between the HIV-1 genes and the poliovirus genes. The chimeric HIV-1-poliovirus RNA genomes replicate and express the appropriate HIV-1-P1 fusion proteins upon transfection into tissue culture. Choi, W. S. et al. (June 1991)*J. Virol.* 65(6):2875–2883. In another embodiment, foreign genes encoding tumor-associated antigens or portions thereof, such as carcinoembryonic antigen or portions thereof can be substituted for the capsid genes of the P1 capsid precursor region of the poliovirus genome. See Example 7, below.

Deletion or replacement of the P1 capsid region of the poliovirus genome or a portion thereof results in a poliovirus nucleic acid which is incapable of encapsidating itself. Choi, W. S. et al. (June 1991)*J. Virol.* 65(6):2875–2883. Typically, capsid proteins or portions thereof mediate viral entry into cells. Therefore, poliovirus nucleic acid which is not enclosed in a capsid enters cells on which there is a poliovirus receptor less efficiently than encapsidated poliovirus nucleic acid. It is preferred, but not required, therefore, that essential capsid proteins from another source be provided for encapsidation and delivery of the foreign genes to cells. In the method of this invention, essential poliovirus capsid proteins are provided by an expression vector which is introduced into the host cell along with the recombinant poliovirus nucleic acid. The expression vectors can be introduced into the host cell prior to, concurrently with, or subsequent to the introduction of the recombinant poliovirus nucleic acid. In an alternative embodiment, nonencapsidated recombinant poliovirus nucleic acid can be delivered directly to target cells, e.g., by direct injection into, for example, muscle cells (see, for example, Acsadi et al. (1991)*Nature* 332: 815–818; Wolff et al. (1990)*Science* 247:1465–1468), or by electroporation, transfection mediated by calcium phosphate, transfection mediated by DEAE-dextran, liposome-mediated transfection (Nicolau et al. (1987)*Meth. Enz.* 149:157–176; Wang and Huang (1987) *Proc. Natl. Acad. Sci. USA* 84:7851–7855; Brigham et al. (1989)*Am. J Med. Sci.* 298:278; and Gould-Fogerite et al. (1989)*Gene* 84:429–438), or receptor-mediated nucleic acid uptake (see for example Wu, G. and Wu, C. H. (1988)*J. Biol. Chem.* 263:14621; Wilson et al. (1992)*J. Biol. Chem.* 267:963–967; and U.S. Pat. No. 5,166,320), or other methods of delivering naked nucleic acids to target cells, both in vivo and in vitro, known to those of ordinary skill in the art.

In a preferred method of encapsidating the recombinant poliovirus nucleic acid, the expression vector is introduced into the host cell prior to the introduction of the recombinant poliovirus nucleic acid. The introduction of the expression vector into the host cell prior to the introduction of the recombinant poliovirus nucleic acid allows the initial expression of the protein or portion of the protein necessary for encapsidation by the expression vector.

Previous studies have established that the replication and expression of the poliovirus genes in cells results in the shutoff of host cell protein synthesis which is accomplished by the $2A^{pro}$ protein of poliovirus. Thus, in order for efficient encapsidation, the expression vector must express the protein necessary for encapsidation. In order for this to occur, the expression vector is generally introduced into the cell prior to the addition of the recombinant poliovirus nucleic acid.

Expression vectors suitable for use in the present invention include plasmids and viruses, the nucleic acids of which encode at least a portion of a protein necessary for encapsidation of the recombinant poliovirus nucleic acid and direct expression of the nucleotide sequence encoding at least a portion of a protein necessary for encapsidation of the recombinant poliovirus nucleic acid. In addition, the nucleic acid of the expression vectors of the present invention does not substantially associate with poliovirus capsid proteins or portions thereof. Therefore, expression vectors of the present invention, when introduced into a host cell along with the recombinant poliovirus nucleic acid, result in a host cell yield of encapsidated viruses which is substantially composed of encapsidated recombinant poliovirus nucleic acid. As used herein, the phrases "substantially composed" or "substantially comprises" when used to refer to a yield of encapsidated recombinant poliovirus nucleic acids is intended to include a yield of encapsidated recombinant poliovirus nucleic acid which is greater than a yield of encapsidated recombinant poliovirus nucleic acid which is generated through the use of an expression vector which encodes poliovirus capsid proteins but also includes an infectious poliovirus genome. Infectious poliovirus genomes can compete with the recombinant poliovirus nucleic acid for poliovirus capsid proteins, thereby decreasing the yield of encapsidated recombinant poliovirus nucleic acid. Generally, the nucleic acid of the expression vector encodes and directs expression of the nucleotide sequence coding for a capsid protein which the recombinant poliovirus nucleic acid is not capable of expressing. For example, the expression vector can encode the entire P1 capsid precursor protein.

Plasmid expression vectors can typically be designed and constructed such that they contain a gene encoding, in an expressible form, a protein or a portion of a protein necessary for encapsidation of the recombinant poliovirus nucleic acid. Generally, construction of such plasmids can be performed using standard methods, such as those described in Sambrook, J. et al. Molecular Cloning: A Laboratory Manual, 2nd edition (CSHL Press, Cold Spring Harbor, NY 1989). A plasmid expression vector which expresses a protein or a portion of a protein necessary for encapsidation of the poliovirus nucleic acid is constructed by first positioning the gene to be inserted (e.g. VP1, VP2, VP3, VP4 or the entire P1 region) after a DNA sequence known to act as a promoter when introduced into cells. The gene to be inserted is typically positioned downstream (3') from the promoter sequence. The promoter sequence consists of a cellular or viral DNA sequence which has been previously demonstrated to attract the necessary host cell components required for initiation of transcription. Examples of such promoter sequences include the long terminal repeat (LTR) regions of Rous Sarcoma Virus, the origin of replication for the SV40 tumor virus (SV4-ori), and the promoter sequence for the CMV (cytomegalovirus) immediate early protein. Plasmids containing these promoter sequences are available from a number of companies which sell molecular biology products (e.g. Promega (Madison, Wis.), Stratagene Cloning Systems (LaJolla, Calif.), and Clontech (Palo Alto, Calif.).

Construction of these plasmid expression vectors typically requires excision of a DNA fragment containing the gene to be inserted and ligation of this DNA fragment into an expression plasmid cut with restriction enzymes that are compatible with those contained on the 5' and 3' ends of the gene to be inserted. Following ligation of the DNA in vitro, the plasmid is transformed into *E.coli* and the resulting bacteria is plated onto an agar plate containing an appropriate selective antibiotic. The *E. coli* colonies are then grown and the plasmid DNA characterized for the insertion of the particular gene. To confirm that the gene has been ligated into the plasmid, the DNA sequence of the plasmid containing the insert is determined. The plasmid expression vector can be transfected into tissue culture cells using standard techniques and the protein encoded by the inserted gene expressed.

The conditions under which plasmid expression vectors are introduced into a host cell vary depending on certain factors. These factors include, for example, the size of the nucleic acid of the plasmid, the type of host cell, and the desired efficiency of transfection. There are several methods of introducing the recombinant poliovirus nucleic acid into the host cells which are well-known and commonly employed by those of ordinary skill in the art. These transfection methods include, for example, calcium phosphate-mediated uptake of nucleic acids by a host cell and DEAE-dextran facilitated uptake of nucleic acid by a host cell.

Alternatively, nucleic acids can be introduced into cells through electroporation, (Neumann, E. et al. (1982)*EMBO J.* 1:841–845), which is the transport of nucleic acids directly across a cell membrane by means of an electric current or through the use of cationic liposomes (e.g. lipofection, Gibco/BRL (Gaithersburg, Md.)). The methods that are most efficient in each case are typically determined empirically upon consideration of the above factors.

As with plasmid expression vectors, viral expression vectors can be designed and constructed such that they contain a foreign gene encoding a foreign protein or fragment thereof and the regulatory elements necessary for expressing the foreign protein. Viruses suitable for use in the method of this invention include viruses that contain nucleic acid that does not substantially associate with poliovirus capsid proteins. Examples of such viruses include retroviruses, adenoviruses, herpes virus, and Sindbis virus. Retroviruses, upon introduction into a host cell, establish a continuous cell line expressing a foreign protein. Adenoviruses are large DNA viruses which have a host range in human cells similar to that of poliovirus. Sindbis virus is an RNA virus that replicates, like poliovirus, in the cytoplasm of cells and, therefore, offers a convenient system for expressing poliovirus capsid proteins. A preferred viral expression vector is a vaccinia virus. Vaccinia virus is a DNA virus which replicates in the cell cytoplasm and has a similar host range to that of poliovirus. In addition, vaccinia virus can accommodate large amounts of foreign DNA and can replicate efficiently in the same cell in which poliovirus replicates. A preferred nucleotide sequence that is inserted in the vaccinia is the nucleotide sequence encoding and expressing, upon infection of a host cell, the poliovirus P1 capsid precursor polyprotein.

The construction of this vaccinia viral vector is described by Ansardi, D. C. et al. (Apr. 1991)*J. Virol.* 65(4):2088–2092. Briefly, type 1 Mahoney poliovirus cDNA sequences were digested with restriction enzyme Nde I, releasing sequences corresponding to poliovirus nucleotides 3382–6427 from the plasmid and deleting the P2 and much of the P3 encoding regions. Two synthetic oligonucleotides, (5'-TAT-TAG-TAG-ATC-TG (SEQ ID NO: 1)) and 5'-T-ACA-GAT-GTA-CTA-A (SEQ ID NO: 2)) were annealed together and ligated into the Nde I digested DNA. The inserted synthetic sequence is places two translational termination codons (TAG) immediately downstream from the codon for the synthetic P1 carboxy terminal tyrosine residue. Thus, the engineered poliovirus sequences encode an authentic P1 protein with a carboxy terminus identical to that generated when $2A^{pro}$ releases the P1 polyprotein from the nascent poliovirus polypeptide. An additional modification was also generated by the positioning of a Sal I restriction enzyme site at nucleotide 629 of the poliovirus genome. This was accomplished by restriction enzyme digest (Ball) followed by ligation of synthetic Sal I linkers. The DNA fragment containing the poliovirus P1 gene was subcloned into the vaccinia virus recombination plasmid, pSC11. Chackrabarti, S. et at. (1985)*Mol. Cell Biol.* 5:3403–3409. Coexpression of beta-galactosidase provides for visual screening of recombinant virus plaques.

The entry of viral expression vectors into host cells generally requires addition of the virus to the host cell media followed by an incubation period during which the virus enters the cell. Incubation conditions, such as the length of incubation and the temperature under which the incubation is carried out, vary depending on the type of host cell and the type of viral expression vector used. Determination of these parameters is well known to those having ordinary skill in the art. In most cases, the incubation conditions for the infection of cells with viruses typically involves the incubation of the virus in serum-free medium (minimal volume) with the tissue culture cells at 37° C. for a minimum of thirty minutes. For some viruses, such as retroviruses, a compound to facilitate the interaction of the virus with the host cell is added. Examples of such infection facilitators include polybrine and DEAE.

A host cell useful in the present invention is one into which both a recombinant poliovirus nucleic acid and an expression vector can be introduced. Common host cells are mammalian host cells, such as, for example, HeLa cells (ATCC Accession No. CCL 2), HeLa S3 (ATCC Accession No. CCL 2.2), the African Green Monkey cells designated BSC-40 cells, which are derived from BSC-1 cells (ATCC Accession No. CCL 26), and HEp-2 cells (ATCC Accession No. CCL 23). Other useful host cells include chicken cells. Because the recombinant poliovirus nucleic acid is encapsidated prior to serial passage, host cells for such serial passage are preferably permissive for poliovirus replication. Cells that are permissive for poliovirus replication are cells that become infected with the recombinant poliovirus nucleic acid, allow viral nucleic acid replication, expression of viral proteins, and formation of progeny virus particles. In vitro, poliovirus causes the host cell to lyse. However, in vivo the poliovirus may not act in a lytic fashion. Nonpermissive cells can be adapted to become permissive cells, and such cells are intended to be included in the category of host cells which can be used in this invention. For example, the mouse cell line L929, a cell line normally nonpermissive for poliovirus replication, has been adapted to be permissive for poliovirus replication by transfection with the gene encoding the poliovirus receptor. Mendelsohn, C. L. et al. (1989)*Cell* 56:855–865; Mendelsohn, C. L. et al. (1986)*Proc. Natl. Acad. Sci.* USA 83:7845–7849.

The encapsidated recombinant poliovirus nucleic acid of the invention can be used as a vaccine in the form of a composition for stimulating a mucosal as well as a systemic immune response to the foreign protein encoded and expressed by the encapsidated recombinant poliovirus nucleic acid in a subject. Examples of genes encoding proteins that can be inserted into the poliovirus nucleic acid are described above. The mucosal immune response is an important immune response because it offers a first line of defense against infectious agents, such an human immunodeficiency virus, which can enter host cells via mucosal cells. At least a portion of a capsid protein of the encapsidated recombinant poliovirus nucleic acid is supplied by an expression vector which lacks an infectious poliovirus genome. Expression vectors suitable for supplying a capsid protein or a portion thereof are described above. Upon administration of the encapsidated recombinant poliovirus nucleic acid, the subject generally responds to the immunizations by producing both anti-poliovirus antibodies and antibodies to the foreign protein or fragment thereof which is expressed by the recombinant poliovirus nucleic acid. The antibodies produced against the foreign protein or fragment thereof provide protection against the disease or detrimental condition caused by the source of the protein or fragment thereof, e.g., virus, bacteria, or tumor cell. The protection against disease or detrimental conditions offered by these antibodies is greater than the protection offered by the subject's immune system absent administration of the recombinant poliovirus nucleic acids of the invention. The recombinant poliovirus nucleic acid, in either its DNA or RNA form, can also be used in a composition for stimulating a systemic and a mucosal immune response in a subject. Administration of the RNA form of the recombinant poliovirus nucleic acid is preferred as it typically does not integrate into the host cell genome.

The encapsidated recombinant poliovirus nucleic acid or the non-encapsidated recombinant poliovirus nucleic acid can be administered to a subject in a physiologically acceptable carrier and in an amount effective to stimulate an immune response to at least the foreign protein or fragment thereof which is encoded (and its expression directed) by the recombinant poliovirus nucleic acid. Typically, a subject is immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject.

Physiologically acceptable carriers suitable for injectable use include sterile aqueous solutions (where water soluble) or dispersions and sterile powders for the extemporaneous preparation of sterile injectable solutions or dispersions. The composition should typically be sterile and fluid to the extent that easy syringability exists. The composition should further be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

Sterile injectable solutions can be prepared by incorporating the encapsidated recombinant poliovirus nucleic acid in the required amount in an appropriate solvent with one or a combination of ingredients enumerated above, as required, followed by filtered sterilization.

When the encapsidated or nonencapsidated recombinant poliovirus nucleic acid is suitably protected, as described above, the protein can be orally administered, for example, with an inert diluent or an assimilable edible carrier. The protein and other ingredients can also be enclosed in a hard or soft shell gelatin capsule, compressed into tablets, or incorporated directly into the individual's diet. For oral therapeutic administration, the active compound can be incorporated with excipients and used in the form of ingestible tablets, buccal tablets, troches, capsules, elixirs, suspensions, syrups, wafers, and the like.

As used herein "physiologically acceptable carrier" includes any and all solvents, dispersion media, coatings, antibacterial and antifungal agents, isotonic and absorption delaying agents, and the like. The use of such media and agents for physiologically active substances is well known in the art. Except insofar as any conventional media or agent is incompatible with the active compound, use thereof in the therapeutic compositions is contemplated.

Subjects who can be treated by the method of this invention include living organisms, e.g., mammals. Typically, subjects who can be treated by the method of this invention are susceptible to diseases, e.g., infectious diseases, cancer, or are susceptible to a detrimental condition which can be treated by the methods described herein, e.g., a detrimental condition resulting from a nonexistent, deficient, or nonfunctional supply of a protein which is normally produced in the subject. Infectious agents which initiate a variety of diseases include microorganisms such as viruses and bacteria. Examples of subjects include humans, monkeys, dogs, cats, rats, and mice.

The amount of the immunogenic composition which can stimulate an immune response in a subject can be determined on an individual basis and is typically based, at least in part, on consideration of the activity of the specific immunogenic composition used. Further, the effective amounts of the immunogenic composition can vary according to the age, sex, and weight of the subject being treated. Thus, an effective amount of the immunogenic composition can be determined by one of ordinary skill in the art employing such factors as described above using no more than routine experimentation.

The immunogenic composition is administered through a route which allows the composition to perform its intended function of stimulating an immune response to the protein encoded by the recombinant poliovirus nucleic acid. Examples of routes of administration which can be used in this method include parenteral (subcutaneous, intravenous, intramuscular, intra-arterial, intraperitoneal, intrathecal, intracardiac, and intrasternal), enteral administration (i.e. administration via the digestive tract, e.g. oral, intragastric, and intrarectal administration), and mucosal administration. It is important to note that the vaccine strains of poliovirus are routinely tested for attenuation by intramuscular and intracerebral injection into monkeys. Thus, it would probably pose no associated health risk if the recombinant poliovirus nucleic acid was given parenterally. Depending on the route of administration, the immunogenic composition can be coated with or in a material to protect it from the natural conditions which can detrimentally affect its ability to perform its intended function.

Cells that produce the encapsidated poliovirus nucleic acids of the present invention can be introduced into a subject, thereby stimulating an immune response to the foreign protein or fragment thereof encoded by the recombinant poliovirus nucleic acid. Generally, the cells that are introduced into the subject are first removed from the subject and contacted ex vivo with both the recombinant poliovirus nucleic acid and an expression vector as described above to generate modified cells that produce the foreign protein or fragment thereof. The modified cells that produce the foreign protein or fragment thereof can then be reintroduced into the subject by, for example, injection or implantation. Examples of cells that can be modified by this method and injected into a subject include peripheral blood mononuclear cells, such as B cells, T cells, monocytes and macrophages. Other cells, such as cutaneous cells and mucosal cells can be modified and implanted into a subject. Methods of introducing the recombinant poliovirus nucleic acid and the expression vectors of the invention are described above.

The invention is further illustrated by the following non-limiting examples. The contents of all references and issued patents cited throughout this application are expressly incorporated herein by reference.

MATERIALS AND METHODS I:

The following materials and methods were used in Examples 1, 2, 3, and 4:

All chemicals were purchased from Sigma Chemical Co. (St. Louis, Mo.). Restriction enzymes were obtained from New England Bio-labs (Beverly, Mass.). Tissue culture media was purchased from Gibco/BRL Co. (Gaithersburg, Md). $^{35}$S Translabel (methionine-cysteine) and methionine-cysteine-free Dulbecco modified Eagle medium (DMEM) were purchased from ICN Biochemicals (Irvine, Calif.). T7 RNA polymerase was prepared in this laboratory by the method of Grodberg and Dunn. Grodberg, J. and Dunn, J. J. (1988)*J. Bacteriol* 170:1245–1253.

Tissue Culture Cells and Viruses

HeLa (human cervical carcinoma) and BSC-40 cells (African green monkey kidney cells) were grown in DMEM supplemented with 5% A-γ newborn calf serum and 5% fetal calf serum (complete medium). The stock of the poliovirus type 1 Mahoney used in this study was derived from transfection of an infectious cDNA clone obtained from B. Semler, University of California at Irvine. Semler, B. L. et al. (1984)*Nucleic Acids Res.* 12:5123–5141. The stock of type 1 Sabin poliovirus was obtained from the American Type Culture Collection (ATCC Accession No. VR-192). Wild-type vaccinia virus (wt VV) strain WR and the recombinant vaccinia virus VV-P1, which express the poliovirus P1 capsid precursor protein, have been previously described. Ansardi, D. C. et al. (1991)*J. Virol.* 65:2088–2092. Antisera to HIV-1 reverse transcriptase (RT) and HIV-1 p25/24 Gag (Steimer, K. S. et al. (1986)*Virology* 150:283–290) were obtained through the AIDS Research and Reference Reagent Program (Rockville, Md.). Pooled AIDS patient sera was obtained from the Center for AIDS Research, University of Alabama at Birmingham.

In Vitro Transcription Reaction

The in vitro transcription reactions were performed by using T7 RNA polymerase as described previously. Choi, W. S. et al (1991)*J. Virol.* 65:2875–2883. Prior to in vitro transcription, DNA templates were linearized by restriction enzyme digestion, followed by successive phenol-chloroform (1:1) chloroform extractions and ethanol precipitation. Reaction mixtures (100 μl) contained 1 to 5 μg of linearized DNA template, 5×transcription buffer (100 mM Tris [pH 7.7], 50 mM $MgCl_2$, 20 mM spermidine, 250 mM NaCl), 10 mM dithiotheritol, 2mM each GTP, UTP, ATP, and CTP, 40 U of recombinant RNasin (Promega, Madison, Wis.), and approximately 5μg of purified T7 RNA polymerase per reaction mixture.

After 60 min at 37° C., 5% of the in vitro-synthesized RNA was analyzed by agarose gel electrophoresis.

Encapsidation and Serial Passage of Recombinant Poliovirus Nucleic Acids by VV-P1

HeLa cells were infected with 20 PFU of VV-P1 (a recombinant virus which expresses the poliovirus capsid precursor protein P1) or wild type (wt) VV per cell. After 2 hours of infection, the cells were transfected (by using DEAE-dextran [500,000 Da] as a facilitator) with RNA transcribed in vitro from the chimeric HIV-1 poliovirus genomes as previously described. Choi, W. S. et al. (1991)*J. Virol.* 65:2875–2883. The cultures were harvested at 24 hours posttransfection. The cells were lysed with Triton X-100 at a concentration of 1%, treated with RNase A, and clarified by low-speed centrifugation at 14,000×g for 20 min at 4° C. as described previously. Li, G. et al. (1991)*J. Virol.* 65:6714–6723. The supernatants were adjusted to 0.25% sodium dodecyl sulfate (SDS), overlaid on a 30% sucrose cushion (30% sucrose, 30 mM Tris [pH 8.0], 1% Triton X-100, 0.1 M NaCl), and centrifuged in a Beckman SW55Ti rotor at 45,000 rpm for 1.5h. The pelleting procedure described above has been demonstrated to be effective for the removal of infectious vaccinia virus to below detectable levels. The supernatant was discarded, and the pellet was washed by recentrifugation for an additional 1.5 hours in a low salt buffer (30 mM Tris [pH8.0], 0.1 M NaCl). The pellets were then resuspended in complete DMEM and designated passage 1 of the recombinant poliovirus nucleic acids encapsidated by VV-P 1.

For serial passage of the encapsidated recombinant poliovirus nucleic acids, BSC-40 cells were infected with 20 PFU of VV-P1 per cell. At 2 hours postinfection, the cells were infected with passage 1 of the encapsidated recombinant poliovirus nucleic acids. The cultures were harvested at 24 hours postinfection by three successive freeze-thaws, sonicated, and clarified by centrifugation at 14,000×g for 20 min. The supernatants were then stored at −70° C. or used immediately for additional passages following the same procedure.

Metabolic Labeling and Immunoprecipitation of Viral Proteins

To metabolically label viral proteins from infected-transfected or infected cells, the cultures were starved for methionine-cysteine at 6 hours postinfection by incubation in DMEM minus methionine-cysteine for 30 minutes. At the end of this time, $^{35}$S Translabel was added for an additional hour. Cultures were then processed for immunoprecipitation of viral proteins by lysing the cells with radioimmunoprecipitation assay (RIPA) buffer (150 mM NaCl, 10 mM Tris [pH 7.8], 1% Triton X-100, 1% sodium deoxycholate, 0.2% SDS). Following centrifugation at 14,000×g for 10 min to pellet any debris, designated antibodies were added to the supernatants, which were incubated at 4° C. rocking for 24 hours. The immunoprecipitates were collected by addition of 100 $\mu$l of protein A-Sepharose (10% [wt/vol] in RIPA buffer). After 1 hour of rocking at room temperature, the protein A-Sepharose beads were collected by brief configuration and washed three times with RIPA buffer. The bound material was eluted by boiling for 5 minutes in gel sample buffer (50 mM Tris [pH 6.8], 5% SDS, 10% glycerol, 0.01% bromophenol blue, 10% β-mercaptoethanol). The proteins were analyzed by SDS polyacrylamide gel electrophoresis, and radiolabeled proteins were visualized by fluorography.

Nucleic Acid Hybridization

RNA from a stock of recombinant poliovirus nucleic acids encapsidated by VV-P 1 was analyzed by Northern (RNA) blotting. Stocks of encapsidated recombinant poliovirus nucleic acids at passage 14 and a high-titer stock of type 1 Mahoney poliovirus were subjected to RNase A treatment and overlaid on 30% sucrose cushion (30% sucrose, 30mM Tris [pH 8.0], 1% Triton X-100, 0.1 M NaCl). The samples were centrifuged in a Beckman SW55Ti rotor at 45,000 rpm for 1.5h. Pelleted virions were resuspended in TSE buffer (10 mM Tris-HCl [pH 8.0], 50 mM EDTA) and adjusted to 1% SDS and 1% β-mercaptoethanol as previously described. Rico-Hesse, R. et al. (1987)*Virology* 160:311–322. The resuspended virions were disrupted by extraction three times with phenol-chloroform equilibrated to acidic buffer and one time with chloroform. The extracted RNA was precipitated with 0.2 M $LiCl_2$, and 2.5 volumes 100% ethanol. The RNA was denatured and separated on a formaldehyde-agarose gel. The RNA was then transferred from the gel to a nitrocellulose filter by capillary elution (Sambrook, J. et al. (1989) Molecular Cloning: A Laboratory Manual, 2nd edition (Cold Spring Harbor Laboratory Press, NY)) and cross-linked by using a UV Stratalinker (Stratagene, LaJolla, Calif.). The conditions used for prehybridization, hybridization, and washing of RNA immobilized on filters were previously described (Sambrook, J. et al. (1989) Molecular Cloning: A Laboratory Manual, 2nd edition (Cold Spring Harbor Laboratory Press, NY)). Briefly, the blot was prehybridized in hybridization buffer (50% deionized formamide, 6×SSC [1×SSC is 0.15 M NaCl plus 0.015 M sodium citrate], 1% SDS, 0.1% Tween 20, 100$\mu$g of yeast tRNA per ml). The blot was then incubated in hybridization buffer containing $10^6$ cpm of a [$^{32}$p] UTP-labeled riboprobe complementary to nucleotides 671 to 1174 of the poliovirus genome (Choi, W. S. et al (1991) *J. Virol.* 65:2875–2883) per ml. After hybridization, the blot was washed two times with 0.1×SSC-0.1% SDS at room temperature and one time at 65° C. The blot was then exposed to X-ray film with an intensifying screen.

Neutralization of The Recombinant Poliovirus Nucleic Acids Encapsidated by VV-P1 Using Anti-poliovirus Antibodies For antibody neutralization, encapsidated recombinant poliovirus nucleic acids at passage 9 were pelleted by ultracentrifugation and resuspended in 250 $\mu$l of phosphate-buffered saline (pH 7.0)-0.1% bovine serum albumin. Samples were preincubated with 25$\mu$l of either rabbit anti-poliovirus type 1 Mahoney antisera or preimmune sera per sample at 37° C. for 2 hours. Neutralization experiments were conducted on the basis of the results of preliminary experiments analyzing the capacity of anti-poliovirus antisera to prevent infection of cells by $10^6$ total PFU of poliovirus under the experimental conditions. The preincubated samples were then analyzed for protein expression by infection of BSC-40 cells which were metabolically labeled at 6 hours postinfection followed by immunoprecipitation of viral proteins.

Encapsidation of The Recombinant Poliovirus Nucleic Acids by Type 1 Sabin Poliovirus BSC-40 cells were coinfected with 10 PFU of type 1 Sabin poliovirus and a stock of encapsidated recombinant poliovirus nucleic acids (passage 14) per cell. The infected cells were harvested at 24 hours postinfection by three successive freeze-thaws, sonicated and clarified by centrifugation at 14,000×g for 20 minutes as described previously (Li, G., et al.

J. Virol. 65:6714–6723). Approximately one-half of the supernatant was used for serial passaging by reinfection of BSC-40 cells. After 24 hours, the cultures were harvested as described above, and the procedure was repeated for an additional 10 serial passages.

EXAMPLE 1

EXPRESSION OF RECOMBINANT POLIOVIRUS NUCLEIC ACID IN WHICH THE VP2 AND VP3 REGIONS OF THE POLIOVIRUS GENOME ARE REPLACED WITH A PORTION OF THE HIV-1 GAG OR POL GENES IN CELLS INFECTED WITH AN EXPRESSION VECTOR WHICH EXPRESSES THE POLIOVIRUS CAPSID PRECURSOR PROTEIN P1

Figure 2A:
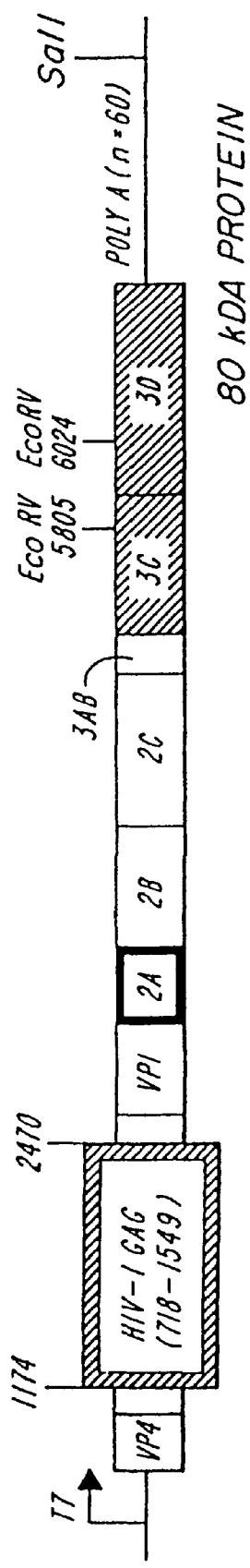
FIGS. 2A, 2B, and 2C show chimeric HIV-1-poliovirus genomes containing regions of the HIV-1 gag or pol gene substituted for the poliovirus is P1 gene.
Figure 2B:
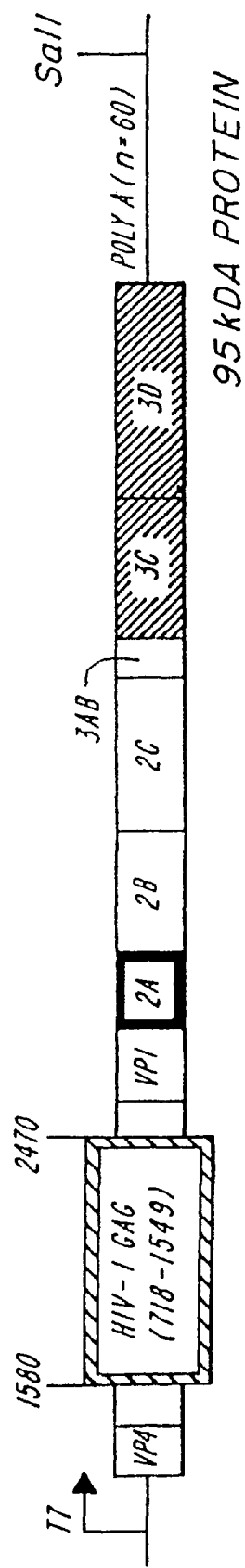
Figure 2C:
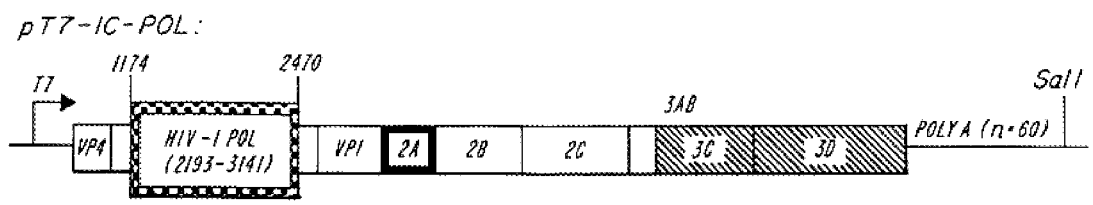

The construction and characterization of recombinant poliovirus nucleic acid in which the HIV-1 gag or pol gene was substituted for VP2 and VP3 regions of the poliovirus P1 protein in the infectious cDNA of poliovirus have previously been described. Choi, W. S. et al (1991)$J.$ $Virol.$ 65:2875–2883 (FIG. 2). FIG. 2 shows chimeric HIV-1-poliovirus genomes containing regions of the HIV-1 gag or pol gene substituted for the poliovirus P1 gene. Details of the construction of plasmids pT7-IC-GAG 1 and pT7-IC-POL have been described by Choi et al. and were presented as pT7IC-NheI-gag and pT71C-NheI-pol, respectively. To construct pT7-IC-GAG 2, a unique SmaI site was created at nucleotide 1580 of the infectious cDNA or poliovirus, and the HIV-1 gag sequences were subcloned between nucleotides 1580 and 2470. Insertion of the HIV-1 genes maintains the translational reading frame with VP4 and VP1. In vitro transcription from these plasmids generates full-length RNA transcripts (linearized with SalI). Transfection of full-length transcripts into HeLa cells results in expression of the poliovirus 3CD protein, a fusion protein between the 3CD and the $3D^{pol}$ proteins with a molecular mass of 72 kDa. The molecular masses of the HIV-1-P1 fusion proteins are indicated. In previous studies, transfection of these chimeric RNA genomes into type 1 Mahoney poliovirus-infected cells did not result in encapsidation of these RNA genomes (Choi, W. S. et al (1991)$J.$ $Virol.$ 65:2875–2883). Under the experimental conditions used, it was possible that the recombinant poliovirus nucleic acid did not efficiently compete with wild-type RNA genomes for capsid proteins. To circumvent this problem, a recombinant vaccinia virus (VV-P1) which expresses the poliovirus capsid precursor protein P1 upon infection was used, since recent studies have shown that in cells coinfected with VV-P1 and poliovirus, P1 protein expressed from VV-P1 can enter the encapsidation pathways of wild type poliovirus.

Figure 3:
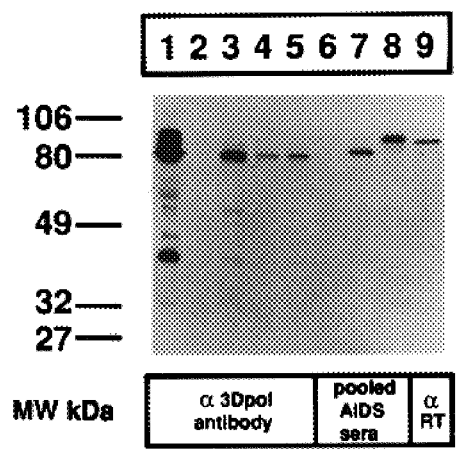
FIG. 3 shows an SDS-polyacrylamide gel on which $3D^{pol}$ and HIV-1-P1 fusion protein expression from cells infected with VV-P1 and transfected with recombinant poliovirus RNA was analyzed.

Protein expression from the recombinant poliovirus nucleic acid transfected into cells previously infected with the recombinant vaccinia virus VV-P1 was analyzed. (FIG. 3) FIG. 3 shows an analysis of $3D^{pol}$ and HIV-1-P1 fusion protein expression from cells infected with VV-P1 and transfected with recombinant poliovirus nucleic acid RNAs. Cells were infected with VV-P1 at a multiplicity of infection of 20. At 2 hours postinfection, cells were transfected with RNA derived from in vitro transcription of the designated plasmids. Cells were metabolically labeled and cells extracts were incubated with anti-$3D^{pol}$ antibodies (lanes 1 to 5), pooled AIDS patient sera (lanes 6 to 8), or anti-RT antibodies (lane 9), and immunoreactive proteins were analyzed on SDS-polyacrylamide gels. Lanes: 1, cells infected with wild-type poliovirus: 2 and 6, mock-transfected cells: 3 and 7, cells transfected with RNA derived from pT7-IC-GAG 1:4 and 8, cells transfected with RNA derived from pT7-IC-GAG 2; 5 and 9, cells transfected with RNA derived from pT7-IC-POL. The positions of molecular mass standards are indicated. A protein of molecular mass 72 kDa, corresponding to the 3CD protein of poliovirus, was immunoprecipitated by anti-$3D^{pol}$ antibodies from cells transfected with the recombinant poliovirus RNA but not from mock-transfected cells. Under the same conditions for metabolic labeling, the 3CD protein, which is a fusion protein between the $3C^{pol}$ and $3D^{pol}$ proteins of poliovirus, is predominately detected upon incubation of lysates from poliovirus infected cells with $3D^{pol}$ antisera to determine whether the appropriate HIV-1-P1 fusion proteins were also expressed, the extracts were incubated with pooled AIDS patient sera (gag) or rabbit anti-RT antibodies (pol). Expression of the HIV-1-Gag-P1 fusion proteins corresponding to the predicted molecular masses 80 and 95 kDa were detected from cells transfected with RNA genomes derived by in vitro transcription of pT7-IC-GAG 1 and pT7-IC-GAG 2, respectively. Similarly, an HIV-1 Pol-P1 fusion protein of the predicted molecular mass 85 kDa was immunoprecipitated from cells transfected with RNA derived from the in vitro transcription of pT7-IC-POL. These results demonstrate that transfection of the recombinant poliovirus RNA into VV-P1 infected cells results in the expression of appropriate HIV-1-P1 fusion proteins as well as $3D^{pol}$ related proteins.

EXAMPLE 2

ENCAPSIDATION AND SERIAL PASSAGE OF RECOMBINANT POLIOVIRUS NUCLEIC ACID IN WHICH THE VP2 AND VP3 REGIONS OF THE POLIOVIRUS GENOME ARE REPLACED WITH A PORTION OF THE HIV-1 GAG OR POL GENES IN CELLS WITH AN EXPRESSION VECTOR WHICH EXPRESSES THE POLIOVIRUS CAPSID PRECURSOR PROTEIN P1

Figure 4A:
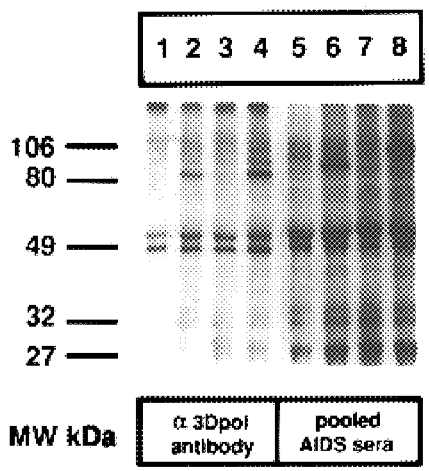
FIGS. 4A, 4B, and 4C show SDS-polyacrylamide gels on which poliovirus- and HIV-1-specific protein expression from cells infected with recombinant poliovirus RNA which were encapsidated and serially passaged with capsid proteins provided by VV-P1 were analyzed.
Figure 4B:
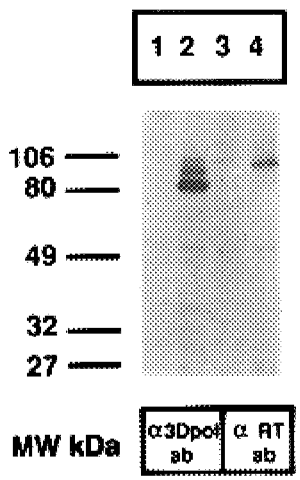

In order to determine whether transfection of the recombinant poliovirus nucleic acids encoding the HIV-1 gag and pol genes into VV-P1 infected cells would result in encapsidation of the recombinant poliovirus nucleic acid, the recombinant poliovirus RNA's were transfected into either VV-P1 or wt VV-infected cells, and the encapsidation genomes were isolated as described in Materials and Methods I. The pelleted material was then used to reinfect cells. This procedure was followed by metabolic labeling of viral proteins and incubation with anti-$3D^{pol}$ or HIV-1- antisera (FIGS. 4A and 4B). FIGS. 4A and 4B show an analysis of poliovirus- and HIV-1-specific protein expression from cells infected with recombinant poliovirus nucleic acids which were encapsidated and serially passaged with capsid proteins provided by VV-P1. Cells were infected with VV-P1 or wt VV at a multiplicity of infection of 20 and transfected with RNA derived from in vitro transcription the designated plasmids. The cells were harvested for isolation of encapsidated genomes as described in Materials and Methods I. The pelleted material was used to reinfect cells, which were metabolically labeled, and cell lysates were incubated with the designated antibodies. Immunoreactive proteins were analyzed on SDS-polyacrylamide gels. FIG. 4A: Lanes: 1 and 5, cells infected with pelleted material derived from cells infected with wt VV and transfected with RNA derived from pT7-IC-GAG 1; 2 and 6, cells infected with pelleted material derived from cells infected with VV-P1 and transfected with RNA derived from pT7-IC-GAG 1; 3 and 7, cells infected with pelleted material derived from cells infected with wt VV and transfected with RNA derived from pT7-IC-GAG 2; 4 and 8, cells infected with pelleted material derived from cells infected with VV-P1 and transfected with RNA derived from pT7-IC-GAG2. FIG. 4B: Lanes: 1 and 3, cells infected with pelleted material derived from cells infected with wt VV and transfected with RNA derived from pT7-IC-POL; 2 and 4, cells infected with pelleted material derived from cells infected with VV-P1 and transfected with RNA derived from PT7-IC-POL.

The poliovirus 3CD protein was immunoprecipitated from cells infected with pelleted material derived from transfection of the recombinant poliovirus RNA into VV-P1 infected cells. The molecular masses of the HIV-1-P1 fusion proteins immunoprecipitated from the infected cells were consistent with the predicted molecular masses and those observed from expression of the recombinant poliovirus nucleic acid in transfected cells (FIG. 2). No 3D$^{pol}$ or HIV-1-P1 proteins were detected from cells infected with material derived from transfection of the chimeric genomes into wt VV-infected cells, demonstrating a requirement for the poliovirus P1 protein for encapsidation of the recombinant poliovirus nucleic acid.

Figure 4C:
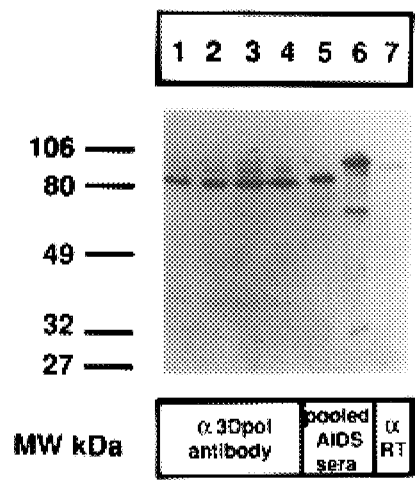
Figure 8A:
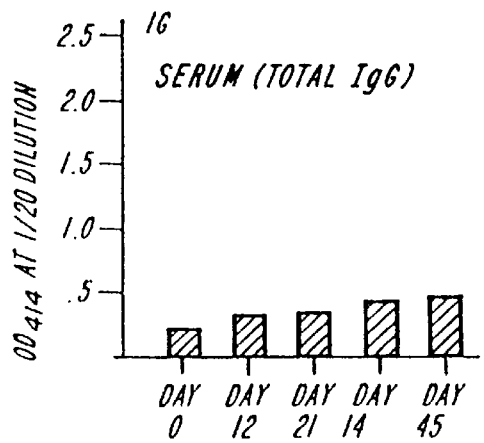
FIGS. 8A, 8B, and 8C show total anti-poliovirus IgG levels in serum from mice after intragastric, intrarectal, and intramuscular administration of an encapsidated recombinant poliovirus nucleic acid encoding and expressing at least a portion of the gag protein of human immunodeficiency virus type 1.
Figure 8B:
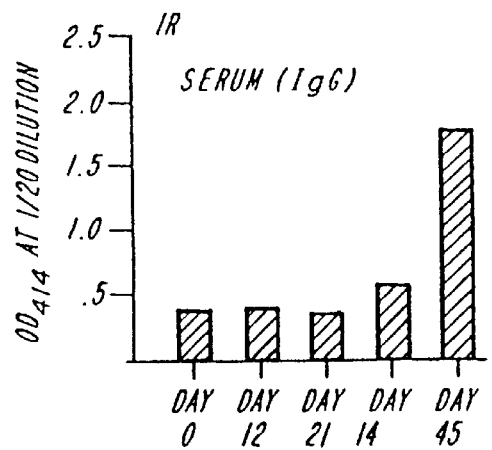
Figure 8C:
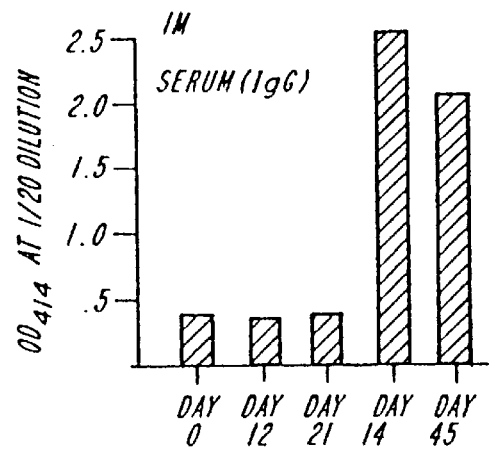
Figure 9A:
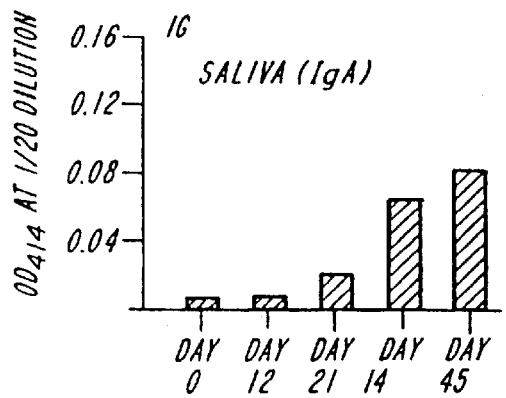
FIGS. 9A, 9B, and 9C show anti-poliovirus IgA levels in saliva from mice after intragastric, intrarectal, and intramuscular administration of an encapsidated recombinant poliovirus nucleic acid encoding and expressing at least a portion of the gag protein of human immunodeficiency virus type 1.
Figure 9B:
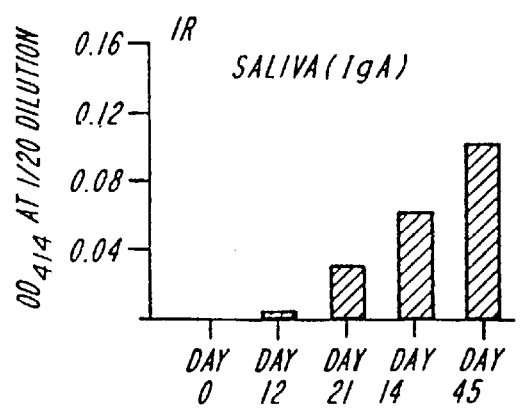
Figure 9C:
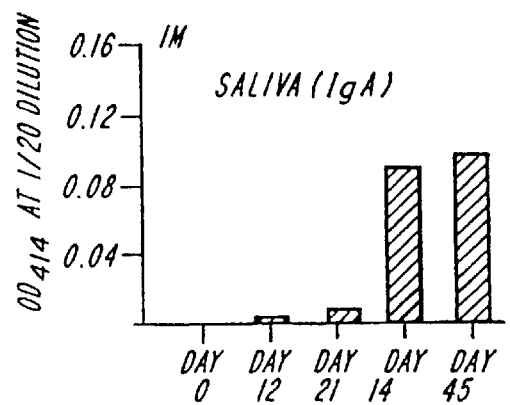
Figure 10A:
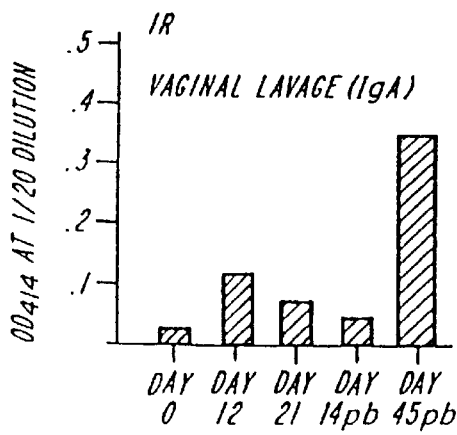
FIGS. 10A and 10B show anti-poliovirus IgA in vaginal lavages after intrarectal, and intramuscular administration of an encapsidated recombinant poliovirus nucleic acid encoding and expressing at least a portion of the gag protein of human immunodeficiency virus type 1.
Figure 10B:
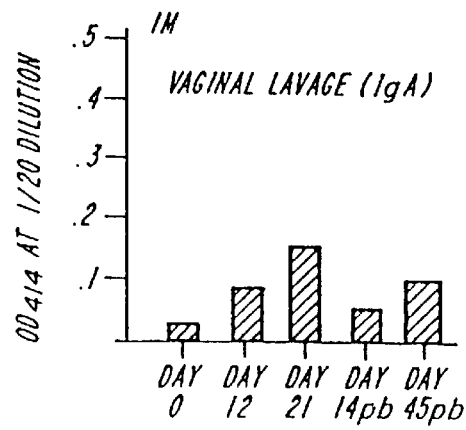
Figure 11A:
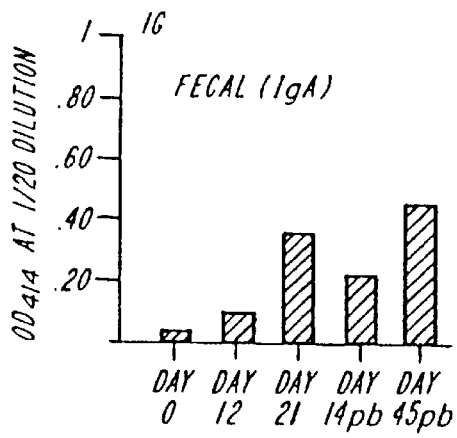
Figure 11B:
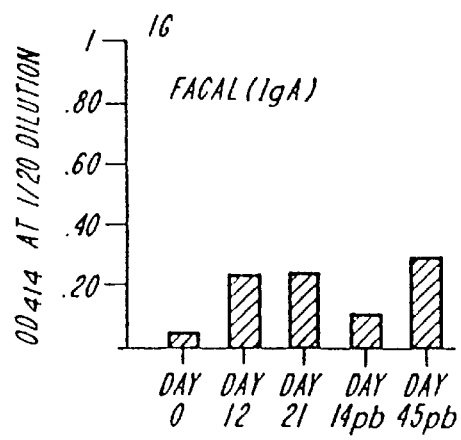
Figure 11C:
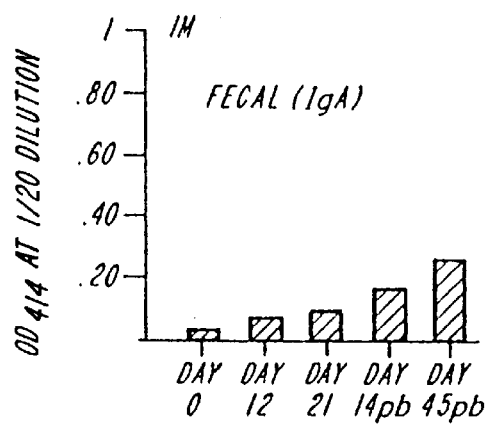
Figure 12A:
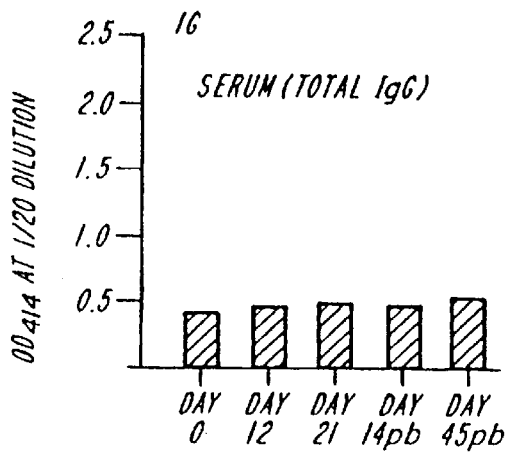
Figure 12B:
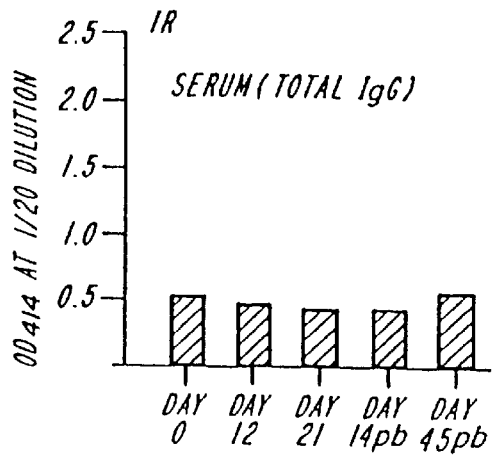
Figure 12C:
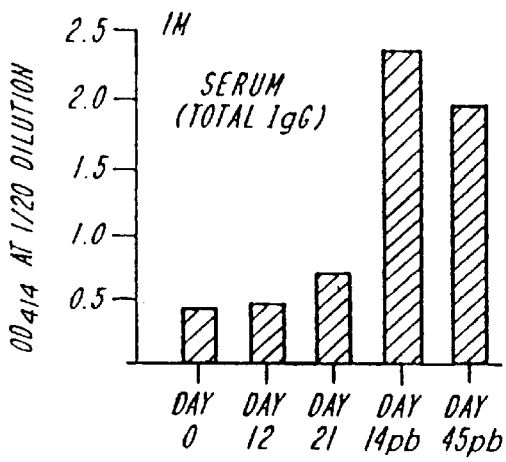
Figure 13A:
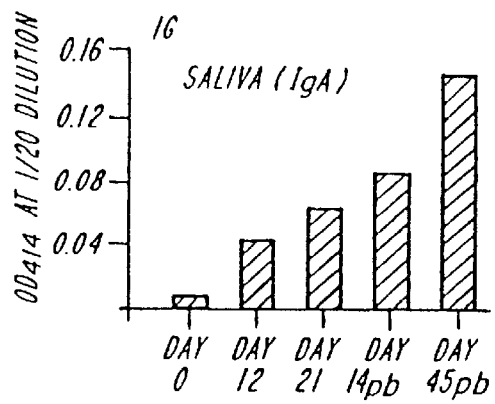
Figure 13B:
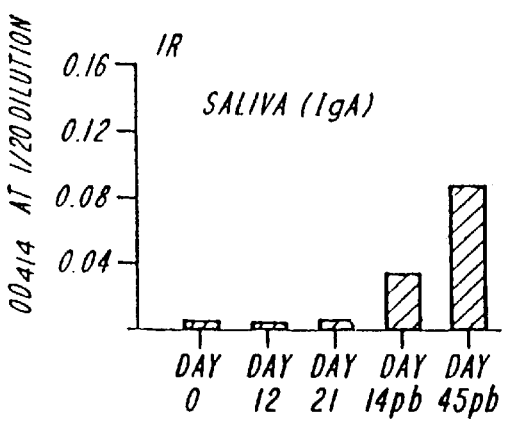
Figure 13C:
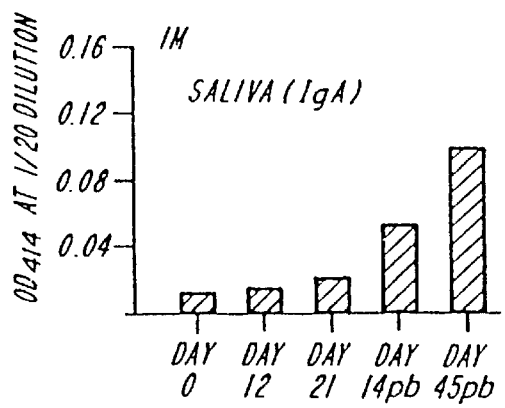
Figure 14A:
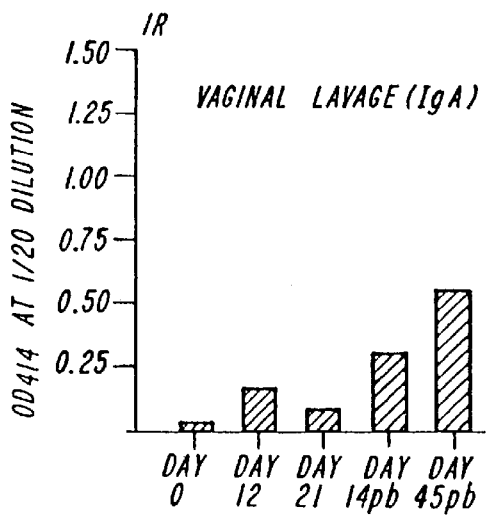
Figure 14B:
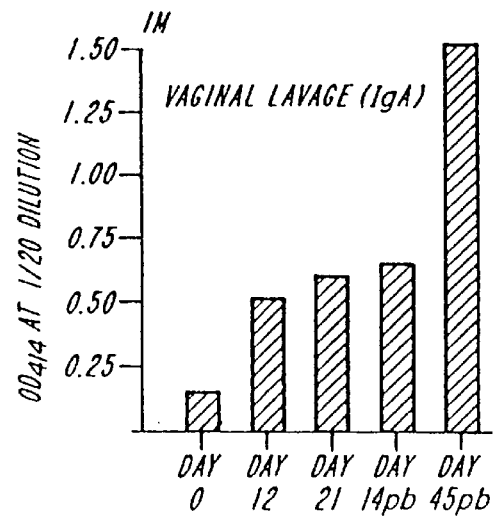
Figure 15A:
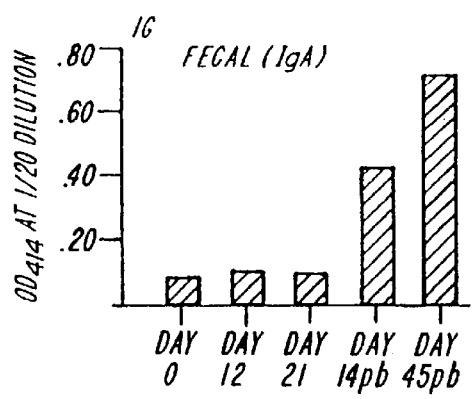
Figure 15B:
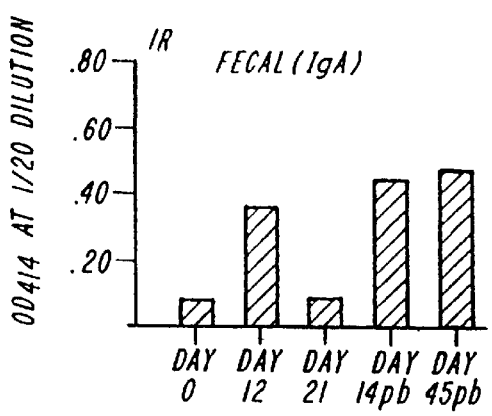
Figure 15C:
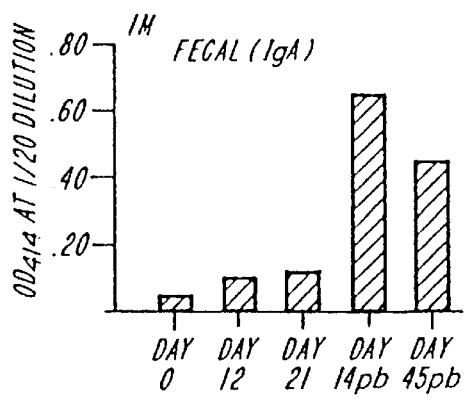

To determine whether the encapsidated recombinant poliovirus nucleic acid could be serially passaged, passage 1 stock of the encapsidated recombinant poliovirus nucleic acid was used to infect cells that had been previously infected with VV-P1. After 24 hours, the encapsidated recombinant poliovirus nucleic acids were isolated as described in Materials and Methods I and subsequently used to reinfect cells which had been previously infected with VV-P1; this procedure was repeated for an additional nine passages. By convention the stocks of serially passaged recombinant poliovirus RNA are referred to as vIC-GAG 1, vIC-GAG 2, or vIC-POL. Cells were infected with passage 9 material and metabolically labeled and the lysates were incubated with antisera to poliovirus 3D$^{pol}$ protein or antibodies to HIV-1 proteins (FIG. 4C). In FIG. 4C, stocks of the encapsidated recombinant poliovirus nucleic acids were also used to infect cells which had been previously infected with VV-P1for serial passage of the encapsidated genomes as described in Materials and Methods I. Cells were infected with serially passaged stocks of recombinant poliovirus nucleic acids at passage 9 and metabolically labeled, and cell extracts were incubated with the designated antibodies (ab). Immunoreactive proteins were analyzed on SDS-polyacrylamide gels. Lanes: 1, cells infected with wild-type poliovirus; 2 and 5, cells infected with vIC-GAG 1; 3 and 6, Cells infected with vIC-GAG2; 4 and 7, cells infected with vIC-POL. The positions of molecular mass standards are indicated.

The poliovirus 3CD protein was immunoprecipitated from cells infected with poliovirus and the encapsidated recombinant poliovirus nucleic acids. The HIV-1-Gag-P1 and HIV-1-Pol-P1 fusion proteins were also immunoprecipitated from cells infected with the serially passaged recombinant poliovirus nucleic acids. In contrast, no immunoreactive proteins were detected from cells which were infected with VV-P1 alone and immunoprecipitated with the same antisera (FIG. 3).

To determine whether the encapsidated recombinant poliovirus nucleic acids had undergone any significant deletion of genome size as a result of serial passage with VV-P1, RNA isolated from vIC-GAG 1 at passage 14 was analyzed by Northern blotting (FIG. 5). FIG. 5 shows a Northern blot analysis of RNA isolated from a stock of encapsidated recombinant poliovirus nucleic acids. Virions were isolated by ultracentrifugation from a stock of vIC-GAG 1 at passage 14 and from type 1 Mahoney poliovirus. The isolated virions were disrupted, and the RNA was precipitated, separated in a formaldehyde-agarose gel, and transferred to nitrocellulose. Lanes: 1, RNA isolated from vIC-GAG 1 stock; 2, RNA isolated from poliovirions. Note that the exposure time for the sample in lane 1 of the gel was six times longer than that for lane 2.

For these studies, a riboprobe complementary to nucleotides 671 to 1174 of poliovirus, present in the HIV-1-poliovirus chimeric genomes, was used. RNA isolated from vIC-GAG 1 was compared with RNA isolated from type 1 Mahoney poliovirions. The migration of the RNA isolated from vIC-GAG 1 was slightly faster than that of the wild-type poliovirus RNA, consistent with the predicted 7.0-kb size for RNA from pT7-IC-GAG 1 versus the 7.5-kb size for wild-type poliovirus RNA. Furthermore, a single predominant RNA species from vIC-GAG 1 was detected, indicating that no significant deletions of the RNA had occurred during the serial passages.

Antibody Neutralization of Recombinant Poliovirus Nucleic Acid Encapsidated by VV-P1.

To confirm that the recombinant poliovirus nucleic acid RNA passaged with VV-P1 was encapsidated in poliovirions, the capacity of poliovirus-specific antisera to prevent expression of the HIV-1-P1 fusion proteins and poliovirus 3CD protein was analyzed. The results of this experiment are important to exclude the possibility that the recombinant poliovirus nucleic acids were being passaged by inclusion into VV-P1 rather than poliovirions. For these studies, passage 9 material of vIC-GAG 1 was preincubated with preimmune type 1 poliovirus antisera as described in Materials and Methods I. After incubation, the samples were used to infect cells, which were then metabolically labeled, and cell lysates were analyzed for expression of poliovirus- and HIV-1 specific proteins after incubation with anti-3D$^{pol}$ antisera and pooled AIDS patient sera, respectively (FIG. 6). FIG. 6 shows neutralization of recombinant poliovirus nucleic acids encapsidated by VV-P1 with anti-poliovirus antibodies. Cells were infected with a passage 9 stock of vIC-GAG 1 that had been preincubated with anti-poliovirus type 1 antisera or preimmune sera as described in Materials and Methods I. Infected cells were metabolically labeled, cell lysates were incubated with anti-3D$^{pol}$ antibodies (lanes 1 to 3) or pooled AIDS patient sera (lanes 4 and 5), and immunoreactive proteins were analyzed on SDS-polyacrylamide gels. Lanes: 1, cells infected with wild-type poliovirus (no neutralization); 2 and 4, cells infected with vIC-GAG 1 which had been preincubated with preimmune sera: 3 and 5, cells infected with vIC-GAG 1 which had been preincubated with anti-poliovirus type 1 antisera. The positions of molecular mass standards are indicated.

No expression of the poliovirus 3CD or HIV-1-Gag-P1 fusion protein was detected from cells infected with vIC-GAG 1 which had been preincubated with the anti-poliovirus antibodies. Expression of 3CD protein and HIV-1-Gag-P1 fusion protein was readily detected from cells infected with vIC-GAG 1 which had been preincubated with normal rabbit serum (preimmune). These results demonstrate that the recombinant poliovirus nucleic acids were encapsidated by P1 protein provided in trans by VV-P1 which could be neutralized by anti-poliovirus antibodies.

Encapsidation of Serially Passaged Recombinant Poliovirus Nucleic Acids by Poliovirus To determine whether the recombinant poliovirus nucleic acid genomes could be encapsidated by P1 protein provided in trans from wild-type poliovirus, cells were coinfected with type 1 Sabin poliovirus and passage 14 stock of vIC-GAG 1. After 24 hours, the coinfected cells were harvested as described in Materials and Methods I, and the extracted material was serially passaged 10 additional times at a high multiplicity of infection. Cells were infected with passage 10 material of vIC-GAG 1 and type 1 Sabin poliovirus and metabolically labeled, and cell extracts were incubated with antibodies to type 1 Sabin poliovirus (FIG. 7A), pooled sera from AIDS patients (FIG. 7B), and anti-p24 antibodies (FIG. 7C) and the immunoreactive proteins were analyzed on SDS polyacrylamide gels. Lanes: 1, cells infected with type 1 Sabin poliovirus alone; 2, cells infected with material derived from passage 10 of vIC-GAG 1 and type 1 Sabin poliovirus. The positions of relevant proteins are indicated.

Poliovirus capsid proteins were detected from cells infected with type 1 Sabin poliovirus alone and from cells infected with material derived from passaging vIC-GAG 1 with type 1 Sabin poliovirus. No HIV-1 specific proteins were detected from cells infected with type 1 Sabin poliovirus alone. A slight cross-reactivity of the HIV-1-Gag-P1 fusion protein with anti-poliovirus antisera was detected in extracts of cells infected with material derived from passaging vIC-GAG 1 with type 1 Sabin poliovirus (FIG. 7A). Although the HIV-1-Gag-P1 fusion protein was clearly detected from cells with type 1 Sabin poliovirus after incubation with pooled AIDS patient sera, some cross-reactivity of the poliovirus capsid proteins were also detected (FIG. 7B). To confirm that the HIV-1-Gag-P1 fusion protein had been immunoprecipitated from extracts of cells infected with material derived from passaging vIC-Gag 1 with type 1 Sabin poliovirus, the extracts were incubated with rabbit anti-p24 antiserum (FIG. 7C). Again, detection of the HIV-1-Gag-P1 fusion protein was evident from cells infected with material derived from passaging vIC-GAG 1 with type 1 Sabin poliovirus but not from cells infected with type 1 Sabin alone. Furthermore, HIV-1-Gag-P1 fusion protein expression was detected after each serial passage (1 to 10) of vIC-GAG 1 with type 1 Sabin poliovirus. These results demonstrate that the chimeric recombinant poliovirus nucleic acids can be encapsidated by P1 protein provided in trans from type 1 Sabin poliovirus under the appropriate experimental conditions and are stable upon serial passage.

EXAMPLE 3

PRODUCTION OF ANTI-POLIOVIRUS AND ANTI-GAG ANTIBODIES IN MICE IMMUNIZED WITH ENCAPSIDATED RECOMBINANT POLIOVIRUS NUCLEIC ACID CONTAINING A PORTION OF THE HIV-1 GAG GENE

The construction and characterization of chimeric HIV-1 poliovirus nucleic acid in which the HIV-1 gag gene was substituted for VP2 and VP3 regions of the poliovirus P1 protein in the infectious cDNA of poliovirus was performed as described previously. Choi, W. S. et al. (1991)*J. Virol.* 65:2875–2883. To evaluate both qualitatively and quantitatively the immune responses against HIV-1 gag expressed from recombinant poliovirus nucleic acid, BALB/c mice (5 animals in each of three groups) were immunized by parenteral (intramuscular), oral (intragastric) or intrarectal routes. The doses were $2.5 \times 10^5$ virus PFU poliovirus/mouse for systemic immunization (intramuscular) and $2.5 \times 10^6$ PFU poliovirus/mouse for oral immunization. It is important to note that the titer refers only to the type II Lansing in the virus preparation, since the encapsidated recombinant poliovirus nucleic acid alone does not form plaques due to deletion of the P1 capsids. For oral immunization, the antigen was resuspended in 0.5 ml of RPMI 1640 and administered by means of an animal feeding tube (Moldoveanu et al. (1993)*J. Infect. Dis.* 167:84–90). Intrarectal immunization was accomplished by application of a small dose of virus in solution (10 µl/mouse intrarectally). Serum, saliva, fecal extract and vaginal lavage were collected before immunization, and two weeks after the initial dose of the virus.

Collection of Biological Fluids

Biological fluids were collected two weeks after the primary immunization, and one week after the secondary immunization. The methods for obtaining biological fluids are as follows:

Blood was collected from the tail vein with heparinized glass capillary tubes before and at selected times after immunization. The blood was centrifuged and plasma collected and stored at −70° C.

Stimulated saliva was collected with capillary tubes after injection with carbamyl-choline (1–2µg/mouse). Two µg each of soybean trypsin inhibitor and phenylmethylsulfonyl fluoride (PMSF) was added to the sample followed by clarification by centrifugation at 800×g for 15 minutes. Sodium azide (0.1% final concentration) and FCS (1% final concentration) was added after clarification and the sample stored at −70° C. until the assay.

Vaginal lavages were performed in mice by applying approximately 50 µl sterile PBS into the vagina and then aspirating the outcoming fluid.

Intestinal lavages were performed according to the methods previously described by Elson et al. (Elson, C.O. et al. (1984)*J. Immunol. Meth.* 67:101–108). For those studies, four doses of 0.5 ml lavage solution (isoosmotic for mouse gastrointestinal secretion) was administered at 15 minute intervals using an intubation needle. Fifteen minutes after the last dose of lavage, 0.1 µg of polycarbine was administered by intraperitoneal injection to the anesthetized mouse. Over the next 10 to 15 minutes the discharge of intestinal contents was collected into a petri dish containing a 5 ml solution of 0.1 mg/mil trypsin soybean inhibitor and 5 mM EDTA. The solid material was removed by centrifugation (650×g for 10 minutes at 4° C.) and the supernatant collected. Thirty µl of 100 mM PMSF was then added followed by further clarification at 27,000×g for 20 minutes at 4° C. An aliquot of 10 µl of 0.1% sodium azide and 10% fetal calf serum was added before storage at −70° C.

Fecal Extract was prepared as previously described (Keller, R., and Dwyer, J. E. (1968)*J. Immunol.* 101:192–202).

Enzyme-Linked Immunoabsorbant Assay

An ELISA was used for determining antigen-specific antibodies as well as for total levels of immunoglobulins. The assay was performed in 96-well polystyrene microtiter plates (Dynatech, Alexandria, Va.). For coating, purified poliovirus (1 µg/well) or HIV specific proteins, or solid phase adsorbed, and affinity-purified polyclonal goat IgG antibodies specific for mouse IgG, IgA or IgM (Southern Biotechnology Associates, Birmingham, Ala. (SBA)(1 µg/well)) were employed. Dilutions of serum or secretions were incubated overnight at 4° C. on the coated and blocked ELISA plates and the bound immunoglobulins were detected with horseradish peroxidase-labeled goat IgG against mouse Ig, IgA, IgG, or IgM (SBA). At the end of the incubation time (3 hours at 37° C.), the peroxidase substrate 2,2-azino bis. (3-ethylbenzthiazoline) sulfonic acid (ABTS) (Sigma, St. Louis, Mo.) in citrate buffer pH 4.2 containing 0.0075% $H_2O_2$ was added. The color developed was measured in a Titertek Multiscan photometer (Molecular Devices, Palo Alto, Calif.) at 414 nm. To calibrate the total level of mouse IgA, IgG, IgM levels, purified mouse myeloma proteins served as standards. For antigen-specific ELISA, the optical densities were converted to ELISA units, using calibration curves obtained from optical density values obtained from reference pools of sera or secretions. The calibration curves were constructed using a computer program on either 4-parameter logistic or weighed logit-log models. End point titration values were an alternative way of expressing the results. The fold increase values were calculated by dividing post-immunization by pre-immunization values expressed in ELISA units.

Anti-Poliovirus Antibodies

The levels of anti-poliovirus antibodies were determined by ELISA at Day 0 (preimmune), Days 12, and 21 post immunization. A second administration of encapsidated recombinant poliovirus nucleic acid was given by the same route at day 21, and samples were collected 14 days post to second booster and 45 days post second booster. FIGS. 8A, 8B, and 8C show serum anti-poliovirus antibodies (designated total IgG, representing predominantly IgG, with minor contribution of IgM and IgA) for animals immunized via the intragastric, intrarectal, or intramuscular route. The samples from each of the 5 animals within the group were pooled, and the ELISA was used to determine the amounts of anti-poliovirus antibodies at a 1:20 dilution. A very slight increase in the anti-poliovirus antibodies present in the serum of mice immunized via the intragastric route was observed at Day 45 post booster immunization when compared to the pre-immune levels at Day 0. A clear increase in the serum anti-poliovirus antibodies was observed in the animals immunized via the intragastric or intramuscular route at Day 14 and Day 45 post booster immunization. The levels at Day 14 and 45 post booster immunization were approximately 5-fold over that observed for the background levels at Day 0.

In FIGS. 9A, 9B, and 9C, IgA anti-poliovirus antibodies present in the saliva of animals immunized with the encapsidated recombinant poliovirus nucleic acids were analyzed. In this case, there was a clear increase in the levels of IgA anti-poliovirus antibodies in animals immunized via the intragastric, intrarectal, or intramuscular route at Day 14 and 45 post booster immunization. In FIGS. 10A and 10B, IgA anti-poliovirus antibodies from the vaginal lavage samples taken from mice immunized via the intrarectal or intramuscular route were analyzed. In this case, there was a clear increase over the preimmune values at Day 45 post booster immunization with animals immunized via the intrarectal route. In contrast, there was not a significant increase in the levels of IgA anti-poliovirus antibodies in animals immunized via the intramuscular route. Finally, as shown in FIGS. 11A, 11B, and 11C, IgA anti-poliovirus antibodies were present in extracts from feces obtained from animals immunized via the intragastric, intrarectal or intramuscular route. In all cases, there was an increase of the IgA anti-poliovirus antibodies at Day 21, Day 14 post booster immunization and Day 45 post booster immunization. Levels were approximately 5-fold over the pre-immune levels taken at Day 0. It is possible that the levels of anti-poliovirus detected have been underestimated due to the possibility that the animals are also shedding poliovirus in the feces at this time. The shed poliovirus as well as anti-poliovirus antibodies form an immune complex which would not be detected in the ELISA assay.

Anti-HIV-1-gag Antibodies

Portions of the same samples that were collected to analyze anti-poliovirus antibodies were analyzed for the presence of anti-HIV-1-gag-antibodies. FIGS. 12A, 12B, and 12C show the serum levels of total IgG (representing IgG as the major species and IgM and IgA as the minor species) anti-HIV-1-gag antibodies in the serum of animals immunized via the intragastric, intrarectal, or intramuscular route. No consistent increase in the levels of serum antibodies directed against HIV-1 -gag antibodies in animals immunized via the intragastric or intrarectal route was observed. This is represented by the fact that there was no increase in the levels above that observed at Day 0 (pre-immune) value. In contrast, there was an increase in the anti-HIV-1-gag antibodies levels in mice immunized via the intramuscular route. On Day 21 post immunization, there was a clear increase over the background value. The levels of anti-HIV-1-gag antibodies in the serum at Days 14 post boost and 45 post boost were clearly above the pre-immune values in the animals immunized via the intramuscular route.

In FIGS. 13A, 13B, and 13C, IgA anti-HIV-1-gag antibodies present in the saliva of animals immunized via the intragastric, intrarectal or intramuscular route. In this case, there was a clear increase over the pre-immune levels (Day 0) in animals immunized by all three routes of immunization. The highest levels of IgA anti-HIV-1-gag antibodies in the saliva were found at Day 45 post booster immunization. FIGS. 14A and 14B show a similar pattern for the samples obtained from vaginal lavage of animals immunized via the intrarectal or intramuscular route. In this instance, there was a clear increase at Days 14 and 45 post booster immunization in the levels of IgA anti-HIV-1-gag antibodies from animals immunized via the intrarectal route of immunization. The animals immunized via the intramuscular route exhibited an increase of IgA anti-HIV-1-gag antibodies in vaginal lavage samples starting at Day 12 through Day 21. The levels increased following the booster immunization at Day 21 resulting in the highest levels observed at Day 45 post booster immunization. In FIGS. 15A, 15B, and 15C, IgA anti-HIV-1 -gag antibodies present in fecal extracts obtained from animals immunized via the three different routes were analyzed. In general, there was an increase of the pre-immune levels using all three routes of immunization that was most evident at Days 14 and 45 post booster immunization. The results of these studies clearly establish that administration of the encapsidated recombinant HIV-1-poliovirus nucleic acids via the intragastric, intrarectal, or intramuscular route results in the generation of anti-HIV-1-gag antibodies in serum, saliva, vaginal lavage, as well as fecal extracts. A greater serum anti-HIV-1-gag antibody response was obtained by immunization of the animals via the intramuscular route rather than the intragastric or intrarectal routes. However, IgA anti-HIV-1-gag antibodies in secretions of animal immunized via all three routes were observed.

EXAMPLE 4

PRODUCTION OF ANTI-POLIOVIRUS ANTIBODIES IN PIGTAIL MACAQUE IMMUNIZED WITH ENCAPSIDATED RECOMBINANT POLIOVIRUS NUCLEIC ACID CONTAINING A PORTION OF THE HIV-1 GAG GENE

A pigtail macaque was immunized with $5\times10^8$ PFU of a virus stock of type I attenuated poliovirus containing the encapsidated recombinant nucleic acid from pT7IC-Gag #2 (FIG. 2 ). For these studies, intrarectal immunization was performed because of the high concentration of gut associated lymphoid tissue in the rectum of primates. The virus was deposited in a volume of 1 ml using a syringe filter with soft plastic tubing and inserted 1 inch into the rectum. The analysis of the anti-poliovirus and anti-gag antibodies was as described in Example 2 except that anti-monkey-specific reagents were substituted for anti-murine-specific reagents.

Serum from the macaque prior to immunization (Day 0), 12 days post primary immunization (12pp), 27 days post primary immunization (27pp) were collected. A second administration of virus consisting of 1 ml of $5 \times 10^8$ PFU given intrarectally and $2.5 \times 10^7$ PFU of virus administered intranasally at 27 days post primary immunization. Fourteen days after the second administration of virus (14 days post booster) serum was collected.

Figure 16:
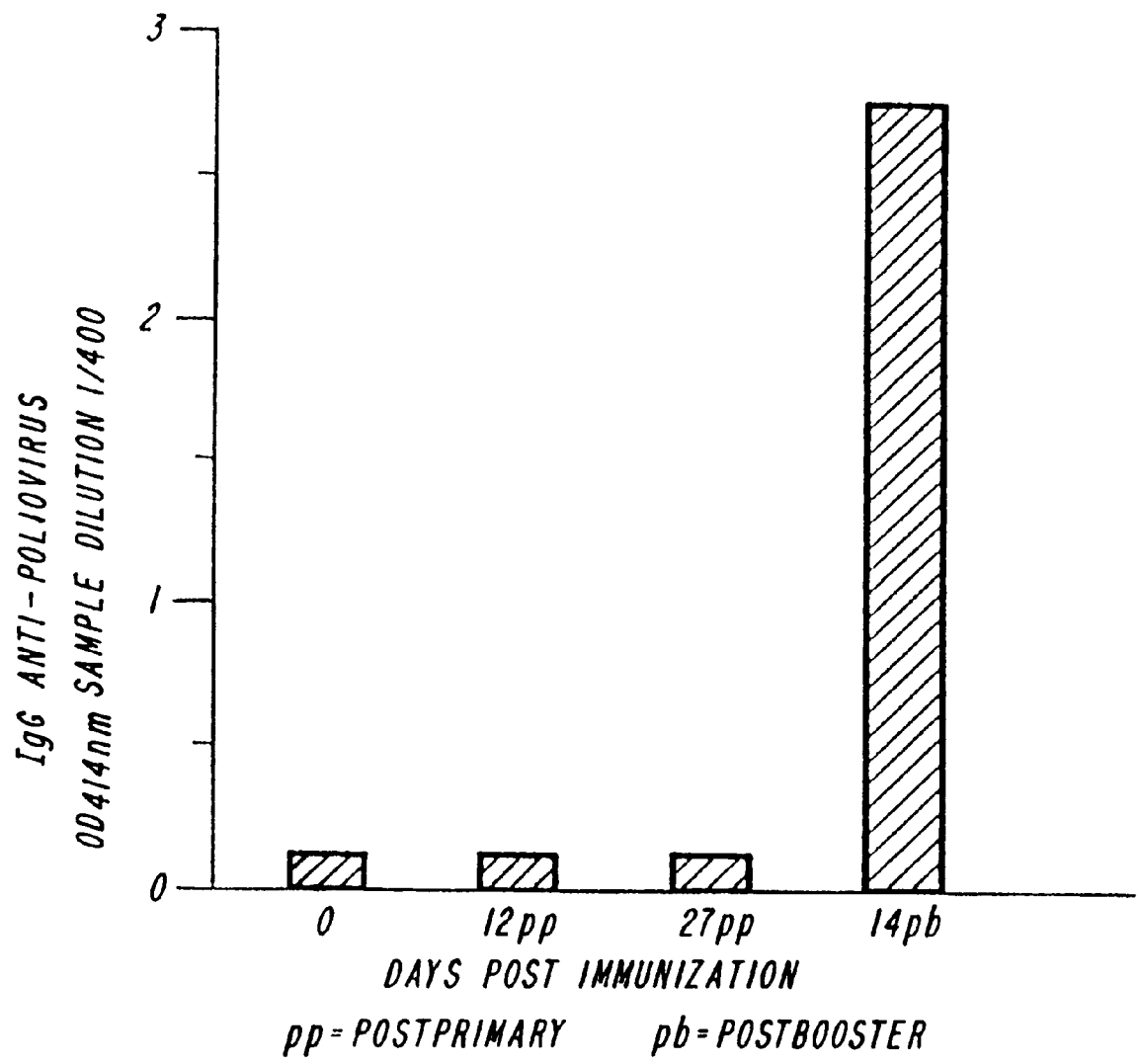

All serum samples were diluted 1:400 in PBS and the levels of IgG anti-poliovirus antibody were determined by ELISA as described above. As shown in FIG. 16, there was a clear increase in the serum IgG anti-poliovirus antibodies, as measured by $OD_{414}$ in the ELISA, in the immunized macaque at 14 days post booster immunization. The levels were approximately 10-fold higher than the previous levels (Day 0). This study shows that intrarectal primary followed by intrarectal-intranasal booster immunization results in clear increase in the IgG anti-poliovirus antibodies.

MATERIALS AND METHODS II:

The following materials and methods were used in Examples 5 and 6:

All chemicals were purchased from Sigma Chemical Company. Tissue culture media and supplements were purchased from Gibco/BRL Company. The [$^{35}$S] Translabel (methionine/cysteine) and methionine/cysteine-free DMEM were purchased from ICN Biochemicals. Restriction enzymes were obtained from New England Biolabs. The T7 RNA by the method of Grodberg and Dunn ((1988)*J. Bacteriol.* 170:1245–1253). Synthetic DNA primers were prepared at the University of Alabama Comprehensive Cancer Center facility or obtained from Cruachem, Fisher Co. Tri Reagent-LS was obtained from Molecular Research Center, Inc.

Tissue Culture Cells and Viruses

HeLa T4 and BSC-40 (African green monkey kidney/cell line derived from BSC 1 cells) cell monolayers were grown in Dulbecco's modified Eagle's medium (DMEM) supplemented with 5% fetal calf serum and 1×GMS-G supplement (complete medium). The stock of the poliovirus type 1 Mahoney was derived from transfection of an infectious cDNA clone of poliovirus obtained from B Semler, University of California at Irvine (Semler, B. L. et al. (1984)*Nucleic Acids Res.* 12:5123–5141). The stock of poliovirus type 1 Sabin was obtained from American Type Culture Collection. The recombinant vaccinia virus VV-P1, which expresses the poliovirus P1 capsid precursor protein upon infection, has also been previously described (Ansardi, D. C. et al. (1991) *J. Virol.* 65:2088–2092). Antisera (recombinant) to HIV-1 p25/24 Gag (Steimer, K. S. et al. (1986)*Virol.* 150:283–290) and a recombinant vaccinia virus vVK1(Karacostas, V. K. et al. (1989)*Proc. Natl. Acad. Sci.* (USA) 86:8964–8967), which expresses the $Pr55^{gag}$ protein upon infection, was obtained through the AIDS Research and Reference Reagent Program. The antisera to $3D^{pol}$ has been previously described (Jablonski, S. A. et al. (1991)*J. Virol.* 65:4565–4572).

Construction of Recombinant Poliovirus Nucleic Acid Containing the HIV-1 gag Gene To subclone the HIV-1 recombinant poliovirus genomes, modifications were made to the poliovirus cDNA plasmid pT7-IC, which contains the poliovirus cDNA, and has been described previously (Choi, W. S. et al. (1991)*J. Virol.* 65:2875–2883). A unique Sac I restriction site was generated at the 5' end of the P1 region in the plasmid pT7-IC by a conservative single base change at nucleotide 748 by site-directed mutagenesis to generate the plasmid pT7-IC-Sac I (Sambrook, J. et al. Molecular Cloning: A Laboratory Manual, 2nd ed. (Cold Spring Harbor Laboratory Press, Cold Spring harbor, New York, 1989). The mutation was confirmed by sequence analysis of ds DNA (Sambrook, J. et. al. Molecular Cloning: A Laboratory Manual, 2nd ed. (Cold Spring Harbor Laboratory Press, Cold Spring Harbor, New York, 1989). A unique SnaBI restriction site was then generated in the same plasmid by PCR, at nucleotide 3359, using the following synthetic DNA primers: 5'-CAC-CCC-TCT-CCT-ACG-TAA-CCA-AGG-ATC-3'(SEQ ID NO: 9), and 5'-GTA-CTG-GTC-ACC-ATA-TTG-GTC-AAC-3' (SEQ ID NO: 10). The amplified DNA fragment was precipitated and digested with SnaBI and BstEII. After digestion of the plasmid pT7-IC-Sac I with SnaBI and BstEII, the PCR fragment was ligated into the plasmid. The resultant plasmid was designated pT7-IC-Sac I-SnaBI.

To construct recombinant poliovirus nucleic acid which contains the complete HIV-1 $Pr55^{gag}$ gene, nucleotides 345 to 1837 were amplified from the plasmid pHXB2 (Ratner, L. et al. (1985)*Nature* 313:277–284) by PCR using the following DNA primers: 5'-GGA-GAG-AGA-TGG-GAG-CTC-GAG-CGT-C-3'(SEQ ID NO: 11), and 5'-GCCCCC-CTA-TAC-GTA-TTG-TG-3'(SEQ ID NO: 12). The DNA fragment was ligated into the plasmid pT7-IC-Sac I-SnaBI after digestion of the fragment DNA and pT7-IC-Sac I-SnaBI with Sac I and SnaBI DNA sequencing confirmed that the translational reading frame was maintained between the foreign gene and poliovirus. The final construct was designated as pT7-IC-$Pr55^{gag}$.

A second recombinant poliovirus nucleic acid containing the HIV-1 gag gene was constructed to position nucleotides 1–949 of the poliovirus genome 5' to the HIV-1 gag gene. The following primers were designed to amplify a DNA fragment from the plasmid pT7-IC from a unique EcoRI site, located upstream of the T7 RNA polymerase promoter, to nucleotide 949: 5'-CCA-GTG-AAT-TCC-TAA-TAC-GAC-TCA-CTA-TAG-GTT-AAA-ACA-GC-3'(SEQ ID NO: 13) and 5'-CTC-TAT-CCT-GAG-CTCCAT-ATG-TGT-CGA-GCA-GTT-TTT-GGT-TTA-GCA-TTG-3'(SEQ ID NO: 14). The primers were designed to include a 2A protease cleavage site (tyrosine-glycine amino acid pair (underlined) preceded by six wild-type amino acids: Thr-Lys-Asp-Leu-Thr-Thr-Tyr-Gly) (SEQ ID NO: 15), corresponding to the authentic 2A cleavage site in the $3D^{pol}$ gene at nucleotide 6430 in the poliovirus genome, followed by a Sac I restriction site at the 3' end of the VP4 gene in the amplified fragment. The DNA fragment was ligated into pT7-IC-$Pr55^{gag}$ after digestion with EcoRI and Sac I. The final construct was designated pT7-IC-$Pr55^{gag}$(VP4/2A).

The construction and characterization of the pT7-IC-Gag 1 has been described in previous studies (Choi, W. S. et al. (1991)*J. Virol.* 65:2875–2883; Porter, D. C. et al. (1993)*J. Virol.* 67:3712–3719). Briefly, pT7-IC-Gag 1 was constructed by substitution of nucleotides 718 to 1549 of the HIV-1 gag gene (amplified using PCR) for the P1 coding region between nucleotides 1174 and 2470 in the infectious cDNA plasmid pT7-IC. This substitution encompasses most of the VP2 and VP3 capsid sequences while maintaining the VP4 and VP1 coding regions.

Encapsidation and Serial Passage of Recombinant Poliovirus Nucleic Acid Containing the HIV-1 Gag Gene The encapsidation and serial passage of recombinant poliovirus nucleic acid using VV-P1 has been previously described (Morrow, C.D. et al. (1994) "New Approaches for Mucosal Vaccines for AIDS: Encapsidation and Serial Passage of Poliovirus Replicons that Express HIV-1 Proteins Upon Infection" *AIDS Res. and Human Retroviruses* 10(2); Porter, D.C. et al. (1993)*J. Virol.* 67:3712–3719). Briefly, HeLa T4 cells were infected with 5 PFU/cell of VV-P1, which expresses the poliovirus capsid precursor protein P1. At 2 hours post-infection, the cells were transfected using the DEAE-Dextran method with RNA transcribed from the chimeric genomes in vitro as previously described (Choi, W. S. et al. (1991)*J. Virol.* 65:2875–2883; Pal-Ghosh, R. et al. (1993)*J. Virol.* 67:4621–4629; Porter, D.C. et al. (1993)*J. Virol.* 67:3712–3719). The cultures were harvested at 24 hours post-transfection by detergent lysis, overlaid on a 30% sucrose cushion (30% sucrose, 30 mM Tris pH 8 0, 1% Triton X-100, 0.1 M NaCI), and centrifuged in a Beckman SW55Ti rotor at 55,000 rpms for 1.5 hours (Ansardi, D. C. et al. (1993)*J. Virol.* 67:3684–3690; Porter, D.C. et al. (1993)*J. Virol.* 67:3712–3719). The supernatant was discarded and the pellet washed under the same conditions in a low salt buffer (30mM Tris pH 8.0, 0.1 M NaCl) for an additional 1.5 hours. The pellets were then resuspended in complete DMEM and used for serial passage immediately or stored at −70° C. until used.

For serial passage of the encapsidated recombinant poliovirus nucleic acid and generation of virus stocks, BSC-40 cells were first infected with 10–20 PFU/cell of VV-P1. At 2 hours post-infection, the cells were infected with passage 1 of the encapsidated recombinant poliovirus nucleic acid. The cultures were harvested at 24 hours post-infection by three successive freeze/thaws, sonicated, and clarified by low speed centrifugation at 14,000×g for 20 minutes. The supernatants were then stored at −70° C. or used immediately for additional passages following the same procedure.

Metabolic Labeling and Immunoprecipitation of Viral Proteins from Infected Cells To metabolically label proteins from infected cells, the cultures were starved for methionine/cysteine at the times indicated post-infection by incubation in DMEM minus methionine/cysteine for 30 minutes. At the end of this time, [$^{35}$S] Translabel was added for an additional one hour. Cultures were then processed for immunoprecipitation of viral proteins by lysing the cells with RIPA buffer (150 mM NaCI, 10 mM Tris pH 7.8, 1% Triton X-100, 1% sodium deoxycholate, 0.2% sodium dodecyl sulfate). Following centrifugation at 14,000×g for 10 minutes, the designated antibodies were added to the supernatants which were then incubated at 4° C. for 24 hours. The immunoprecipitates were collected by addition of 100μl protein A-Sepharose (10% weight/volume in RIPA buffer). After a 1 hour incubation at room temperature, the protein A-Sepharose beads were collected by brief centrifugation and washed 3 times with RIPA buffer. The bound material was eluted by boiling 5 minutes in gel sample buffer (62.5 mM Tris pH 6.8, 2% SDS, 20% glycerol, 0.05% bromophenol blue, and 0.7M 13-mercaptoethanol). The proteins were analyzed by SDS-polyacrylamide gel electrophoresis and radiolabeled proteins were visualized by fluorography using sodium salicylate as previously described (Ansardi, D. C. et al. (1993)*J. Virol.* 67:3684–3690; Porter, D.C. et al. (1993)*J. Virol.* 67:3712–3719). The immunoprecipitated proteins were quantitated by phosphorimagery where indicated (Molecular Dynamics).

Nucleic Acid Hybridization of RNA

Total cellular RNA was prepared from cells transfected with equivalent amounts of in vitro transcribed RNA as described by the manufacturer using Tri Reagent-LS (Molecular Research Center, Inc.). The amounts of full length RNA transcripts were estimated by agarose gel electrophoresis prior to transfection (Choi, W. S. et al. (1991)*J. Virol.* 65:2875–1883). The RNA was then denatured, separated on a formaldehyde-1.0% agarose gel, and transferred from the gel to a nitrocellulose filter by capillary action. Equivalent amounts of RNA, as measured by levels of rRNA, were loaded into each lane of the gel. For analysis of encapsidated recombinant poliovirus RNA, the RNA was isolated from virions (Ricco-Hesse, R. M. et al. (1987)*Virol.* 160:311–322) which had been concentrated through a sucrose cushion as previously described (Ansardi, D. C. et al. (1993)*J. Virol.* 67.3684–3690; Porter, D. C. et al. (1993)*J. Virol.* 67:3712–3719). The RNA was denatured and spotted onto nitrocellulose using a dot blot apparatus according to established protocols (Sambrook, J. et al. Molecular Cloning: A Laboratory Manual, 2nd ed. (Cold Spring Harbor Laboratory Press, Cold Spring Harbor, New York, 1989). The RNA was immobilized onto the nitrocellulose by baking in a vacuum oven at 80° C. for 1 hour.

The conditions for prehybridization, hybridization and washing of RNA immobilized onto nitrocellulose were as described previously (Choi, W. S. et al. (1991)*J. Virol.* 65:2875–2883; Pal-Ghosh, R. et al. (1993)*J. Virol.* 67:4621–4629; Porter, D.C. et al. (1993)*J. Virol.* 67:3712–3719). Briefly, the blot was prehybridized in hybridization buffer (50% deionized formamide, 6×SSC, 1% SDS, 0.1% Tween 20, and 100 μg/mL yeast tRNA). The blot was then incubated in hybridization buffer containing 1×10$^6$ cpm/mL of a [$^{32}$p] labeled riboprobe complementary to nucleotides 671–1174 of the poliovirus genome (Choi, W. S. et al. (1991)*J. Virol.* 65:2875–2883; Pal-Ghosh, R. et al. (1993)*J. Virol.* 67:4621–4629; Porter, D. C. et al. (1993)*J. Virol.* 67:3712–3719). After hybridization, the blot was washed two times with 0.1×SSC/ 0.1 % SDS at room temperature and at 65° C. The blot was then exposed to X-ray film with an intensifying screen. The levels of RNA from each sample were quantitated by phosphorimagery (Molecular Dynamics).

Passage of Recombinant Poliovirus Nucleic Acid Containing the HIV-1 Gag Gene with Type I Attenuated Poliovirus Virus stocks of encapsidated recombinant poliovirus nucleic acid containing HIV-1 gag gene were serially passaged with wild-type poliovirus as previously described (Morrow, C. D. et al. (1994) "New Approaches for Mucosal Vaccines for AIDS: Encapsidation and Serial Passage of Poliovirus Replicons that Express HIV-1 Proteins Upon Infection" *AIDS Res. and Human Retroviruses* 10(2); Porter, D. C. et al. (1993)*J. Virol.* 67:3712–3719). Briefly, BSC-40 cells were co-infected with 10 PFU/cell of type 1 Sabin poliovirus and a virus stock of encapsidated recombinant poliovirus nucleic acid at pass 21. The infected cells were harvested at 24 hours post-infection by three successive freeze/thaws, sonicated, and clarified by low speed centrifugation. Approximately one-half of the supernatant was used for serial passaging by re-infection of BSC-40 cells. After 24 hours, the cultures were harvested as described above and the procedure was repeated for an additional 2 serial passages.

EXAMPLE 5

CONSTRUCTION, EXPRESSION, AND REPLICATION OF RECOMBINANT POLIOVIRUS NUCLEIC ACIDS CONTAINING THE ENTIRE HIV-1 GAG GENE

Figure 17A:
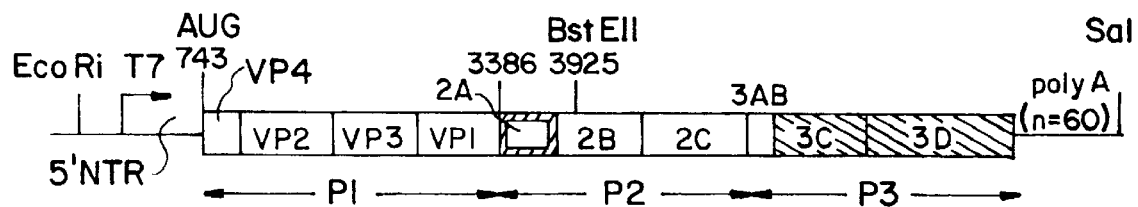
Figure 17B:
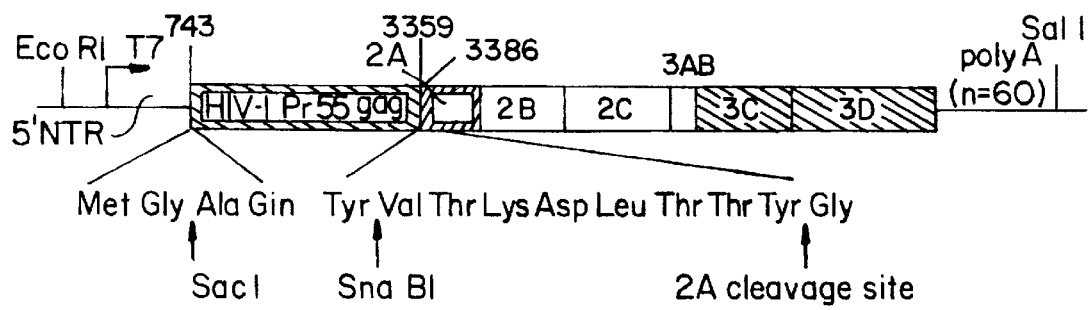
Figure 17C:
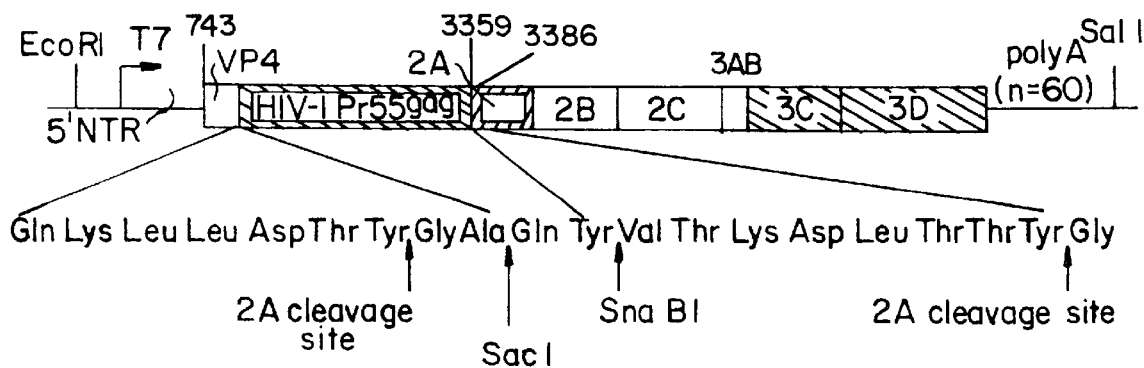
Figures 19A, 19B:
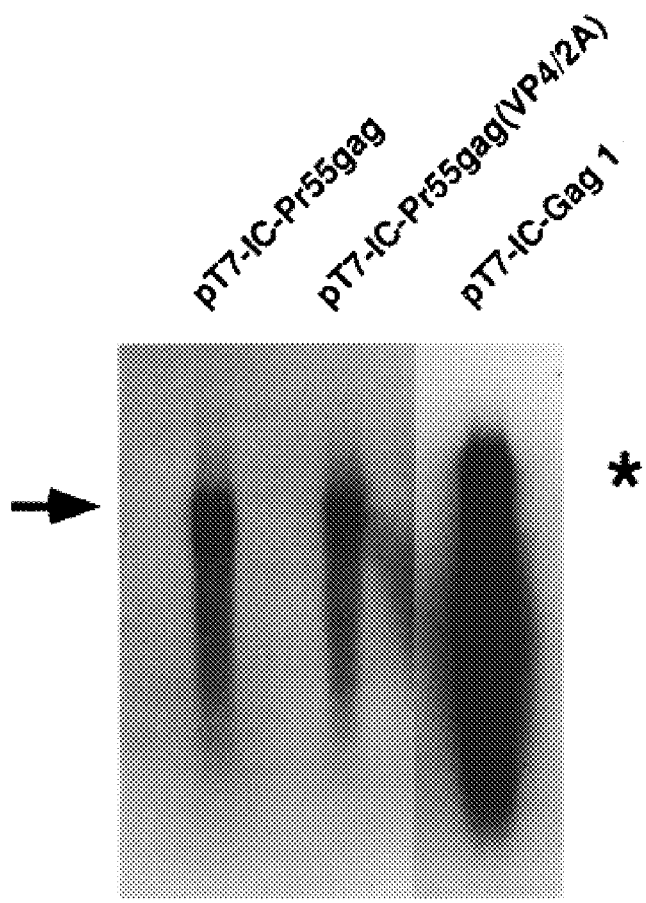
Figure 20:
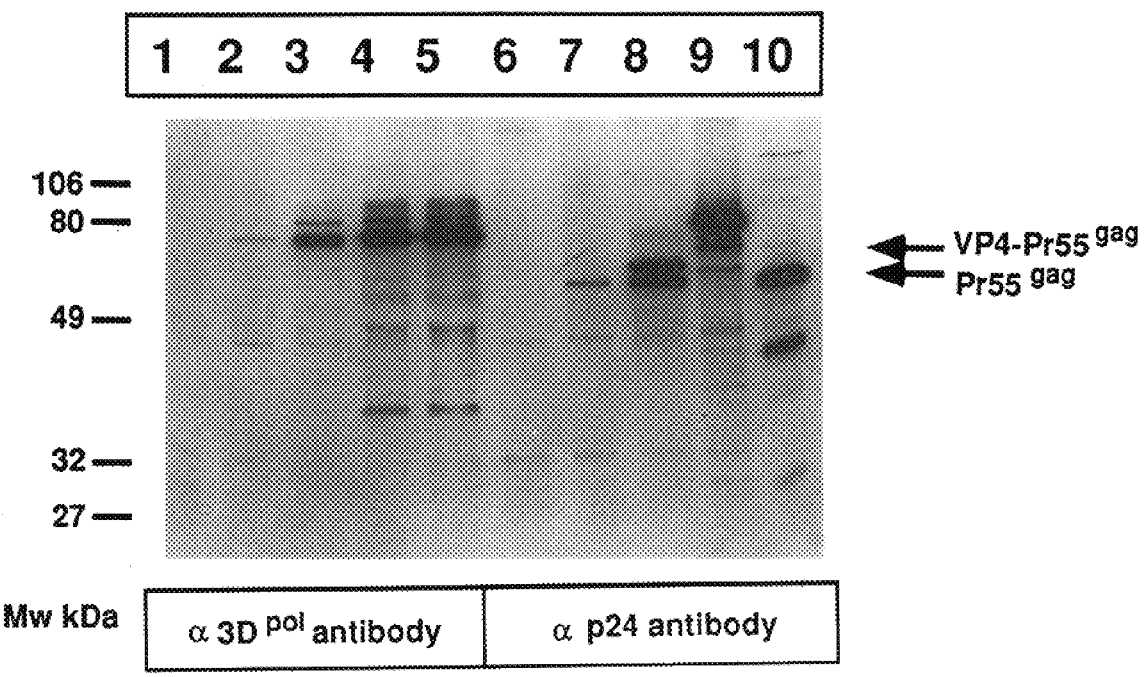
Figure 21:
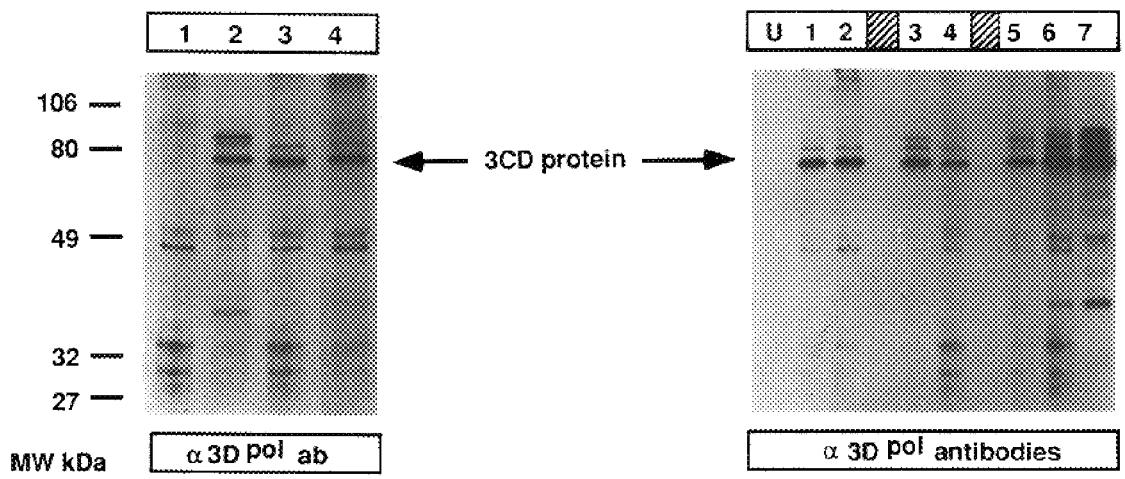

To further define the requirements of the P1 region for the replication and encapsidation of poliovirus RNA, the complete gag gene of HIV-1 was substituted for the P1 capsid coding sequences. For these studies the plasmid pT7-IC (FIG. 17A), which contains the promoter sequences for T7 RNA polymerase positioned 5' to the complete poliovirus cDNA, was used (Choi, W. S. et al. (1991)*J. Virol.* 65:2875–2883). A unique Sal I restriction site is located after the poly (A) tract that can be used to linearize the cDNA before in vitro transcription; the RNA transcripts from this cDNA are infectious upon transfection into tissue culture cells (Choi, W. S. et al. (1991)*J. Virol.* 65:2875–2883). In order to substitute the entire P1 capsid region with the HIV-1 gag gene, a unique Sac I restriction site was generated at nucleotide 748, immediately following the translational start site of poliovirus. A unique SnaBI restriction site was generated at nucleotide 3359, which is positioned eight amino acids prior to the 2A protease cleavage site (tyrosine-glycine) located at nucleotide 3386; previous studies have suggested a requirement for the amino acid at the P4 position for autocatalytic processing of the polyprotein by the 2A protease (Harris, K. et al. (1990)*Sem. in Virol.* 1:323–333). The resultant plasmid, pT7-IC-Sac I-SnaBI was then used for insertion of the HIV-1 gag gene. pT7-IC-Pr55$^{gag}$ (FIG. 17B) was constructed by insertion of the complete HIV-1 gag gene from nucleotides 345 to 1837; the Sac I and SnaBI restriction sites were introduced at the 5' and 3' ends of the gene. Substitution of the entire P1 region from the translational start site of poliovirus to the 2A protease (3386), which autocatalytically cleaves from the polyprotein upon translation (Toyoda, H. et al. (1986)*Cell* 45:761–770), results in expression of Pr55$^{gag}$ protein after proteolytic processing of the polyprotein.

Naturally occurring defective interfering (DI) genomes of poliovirus contain heterologous deletions of the P1 coding region that encompass the VP3, VP3 and VP2 capsid sequences. All known poliovirus Dl genomes maintain an intact VP4 coding region (Kuge, S. et al. (1986)*J. Mol. Biol.* 192:473–487). A second recombinant poliovirus nucleic acid was generated in which the gag gene was substituted in frame for the VP2, VP3 and VP1 capsid sequences, from nucleotides 949 to 3359 to maintain the VP4 coding region. For this construct, a DNA fragment was amplified by PCR from the plasmid pT7-IC containing sequences encoding VP4 followed by the codons for eight amino acids containing a tyrosine-glycine amino acid pair. Substitution of the EcoRI to Sac I fragment into pT7-IC-Pr55$^{gag}$ results in the final plasmid, pT7-IC-Pr55$^{gag}$ (VP4/2A), which contains the VP4 coding sequences fused in-frame at the 5' end of the complete gag gene (FIG. 17C). In each construct, the insertion of HIV-1 gag gene sequences maintains the translational reading frame with poliovirus.

Poliovirus and HIV-1-specific protein expression from the recombinant poliovirus nucleic acids which contain the HIV-1 gag gene was analyzed after transfection of recombinant poliovirus RNA into cells which had been previously infected with VV-P1 (FIGS. 18A and 18B). Briefly, Cells were infected with VV-P1 at a multiplicity of infection of 5. At 2 hours post infection, the cells were transfected with RNA derived from in vitro transcription of the designated plasmids. Cells were metabolically labeled, and cell extracts were incubated with the antibodies indicated and immunoreactive proteins were analyzed on SDS-polyacrylamide gels: (FIG. 18A) Lane 1, mock-transfected cells; Lane 2, cells transfected with RNA derived from pT7-IC-Pr55$^{gag}$; Lane 3, cells transfected with RNA derived from pT7-IC-Pr55$^{gag}$ (VP4/2A); Lane 4, cells transfected with RNA derived from pT7-IC-Gag 1; Lane 5, cells infected with type 1 Mahoney poliovirus at a multiplicity of infection of 30. (FIG. 18B): Lane 1, mock-transfected cells; Lane 2, cells transfected with RNA derived from pT7-IC-Pr55$^{gag}$; Lane 3, cells transfected with RNA derived from pT7-IC-Pr55$^{gag}$(VP4/2A); Lane 4, cells infected with vVK1 at a multiplicity of infection of 10; Lane 5, cells transfected with RNA derived from pT7-IC-Gag 1. The molecular mass standards and positions of relevant proteins are indicated.

Under the conditions for metabolic labeling, the 3CD protein, which is a fusion between the 3C$^{pro}$ and 3D$^{pol}$ proteins, is the predominant 3D containing viral protein detected from poliovirus-infected cells (Porter, D. C. et al (1993)*Virus. Res.* 29:241–254). A protein with an approximate molecular mass of 72 kDa, corresponding to the 3CD protein of poliovirus, was detected from cells transfected with RNA from pT7-IC-Pr55$^{gag}$ and pT7-IC-Pr55$^{gag}$(VP4/2A) (FIG. 18A, lanes 2 and 3), but not from mock-transfected cells (FIG. 18A, lane 1). The 3CD protein was also immunoprecipitated from cells transfected with RNA derived from pT7-IC-Gag 1 (FIG. 18A, lane 4), which was used as a positive control for transfections in these studies (Porter, D. C. et al. (1993)*J. Virol.* 3712–3719).

For analysis of the expression of HIV-1 Gag protein, the extracts were incubated with antip25/24 antibodies (FIG. 18B). A lysate from cells infected with the recombinant vaccinia virus vVK1, which contains the HIV-1 gene sequences encoding the complete gag and pol genes, was used as a control for Pr55$^{gag}$ protein expression (Karacostas, V. K. et al. (1989)*Proc. Natl. Acad. Sci.* (USA) 86:8964–8967). A protein with an apparent molecular mass of 55 kDa that co-migrated with protein immunoprecipitated from cells infected with vVK1 (FIG. 18B, lane 4) was detected from cells transfected with RNA from pT7-IC-Pr55$^{gag}$ and pT7-IC-Pr55$^{gag}$(VP4/2A) (FIG. 18B, lanes 2 and 3). In addition, a protein of higher molecular mass was immunoprecipitated from cells transfected with RNA from pT7-IC-Pr55$^{gag}$(VP4/2A) (FIG. 18B, lane 3). This protein probably is a VP4-Pr55$^{gag}$ precursor protein.

The replication of the transfected RNA derived from the recombinant poliovirus nucleic acid was also analyzed by Northern blot (FIGS. 19A and 19B). HeLa T4 cells were transfected with RNA transcribed in vitro from pT7-IC-Pr55$^{gag}$, pT7-IC-Pr55$^{gag}$(VP4/2A) pT7-IC-Gag 1. At 9 hours postransfection, total cellular RNA was prepared, separated in a 1% formaldehyde-agarose gel, blotted onto nitrocellulose and analyzed using a riboprobe complementary to nucleotides 671–1174 of the poliovirus genome. (Choi, W. S. et al. (1991) *J. Virol.* 65:2875–2883; Pal-Ghosh, R. et al. (1993)*J. Virol.* 67:4621–4629; Porter, D. C. et al. (1993)*J. Virol.* 67:3712–3719) (FIG. 19A) The order of the samples is indicated. The migration of RNA of the predicted size, which Was derived from in vitro transcription of pT7IC-Pr55$^{gag}$ and pT7-IC-Pr55$^{gag}$(VP4/2A), is indicated by an arrow. The asterisk indicates the migration of RNA of the expected size which was derived from pT7-IC-Gag 1(Porter, D. C. et al. (1993)*J. Virol.* 67:3712–3719). Thc radioactivity of the Northern blot was quantitated using phosphorimagery.

The migration of RNA from pT7-IC-Pr55$^{gag}$ and pT7-IC-Pr55$^{gag}$(VP4/2A) transfected cells was slightly faster on the formaldehyde-agarose gel than RNA from pT7-IC-Gag 1, which is consistent with the predicted 6.3–6.4 kb size for RNA from pT7-IC-Pr55$^{gag}$ and pT7-IC-Pr55$^{gag}$(VP4/2A) versus the 7.0 kb size for RNA from pT7-IC-Gag 1(FIG. 19A). Quantitation of the major bands of radioactivity from each sample by phosphorimagery indicated that the values for pT7-IC-Pr55$^{gag}$ and pT7-IC-Pr55$^{gag}$(VP4/2A) were similar although the amounts of RNA detected from both recombinant poliovirus nucleic acids were lower than that for RNA obtained from pT7-IC-Gag 1 (FIG. 19B). Together, these results demonstrate that the RNA from pT7-IC-Pr55$^{gag}$ and pT7-IC-Pr55$^{gag}$(VP4/2A) replicate to similar levels in transfected cells.

EXAMPLE 6

ENCAPSIDATION AND SERIAL PASSAGE OF RECOMBINANT POLIOVIRUS NUCLEIC ACID CONTAINING THE ENTIRE HIV-1 GAG GENE

Cells were infected with VV-P1 and then transfected with RNA transcribed in vitro from pT7-IC-Pr55$^{gag}$, pT7-IC-Pr55$^{gag}$(VP4/2A) and pT7-IC-Gag 1. The encapsidated recombinant poliovirus genomes were passaged in cells which had been previously infected with VV-P1 for a total of 21 serial passes. Consistent with the nomenclature used herein, the encapsidated virus stocks of pT7-IC-Pr55$^{gag}$ and pT7-IC-Pr55$^{gag}$(VP4/2A) are referred to as vIC-Pr55$^{gag}$ and vIC-Pr55$^{gag}$(VP4/2A), respectively.

For analysis of poliovirus and HIV-1-specific protein expression, pass 21 virus stocks of encapsidated recombinant poliovirus nucleic acid were used to infect cells. After metabolic labeling, lysates from the cells were incubated with anti-3D$^{pol}$ and anti-p24 antibodies (FIG. 20). With reference to FIG. 20, cells were transfected with RNA derived from in vitro transcription of the designated plasmids at 2 hours post-infection with VV-P1. Encapsidated genomes were harvested from cells as described in Materials and Methods 11 and used to re-infect cells which had been previously infected with VV-P1. The encapsidated recombinant poliovirus genomes were subsequently serially passaged in VV-P1-infected cells for 21 serial passes. Cells were infected with virus stocks at pass 21 and metabolically labeled. Cell lysates were incubated with the designated antibodies and immunoreactive proteins were analyzed SDS-polyacrylamide gel; Lanes 1 and 6, mock-infected cells; Lanes 2 and 7, cells infected with vIC-Pr55$^{gag}$; Lanes 3 and 8, cells infected with vIC-Pr55$^{gag}$(VP4/2A); Lanes 4 and 9, cells infected with vIC-Gag1; Lane 5, cells infected with type 1 Mahoney poliovirus; Lane 10, cells infected with vVK1. The molecular mass standards and positions of relevant proteins are indicated.

Although the 3CD protein was detected from each of the recombinant poliovirus nucleic acid virus stocks, decreased levels of 3CD protein were consistently detected from cells infected with virus stocks of vIC-Pr55$^{gag}$(FIG. 20, lane 2) as compared to cells infected with virus stocks of vIC-Pr55$^{gag}$ (VP4/2A) (FIG. 20, lane 3) and vIC-Gag 1(FIG. 20, lane 4). Upon incubation of the lysates with anti-p24 antibodies, a protein with an apparent molecular mass of 55 kDa was detected from the vIC-Pr55$^{gag}$(FIG. 20, lane 7) and vIC-Pr55$^{gag}$(VP4/2A) (FIG. 20, lane 8) virus stocks; this protein co-migrated with Pr55$^{gag}$ expressed from cells infected with the recombinant vaccinia virus vVK1(FIG. 20, lane 10) (Karacostas, V. et al. (1989)*Proc. Natl. Acad. Sci.* (USA) 86:8964–8967). Again, infection of cells with the vIC-Pr55$^{gag}$(VP4/2A) virus stock resulted in an increased level of the 55 kDa protein, compared to cells infected with vIC-Pr55$^{gag}$. Consistent with previous studies, vIC-Gag 1 expressed an 80 kDa Gag-P1 fusion protein in infected cells (FIG. 20, lane 9) (Porter, D. C. et al. (1993)*J. Virol.* 67:3712–3719).

Since it has been demonstrated that after transfection that RNA from each of the recombinant poliovirus nucleic acids resulted in similar levels of replication and protein expression, detection of reduced levels of protein expression from cells infected with vIC-Pr55$^{gag}$ as compared to vIC-Pr55$^{gag}$(VP4/2A) could be the result of a difference in infectivity (i.e., interaction with receptor, uncoating) between the recombinant poliovirus nucleic acids. To address this question, RNA was isolated from equivalent amounts of vIC-Pr55$^{gag}$ and vIC-Pr55$^{gag}$ (VP4/2A) virus stocks, which had been serially passaged with VV-P1 for 21 passes. Serial dilutions of the RNA were then spotted onto nitrocellulose and analyzed using a riboprobe as described in Materials and Methods 11. Quantitation of the radioactivity from each sample by phosphorimagery indicated values from vIC-Pr55$^{gag}$(VP4/2A) virus stocks which were approximately 15 times higher than the values obtained for RNA from vIC-Pr55$^{gag}$. The results of these studies corroborate the differences in expression of 3CD and HIV-1 Gag protein observed for the recombinant poliovirus nucleic acids. To address the possibility that the recombinant poliovirus nucleic acids might have differences in infectious potential, cells were infected with equivalent amounts of encapsidated recombinant poliovirus nucleic acids, as determined by RNA hybridization, and metabolically labeled followed by immunoprecipitation with anti-3D$^{pol}$ antibodies (FIG. 1A). Equivalent amounts of a 72 kDa protein, corresponding to the 3CD protein, were detected from each of the recombinant poliovirus nucleic acid virus stocks. Quantitation of the radioactivity from each sample by phosphorimagery confirmed that the levels of 3CD were similar.

With reference to FIG. 21A, cells were infected with normalized amounts of encapsidated poliovirus nucleic acid virus stocks and metabolically labeled. Cells lysates were incubated with the designated antibodies and immunoreactive proteins were analyzed on an SDS-polyacrylamide gel: Lane 1, mock infected cells; Lane 2, cells infected with vIC-Pr55$^{gag}$ recombinant poliovirus stock; Lane 3, cells infected with vIC-Pr55$^{gag}$(VP4/2A) recombinant poliovirus stock; Lane 4, cells infected with vIC-Gag1 recombinant poliovirus stock. With reference to FIG. 21B, equivalent amounts of each of the recombinant poliovirus stocks were serially passaged in VV-P1-infected cells for 2 passes as described in Materials and Methods II. Cells were infected with material derived from passes I and 2 and metabolically labeled. Cells lysates were incubated with the designated antibodies and immunoreactive proteins were analyzed on an SDS-polyacrylamide gel; Lane U, mock-infected cells; Lane 1, cells infected with material from pass 1 of vIC-Pr55$^{gag}$ with VV-P1; Lane 3 cells infected with material from pass 1 of vIC-Pr55$^{gag}$(VP4/2A) with VV-P1; Lane 4, cells infected with material from pass 2 of vIC-Pr55$^{gag}$(VP4/2A) with VV-P1; Lane 5, cells infected with material from pass 1 of vIC-Gag 1 with VV-P1; Lane 6, cells infected with material from pass 2 of vIC-Gag 1 with VV-P1; Lane 7, cells infected with type 1 Mahoney poliovirus. The molecular mass standards and positions of relevant proteins are indicated.

To determine whether the decreased levels of RNA isolated from the vIC-Pr55$^{gag}$ virus stock at pass 21 as compared to the vIC-Pr55$^{gag}$(VP4/2A) and vIC-Gag 1 virus stocks were attributable to differences in the efficiency of encapsidation of RNA which contains the VP4 coding sequences versus the encapsidation of RNA which has a complete deletion of the P1 region, cells which had been previously infected with VV-P1 were infected with normalized amounts of each of the encapsidated recombinant poliovirus nucleic acid virus stocks. After 24 hours, complete cell lysis had occurred and the supernatant was processed as described in Materials and Methods II; one additional passage was performed in cells previously infected with VV-P1. For analysis of protein expression from the serially passaged material, cells were infected with material from passages 1 and 2, metabolically labeled, and the cell lysates were incubated with anti-3D$^{pol}$ antibodies (FIG. 21B). Similar amounts of the 3CD protein were detected from each of the passages of equivalent amounts of vIC-Pr55$^{gag}$(FIG. 21B, lanes 1 and 2), vIC-Pr55$^{gag}$(VP4/2A) (FIG. 21B, lanes 3 and 4) and vIC-Gag 1 recombinant poliovirus nucleic acid virus stocks (FIG. 21B, lanes 5 and 6) with VV-P1. Thus, the reduced levels of RNA and 3CD protein expression detected from the vIC-Pr55$^{gag}$ recombinant poliovirus nucleic acid virus stocks as compared to vIC-Pr55$^{gag}$(VP4/2A) and vIC-Gag 1 after 21 serial passes with VV-P1 (FIG. 20) were not apparent after passage of the recombinant poliovirus nucleic acids with VV-P1 for 2 serial passes.

Figure 22:
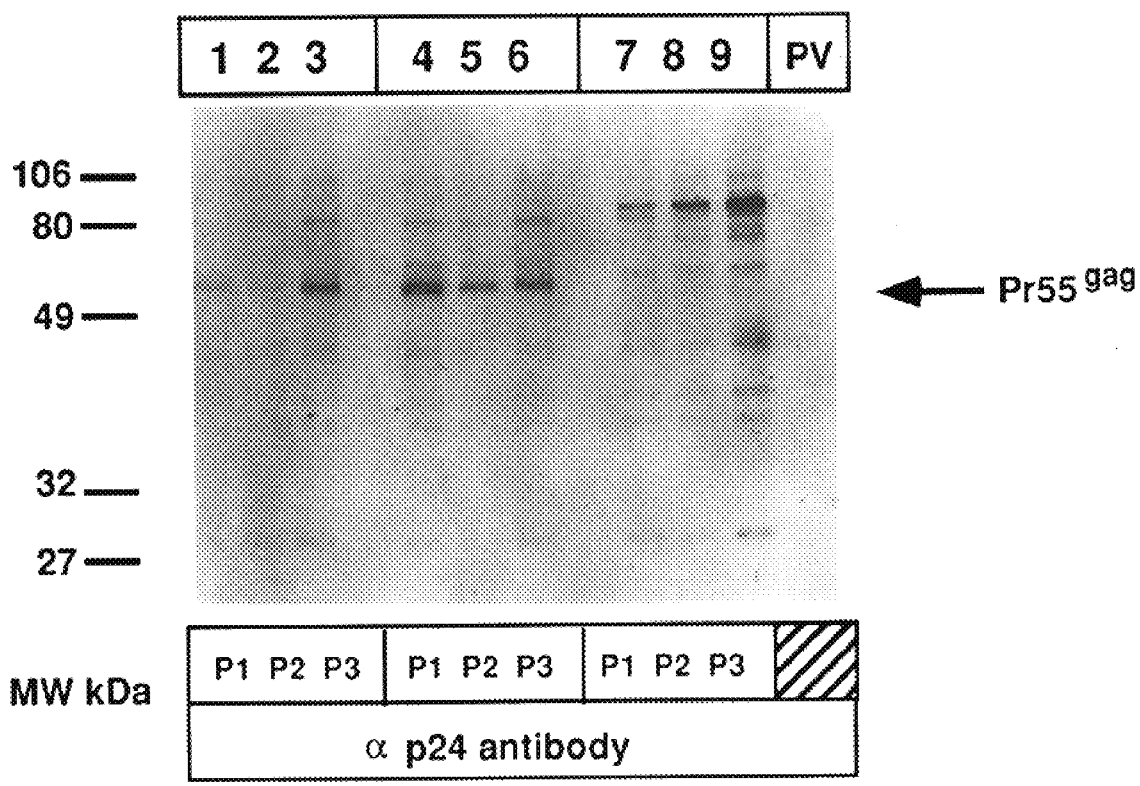

Since all known DIs of poliovirus contain an intact VP4 coding region, it was examined whether the recombinant poliovirus nucleic acid which contains the VP4 coding sequences might have an advantage if the recombinant poliovirus nucleic acid had to compete with the wild type genome for capsid proteins. To determine whether vIC-Pr55$^{gag}$ and vIC-Pr55$^{gag}$(VP4/2A) could also be maintained upon passage with wild-type poliovirus, cells were co-infected with equal amounts of either the vIC-Pr55$^{gag}$, vIC-Pr55$^{gag}$ (VP4/2A) or vIC-Gag 1 and type 1 Sabin poliovirus. After 24 hours, complete cell lysis had occurred and the supernatant was processed as described in Materials and Methods II; two additional passages were performed. Cells were infected with material from each serial passage, metabolically labeled and the cell extracts were incubated with antibodies to p24/25 protein (FIG. 22). With reference to FIG. 22, cells were co-infected with equal amounts of either the vIC-Pr55$^{gag}$, vIC-Pr55$^{gag}$ (VP4/2A) or vIC-Gag 1 and type 1 Sabin poliovirus. The cells were harvested at 24 hours post-infection and the supernatant was processed as described in Materials and Methods II; two additional passages were performed. Cells were infected from each of the serial passages and metabolically labeled. The cell lysates incubated with the designated antibody and immunoreactive proteins were analyzed on an SDS-polyacrylamide gel: Lane U, uninfected cells; Lanes 1, 2 and 3, cells infected with material derived from the indicated passes of vIC-Pr55$^{gag}$ with type 1 Sabin poliovirus; Lanes 4, 5 and 6, cells infected with material derived from the indicated passes of vIC-PR55$^{gag}$(VP4/2A) with type 1 Sabin poliovirus; Lanes 7, 8 and 9, cells infected with material derived from the indicated passes of vIC-Gag 1 with type 1 Sabin poliovirus; Lane PV, cells infected with type 1 Sabin poliovirus.

Each passage is denoted as follows: P1, pass 1; P2, pass 2; and P3, pass 3. The molecular mass standards and positions of relevant proteins are indicated.

No HIV-1-specific protein was cells infected with type 1 Sabin poliovirus alone (FIG. 22, lane PV); the 80 kDa gag-P1 fusion protein was detected from cells infected with material from passages 1, 2 and 3 of the vIC-Gag 1 recombinant poliovirus nucleic acid and wild-type poliovirus (FIG. 22, lanes 7–9) (Porter, D. C. et al. (1993)*J. Virol.* 67:3712–3719).

Upon serial passage of vIC-Pr55$^{gag}$(FIG. 22, lanes 1–3) and vIC-Pr55$^{gag}$(VP4/2A) (FIG. 22, lanes 4–6) virus stocks with type 1 Sabin, a protein which migrated at approximately 55 kDa was detected from cells infected with material from passages 1, 2, and 3. There was no consistent difference detected between the levels of Pr55$^{gag}$ expression from either recombinant poliovirus nucleic acid. Thus, the presence or absence of the VP4 coding region did not effect the capability of the recombinant poliovirus nucleic acid to compete with the wild-type poliovirus genomes for the P1 protein that was evident after three serial passages.

The construction and characterization of a first poliovirus genome which contains the complete 1.5 kb gag gene of HIV-1 substituted for the entire P1 region, and a second poliovirus genome in which the gag gene is positioned 3' to the VP4 coding region of the P1 capsid region are described herein. Transfection of RNA from each of the constructs into cells resulted in similar levels of protein expression and RNA replication. Both genomes were encapsidated upon transfection into cells previously infected with VV-P1. Serial passage of the recombinant poliovirus nucleic acids with VV-P1 resulted in the production of virus stocks of each of the encapsidated genomes. Analysis of the levels of encapsidated recombinant poliovirus nucleic acids after extended serial passage revealed that the recombinant poliovirus nucleic acids which contain the VP4 coding region were present at higher levels in the encapsidated virus stocks than the recombinant poliovirus nucleic acids which contain the gag gene substituted for the entire P1 region; no difference was detected in the levels of encapsidation of either recombinant poliovirus genome following limited serial passages in the presence of VV-P1 or Sabin type 1 poliovirus. The results of this study are significant because this is the first demonstration that poliovirus genomes which contain a foreign gene substituted for the entire P1 region can be encapsidated by P1 provided in trans.

Although the presence of the VP4 coding region was not absolutely required for RNA encapsidation, it was evident that recombinant poliovirus nucleic acids which contain a complete substitution of the P1 region with the HIV-1 gag gene were encapsidated less efficiently than recombinant poliovirus nucleic acids which maintain the VP4 coding sequences (nucleotides 743 to 949) positioned 5' to the gag gene. When RNA derived from each of the encapsidated recombinant poliovirus nucleic acid virus stocks after 21 serial passes with VV-P1 was isolated and quantitated by nucleic acid hybridization, the RNA from vIC-Pr55$^{gag}$(VP4/2A) and vIC-Gag 1 recombinant poliovirus nucleic acid virus stocks, which contained VP4, were present at levels that were 15 and 50 times higher, respectively, than RNA from vIC-Pr55$^{gag}$ virus stocks. Although it is clear from these results that VP4 is not required for encapsidation, the presence of VP4 might enhance RNA encapsidation. Since limited passage of equivalent amounts of each of the recombinant poliovirus nucleic acid virus stocks with VV-P1 indicated no significant difference in the encapsidation of recombinant poliovirus nucleic acids containing VP4 versus recombinant poliovirus nucleic acids which contain a deletion of the entire P1 coding region, it was possible that the effect of VP4 on encapsidation would be more apparent if the recombinant poliovirus RNA had to compete with the wild-type genomes for the P1 capsid protein. This situation would be analogous to the encapsidation of defective interfering (DI) genomes in that the defective genome must compete effectively with the wild-type genome to be maintained in the virus stock. However, it was determined that RNA from vIC-Pr55$^{gag}$ and vIC-Pr55$^{gag}$(VP4/2A) was maintained in virus stocks for 3 serial passages in the presence of type 1 poliovirus. Thus, during limited serial passage the recombinant poliovirus genomes did compete effectively with type 1 Sabin poliovirus RNA for capsid proteins. Using the complementation system described herein, it is possible to substitute the entire P1 region with at least 1.5 kb of foreign DNA. One feature of the expression system described herein is that the foreign protein is expressed as a polyprotein which is processed by 2A$^{pro}$. Thus, it is possible to express foreign proteins in a native conformation from poliovirus genomes if the residual amino acids at the amino or carboxy termini do not interfere with proper folding. Preliminary experiments have demonstrated the 55 kDa HIV-1 Gag protein expressed from poliovirus recombinant poliovirus nucleic acids is biologically active (i.e. formation of virus-like particles). If the exact protein sequence is required for protein function, the desired protein can be expressed using internal ribosomal entry sites positioned within the recombinant poliovirus nucleic acid.

MATERIALS AND METHODS III:

The following materials and methods were used in Examples 7, 8, and 9:

Plasmid Constructions

All manipulation of recombinant DNA was carried out according to standard procedures (Maniatis, T. et al. Molecular Cloning: A Laboratory Manual (Cold Spring Harbor Laboratory Press, Cold Spring Harbor, New York, 1982). The starting plasmid for these studies, pT7-IC, contains the entire full-length poliovirus infectious cDNA positioned immediately downstream from the phage T7 promoter (Choi, W. S. et al. (1991)*J. Virol.* 65:2875–2883). The full-length cDNA encoding CEA (shown in SEQ ID NO: 16, the amino acid sequence of CEA is shown in SEQ ID NO: 17), subcloned into pGEM plasmid (Beauchemin, N. et al. (1987)*Mol. Cell. Biol.* 7:3221–3230), was obtained from Dr. David Curiel, University of Alabama at Birmingham (originally obtained from Dr. Judy Kantor, NIH, Bethesda, Md.).

For construction of the backbone poliovirus vector used for insertion of the carcinoembryonic antigen (CEA) gene, two independent PCR reactions were performed. The first was used to amplify the region from nucleotides 1 to 743 of the poliovirus genome using the following PCR primers: 5'-CCA-GTG-AAT-TCC-TAA-TAC-GAC-TAC-CTA-TAG GTT-AAA-ACA-GC-3'(5' primer) (SEQ ID NO: 18) and 5'-GA-TGA-ACC-CTC-GAGACC-CAT-TAT-G-3'(3' primer) (SEQ ID NO: 19).

A second set of PCR primers were designed to amplify a region of the poliovirus genome from 3370 to 6117. The PCR primers were designed so that a unique SnaBI restriction site would be created 12 nucleotides from the end of the P1 gene, resulting in an additional four amino acids upstream from the tyrosine-glycine cleavage site. For subsequent subcloning, the PCR product was digested with SnaBI and BglII, which cuts at nucleotide 5601 in the poliovirus genome. The PCR primers used were as follows: 5'-CCA-CCA-AGTACG-TAA-CCA-CAT-ATG-G (5' primer) (SEQ ID NO: 20) and 5'-GTG-AGG-ACTG-CTGG-3'(3' primer) (SEQ ID NO: 21).

The conditions for PCR were as follows: 1 min at 94° C., 3 min at 37° C., and 3 min at 72° C. After 30 cycles, a 7-min incubation at 72° C. was included prior to cessation of the PCR reaction. PCR reactions were extracted successively with phenol:chloroform (1:1) and chloroform:isoamyl alcohol (24:1), and then DNA was precipitated with ethanol. After collection of the precipitate by centrifugation, the DNA was dried and resuspended in water.

The DNA was then digested with the appropriate restriction endonuclease enzymes at the 5' and 3' end of the PCR-amplified products.

Construction of pT7-IC-CEA-sig$^-$-

To obtain a signal minus version of the CEA gene, PCR was used to amplify a region from the CEA cDNA. The primers used for this PCR reaction were as follows: 5'-CAC-CAC-TGC-CCT-CGA-GAA-GCT-CAC-TAT-TG-3'(5' primer) (SEQ ID NO: 22) and 5'CAC-CAC-TGC-CCT-CGA-GAA-GCT-CAC-TAT-TG-3'(3' primer) (SEQ ID NO: 23).

The DNA primers were chosen to create an XhoI site at the 5' end and a SnaBI site at the 3' terminus of the amplified DNA. The length of the amplified DNA was approximately 100 base pairs less than that of the full-length amplified product for the CEA DNA, corresponding to a loss of 34 amino acids from the amino terminus representing the signal sequence. The conditions for PCR and isolation of the amplified product are as described in Materials and Methods III. Prior to ligation, the amplified product was digested with XhoI and SnaBI.

The plasmid pT7-IC was digested with EcoRI and BglII. The DNA fragment which contains the poliovirus genome from nucleotides 56012 to the SalI site (1.8 kilobases plus the 3.7 kilobases of the vector=5.5 kilobases) was isolated. In the same ligation, this 5.8-kilobase fragment was ligated with the PCR-amplified products from nucleotides 1–743 (EcoRI-XhoI), the CEA gene (XhoI-SnaBI), and the PCR-amplified product containing poliovirus nucleotides 3370 (SnaBI) to 5601 (BglII). After incubation at 15° C. overnight, the ligated products were transformed into *Escherichia coli* DH5α and the colonies were selected on ampicillin-containing plates. Plasmids isolated from individual colonies were screened for the desired insert by restriction enzyme digestion. The final plasmid was designated pT7-IC-CEA-sig$^-$.

Cell Culture and Viruses.

HeLa cells were purchased from the American Type Culture Collection and were maintained in monolayer culture in DMEM (GIBCO/BRL) supplemented with 5% fetal bovine serum. BSC-40 cells were maintained in DMEM with 5% fetal bovine serum as described previously (Ansardi, D. A. et al. (1991)*J. Virol.* 65:2088–2092).

The vaccinia viruses used for these studies were grown in TK-143-B cells (American Type Culture Collection) and were concentrated for experimental use as previously described (Ansardi, D. A. et al. (1991)*J. Virol.* 65:2088–2092). The titers of vaccinia virus were determined by plaque assay on BSC-40 cell monolayers. The recombinant vaccinia virus used for the encapsidation experiments (VV-P1) was constructed as described previously (Ansardi, D. A. et al. (1991)*J. Virol.* 65:2088–2092). The recombinant vaccinia virus which expresses the CEA (rV-CEA) has been previously described (Kantor, J. et al. (1992)*J. Natl. Cancer Inst.* 84:1084–1091; Kantor, J. et al. (1992)*Cancer Res.* 52:6917–6925).

In Vitro Transcription, Transfections, and Metabolic Labeling

In vitro transcription was carried out as described previously (Choi, W. S. et al. (1991) *J. Virol.* 65:2875–2883). The in vitro transcribed RNA was transfected into HeLa cells with DEAE-dextran (molecular mass, 500 kDa) as a facilitator as described previously (Choi, W. S. et al. (1991)*J. Virol.* 65:2875–2883). The cells were first infected with vaccinia virus for 2 h prior to transfection. After the 2 hour infection period, the cells were washed once with DMEM without methionine-cysteine or leucine (depending on the metabolic label), and incubated in this medium for an additional 45 min to 1 hour. In the case of recombinant poliovirus nucleic acid-infected cells, the infections were allowed to proceed 4–6 hours prior to metabolic labeling. For [$^{35}$S]methionine-cysteine labelings, the cells were washed once and incubated in DMEM without methionine-cysteine plus [$^{35}$S]methionine-cysteine (Translabel;ICN) 150 µCi/ml final concentration. In the case of metabolic labeling with [$^3$H]leucine, cells were labeled for 1.5 h using [$^3$H]leucine (Amersham) (350 µCi/ml) in a final volume of 0.2 ml leucine-free DMEM. After the labeling period, the cells were washed once with PBS and processed for radioimmunoprecipitation as described previously (Ansardi, D. A. et al. (1991)*J. Virol* 65:2088–2092). To detect CEA protein, a CEA-specific monoclonal antibody (Col-1) at a concentration of 3 µg/ml was used.

Encapsidation and Serial Passage of Recombinant poliovirus nucleic acids by VV-P1

Procedures for encapsidation of the recombinant poliovirus nucleic acids have been described previously (Porter, D. C. et al. ((1993)*J. Virol.* 67:3712–2719; Ansardi, D. A. et al. (1993)*J. Virol.* 67:3684–3690). Briefly, HeLa cells were infected with 20 PFUs/cell of VV-P1 for 2 hours. The cells were then transfected with in vitro transcribed RNA using DEAE-dextran (Choi, W. S. et al. (1991)*J. Virol.* 65:2875–2883). Sixteen hours after transfection, the cells and medium were harvested by directly adding Triton X-100 to the medium, at a final concentration of 1%. The medium-cell lysate was clarified in a microcentrifuge for 20 min at 14,000×g. The clarified lysate was treated with 20 µg/ml of RNase A at 37° C. for 15 min, then diluted to 4 ml with 30 mM Tris-HCl (pH 8.0, 0.1 M NaCl, 1% Triton X-100), and overlaid on a 0.5 ml-sucrose cushion (30% sucrose, 30 mM Tris-HCl pH 8.0, 1 M NaCl, 0.1% BSA) in SW 55 tubes. The sucrose cushion was centrifuged at 45,000 rpm for 2 h. Pelleted material was washed with PBS-0.1% BSA and recentrifuged at 45,000 rpm for 2 h. The final pellet was resuspended in 0.6 ml complete medium. BSC-40 cells were infected for 2 hours with 20 PFUs/cell of VV-P1, and 0.25 ml of the 0.6 ml was used to infect cells infected with VV-P1; after 24 hours, the cells and media were harvested. This was designated Pass 1.

For serial passage of the encapsidated recombinant poliovirus nucleic acids, BSC-40 cells were infected with 20 PFUs of VV-P1/cell. At 2 hours posttransfection, the cells were infected with Pass I of the encapsidated recombinant poliovirus nucleic acids. The cultures were harvested at 24 hours postinfection by three successive freeze-thaws, sonicated, and clarified by centrifugation at 14,000×g for 20 min. The supernatants were stored at −70° C. or used immediately for additional passages, following the same procedure.

Estimation of the Titer of Encapsidated Recombinant Poliovirus Nucleic Acids

Since the encapsidated recombinant poliovirus nucleic acids have the capacity to infect cells, but lack capsid proteins, they cannot form plaques and therefore virus titers cannot be quantified by traditional assays. To overcome this problem, a method to estimate the titer of the encapsidated recombinant poliovirus nucleic acids by comparison with wild-type poliovirus of known titer (Porter, D. C. et al. ((1993)*J. Virol.* 67:3712–2719; Ansardi, D. A. et al. (1993)*J. Virol.* 67:3684–3690) was used. The resulting titer is then expressed in infectious units of recombinant poliovirus nucleic acids, since the infection of cells with the recombinant poliovirus nucleic acids does not lead to plaque formation due to the absence of P1 capsid genes. It was determined experimentally that the infectivity of equal amounts of infectious units of encapsidated recombinant poliovirus nucleic acids correlates with equal amounts of PFUs of wild-type poliovirus.

Immunization of Mice and Analysis of CEA-Specific Antibody Response

The encapsidated recombinant poliovirus nucleic acids contain a type 1 Mahoney capsid. Since the type 1 strain of poliovirus does not infect mice, transgenic mice (designated as Tg PVR1) which express the receptor for poliovirus and are susceptible to poliovirus and are susceptible to poliovirus infection (Ren, R. et al. (1990)*Cell* 63:353–362) were used.

Mice (4–5-week old) were immunized by i.m. infection at monthly intervals with recombinant poliovirus nucleic acids expressing CEA; each mouse received 3 doses containing approximately 3–10$^4$ infectious units/mouse in 50 µl sterile PBS. To remove residual VV-P1, the recombinant poliovirus nucleic acid preparations were incubated with anti-vaccinia virus antibodies (Lee Biomolecular, San Diego, Calif.). The complete removal of residual VV-P1 was confirmed by the lack of vaccinia virus plaques after a 3-day plaque assay. Blood was collected from the tail veins of mice before and at selected times after immunization, centrifuged, and the plasma was collected and frozen until assay. ELISA was used for the determination of antigen-specific antibodies. The assays were performed in 96-well polystyrene microtiter plates (Dynatech, Alexandria, Va.) coated with recombinant CEA or whole poliovirus type 1 at a concentration of 5 and 1 µg/ml, respectively. The CEA used for these studies was expressed in *E. coli*, using a pET vector with a 6-histidine affinity tag to facilitate purification (Novagen). The majority of the CEA product isolated from the nickel column used for purification was an 80-kDa protein corresponding to the nonglycosylated CEA. The poliovirus type 1 (Sabin) used was grown in tissue culture cells and purified by centrifugation (Ansardi, D. A. et al. (1993)*J. Virol.* 67:3684–3690). Dilutions of sera were incubated overnight at 4° C. on coated and blocked ELISA plates, and the bound immunoglobulins were detected with horseradish peroxidase-labeled antimouse immunoglobulins (Southern Biotechnology Associates, Birmingham, Ala.). At the end of the incubation time (3 hours at 37° C.), the peroxidase substrate 2,2'-azino-bis-(3ethylbenzthiazoline) sulfonic acid (Sigma, St. Louis, Mo.) in citrate buffer (pH 4.2) containing 0.0075% $H_2O_2$ was added. The color developed was measured in $V_{max}$ kinetic microplate reader (Molecular Devices, Palo Alto, Calif.) at 414 nm. The results were expressed as absorbance values at a fixed dilution or as end point titration values.

EXAMPLE 7

CONSTRUCTION OF RECOMBINANT POLIOVIRUS NUCLEIC ACID CONTAINING THE GENE FOR CARCINOEMBRYONIC ANTIGEN

Figure 23A:
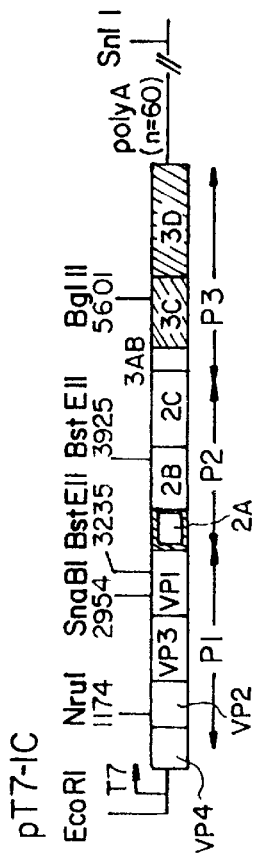
Figure 23B:
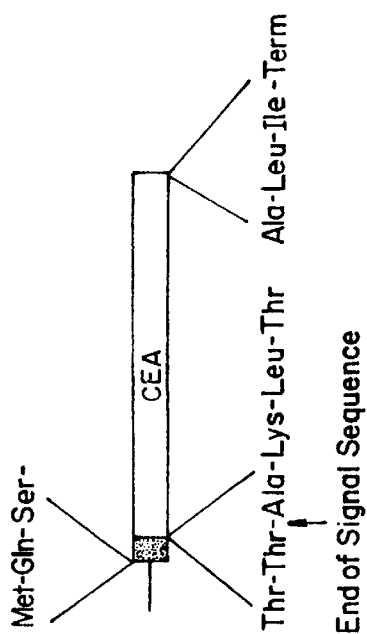
Figure 23C:
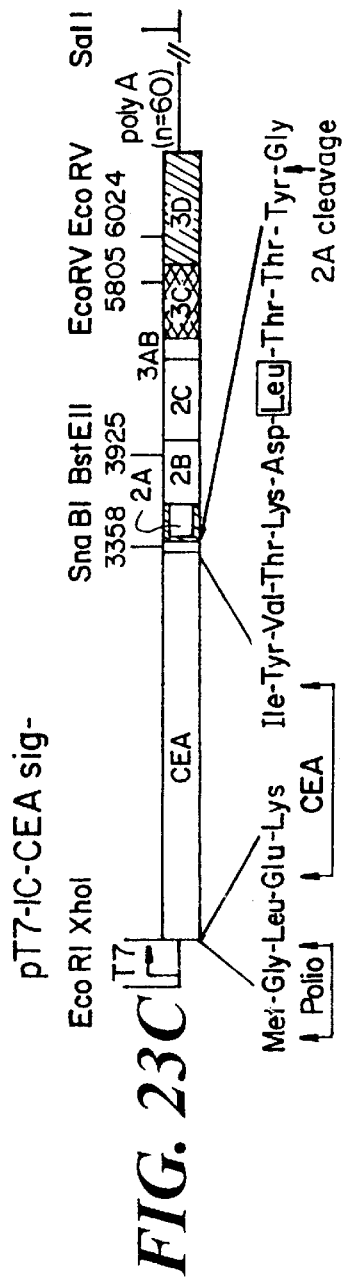

The starting plasmid for the experiments described herein contains the full-length infectious poliovirus cDNA positioned downstream from a phage T7 promoter, designated pT7-IC (Choi, W. S. et al. (1991)*J. Virol.* 65:2875–2883) (FIG. 23A). With reference to FIG. 23A, the poliovirus capsid proteins (VP4, VP3, VP2, and VP1) are encoded in the P1 region of the poliovirus genome; the viral proteinase 2A and viral proteins 2B and 2C are encoded in the P2 region; and the viral proteins 3AB, 3C, and 3D (RNA polymerase) are encoded in the P3 region. The relevant restriction sites used for construction of the recombinant poliovirus nucleic acid containing the gene for CEA are indicated. With reference to FIG. 23B, which is a schematic of the CEA protein, the signal sequence of the CEA protein consists of 34 amino acids (black box). The signal peptidase cleavage site occurs between the alanine and lysine amino acids. The codon for the carboxyl terminal isoleucine amino acid is followed by a TAA termination codon. Construction of the recombinant poliovirus nucleic acid containing the signal-minus CEA gene occurred as follows: PCR was used to amplify the CEA-gene encoding amino acids from the lysine at the amino terminus of signal-minus CEA to the isoleucine at the COOH terminus of CEA as shown in FIG. 23B. To subclone the gene encoding the signal-minus CEA protein, XhoI and SnaBI restriction endonuclease sites were positioned within the PCR primers. The final construct encodes the first two amino acids of the poliovirus P1 protein (Met-Gly) followed by two amino acids, leucine and glutamic acid (encoded by the XhoI restriction site) followed by the lysine amino acid of the signal-minus CEA protein. The CEA gene was positioned so that nine amino acids will be spaced between the C-terminal isoleucine of CEA and the tyrosine-glycine cleavage site for the 2A proteinase; the leucine amino acid required for 2A cleavage is boxed in FIG. 23C. This final construct, as shown in FIG. 23C, was designated pT7-IC-CEA-sig$^-$.

After the pT7-IC plasmid is linearized at the unique Sal I restriction site, in vitro transcription mediated by phage T7 RNA polymerase is used to generate RNA transcripts for transfection. Transfection of the in vitro RNA transcript into tissue culture cells (i.e., HeLa cells) results in translation and replication of the RNA, which leads to production of infectious poliovirus. It has been found that the infectivity of the RNA derived from this plasmid is in the range of $10^6$ PFUs/µg transfected RNA (Choi, W. S. et al. (1991)*J. Virol.* 65:2875–2883). Previous studies have found that the majority of the P1 region of the poliovirus cDNA can be deleted without affecting the capacity of the resulting RNA genome to replicate when transfected into cells (Kaplan, G. et al. (1988)*J. Virol.* 62:1687–1696). To extend these studies, it was investigated whether the entire P1 region can be substituted with the 2.4-kilobase cDNA for CEA (FIG. 23B; Beauchemin, N. et al. (1987)*Mol. Cell. Biol.* 7:3221–3230; Oikawa, S. et al. (1987)*Biochim. Biophys. Acta.* 142:511–518).

In preliminary studies, it was found that RNA containing full-length CEA was not replication competent. It was possible that the signal sequence (amino acids 1–34) of the CEA protein was directing the CEA-P2-P3 fusion protein to the endoplasmic reticulum and in doing so prevented replication of the RNA. To test this possibility, the CEA gene was engineered to remove the first 34 amino acids of the CEA protein, which has been postulated to be the signal sequence (Oikawa, S. et al. (1987)*Biochim. Biophys. Acta.* 142:511–518; Thompson, J. et al. (1988)*Tumor Biol.* 9:63–83). PCR was used to amplify a region from amino acids 35–688 of the CEA gene that was then subcloned into the poliovirus recombinant poliovirus nucleic acid. The resulting DNA encoded the first two amino acids of the poliovirus P1 protein (Met-Gly) followed by two amino acids (Leu-Glu) derived from the XhoI restriction endonuclease site, followed by amino acid 35 (Lys) of the CEA protein. The isoleucine in CEA was fused to an additional nine amino acids (Tyr-Val-Thr-Lys-Asp-Leu-Thr-Thr-Tyr) in the predicted protein product. In this CEA protein, a leucine residue at the P4 position was included for optimal 2A autocatalytic cleavage (Harris, K. S. et al. (1 990) *Semin. Virol.* 1:323–333).

Following in vitro transcription of pT7-IC-CEA-sig$^-$, the RNA transcripts were transfected into cells previously infected with VV-P1. For these studies five independent clones containing the signal-minus CEA gene (designated as sig$^-$CEA) were tested. As a positive control, a recombinant poliovirus nucleic acid which contains the HIV-1 gag gene (corresponding to the capsid, p24 protein) positioned between nucleotides 1174 and 2470 of the poliovirus genome was used. Cells were also infected with poliovirus to serve as a control in these experiments. At 6 hours posttransfection, the cells were metabolically labeled and $^{35}$S-labeled proteins were immunoprecipitated with either anti-3D$^{pol}$(FIG. 24A) of anti-CEA (Col-1 monoclonal antibody (FIG. 24B). The immunoprecipitated proteins were separated on SDS-10% polyacrylamide gels, and autoradiograms of these gels were generated (shown in FIGS. 24A and 24B). Additional sets of cells were either infected with poliovirus (FIG. 24A) or a recombinant vaccinia virus which expresses CEA (rV-CEA, FIG. 24B) to serve as a source of marker proteins. The origins of the samples in each of the lanes for both FIG. 24A and FIG. 24B are as follows: Lane 1, mock transfected cells; Lane 2, cells transfected with RNA derived from clone 1 of PT7-IC-CEA-sig$^-$; Lane 3, cells transfected with RNA derived from clone 2 of pT7-IC-CEA-sig$^-$; Lane 4, cells transfected with RNA derived from clone 3 of pT7-IC-CEA-sig$^-$; Lane 5, cells transfected with RNA derived from clone 4 of pT7-IC-CEA-sig$^-$; Lane 6, cells transfected with RNA derived from clone 5 of pT7-IC-CEA-sig$^-$; Lane 7, cells transfected with RNA derived from transcription of pT7-IC-Gag1; Lane 8, cells infected with either poliovirus (FIG. 24A) or rV-CEA (FIG. 24B). The migration of the molecular mass markers is noted. The migration of 3CD (FIG. 24A) and glycosylated and unglycosylated forms of CEA (FIG. 24B) are also noted.

In contrast to the results with the CEA recombinant poliovirus nucleic acids encoding the signal sequence, the 3CD protein from cells transfected with RNA derived from five individual clones of pT7-IC-CEA-sig$^-$ was detected. The levels of 3CD expression in this experiment were comparable to those of cells transfected with RNA derived from in vitro transcription of pT7-IC-Gag 1, which was known from previous studies to be replication competent (Porter, D.C. et al. (1993)*J. Virol.* 67:3712–3719; FIG. 24A). To determine if the CEA protein was expressed in the transfected cells, the lysates were also incubated with the Col-1 antibody to immunoprecipitate CEA-related proteins (FIG. 24B). Since the CEA protein should not be glycosylated, it was expected that the CEA product would be approximately 80 kDa in molecular mass. In each of the transfections with RNA derived the five independent clones, an 80-kDa protein was immunoprecipitated; this protein was not detected in cells transfected with recombinant poliovirus nucleic acids containing the HIV-1 gag gene.

EXAMPLE 8

ENCAPSIDATION AND SERIAL PASSAGE OF RECOMBINANT POLIOVIRUS NUCLEIC ACID CONTAINING THE GENE FOR CARCINOEMBRYONIC ANTIGEN

To determine whether the recombinant poliovirus nucleic acids containing the CEA sig$^-$ gene could be encapsidated if provided the poliovirus capsid proteins, cells were infected first with VV-P 1, followed by transfection with either the RNA derived pT7-IC-CEA-sig$^-$ or PT7-IC-Gag 1. A mock transfection was also included as an additional control. At 24 h posttransfection, extracts of the cells were generated by addition of detergents to the culture medium, and poliovirus-like particles were concentrated from the extracts by centrifugation through a 30% sucrose cushion. After resuspension, the concentrated material was used to infect cells that had been infected previously with either wild-type vaccinia virus or VV-P1 (passage 1). This coinfection was allowed to proceed overnight, after which extracts of the cells were generated by repeated freezing and thawing. The freeze-thaw extracts were clarified and used to repeat the coinfection procedure. This process was repeated for an additional nine serial passages to generate stocks of the encapsidated recombinant poliovirus nucleic acids. For the experiment shown in FIGS. 25A–C, the lysates from Pass 10 material were used to infect BSC-40 cells. At 6.5 hours postinfection, the cells were starved for 30 min in methionine-cysteine-free DMEM, and then were metabolically labeled for an additional 90 min. The cell lysates were then analyzed by immunoprecipitation with either anti-3D$^{pol}$ antibody (FIG. 25A) or antibody to the CEA protein (Col-1, FIG. 25B). The origins of the samples in the lanes for FIGS. 25A and 25B are as follows: Lane 1. cells that were infected with wild-type vaccinia virus and then mock-transfected; Lane 2,cells that were infected with VV-P1 and then mock-transfected; Lane 3, cells that were infected with wild-type vaccinia virus and then transfected with RNA derived from in vitro transcription of pT7-IC-CEA-sig$^-$; Lane 4, cells that were infected with VV-P1 and then transfected with RNA derived from pT7-IC-CEA-sig$^-$; Lane 5, cells that were infected with wild-type vaccinia virus and then transfected with RNA derived from pT7-IC-CEA-sig$^-$(a second independent clone); Lane 6, cells were infected with VV-P1 and then transfected with RNA derived from pT7-IC-CEA-sig$^-$(a second independent clone); Lane 7, cells that were infected with wild-type vaccinia virus and then transfected with RNA derived from in vitro transcription of pT7-IC-Gag 1; Lane 8, cells that were infected with VV-P1 and then transfected with RNA derived from in vitro transcription of pT7-IC-Gag 1; Lane 9, cells that were infected with poliovirus (FIG. 25A) or recombinant vaccinia virus CEA (rV-CEA, FIG. 25B). The migration of the molecular mass markers is noted. In FIG. 25A, the migration of 3CD protein is noted, whereas in FIG. 25B, the migrations of the glycosylated (gly) and nonglycosylated (sig$^-$) forms of CEA are noted. Arrows note the position of the anti-CEA immunoreactive proteins of larger molecular mass observed in cells infected with encapsidated poliovirus nucleic acid containing the signal-minus CEA gene. In FIG. 25C, cells were infected with a Pass 20 stock of encapsidated recombinant poliovirus nucleic acid containing the signal-minus CEA gene and then metabolically labeled with [$^3$H]leucine. The origins of the samples in the lanes for FIG. 25C are as follows: Lane 1 includes uninfected cells metabolically labeled, followed by immunoprecipitation with Col-1 antibody; Lane 2, cells infected with encapsidated recombinant poliovirus nucleic acid containing the signal-minus CEA gene, followed by immunoprecipitation with Col-1 antibody. The molecular mass standards are noted as well as the migration of glycosylated CEA (glyc.), nonglycosylated CEA (sig$^-$), and breakdown product (asterisk).

No expression of 3CD proteins was detected upon infection of cells with the sample originating from the mock-transfected cells and serially passaged 10 times with either wild-type vaccinia virus of VV-P1(FIG. 25A). From analysis of 3CD expression, it was concluded that RNA derived from transcription of pT7-IC-CEA-sig$^-$ was encapsidated when passaged in the presence of VV-P1, but not in the presence of wild-type vaccinia virus.

To determine if the CEA protein was expressed from the encapsidated recombinant poliovirus nucleic acids, the extracts from infected cells that had been metabolically labeled followed by immunoprecipitation with the Col-1 antibody (FIG. 25B) were analyzed. Again, in samples from mock-transfected cells that had been subsequently passaged in the presence of either wild-type vaccinia virus or VV-P1, no immunoreactive protein was detected. A protein of molecular mass 80 kDa was immunoprecipitated from cells infected with the extracts originating from cells transfected with the RNA derived from pT7-IC-CEA sig$^-$ which has been passaged in the presence of VV-P1, but not in the presence of wild-type virus. As expected, no Col-1 immunoreactive material was detected in cells infected with the RNA derived from pT7-IC-Gag 1, although this RNA was encapsidated in cells in the presence of VV-P1 (FIG. 25A).

Although the majority of the CEA protein immunoprecipitated from the cells infected with either stock of the encapsidated recombinant poliovirus RNA was the 80-kDa protein corresponding to the expected molecular mass of unglycosylated CEA, it was noted there was a small amount of protein immunoprecipitated corresponding to the molecular mass for the fully glycosylated CEA protein (180 kDa). To further explore this result, a concentrated stock of the signal-minus CEA recombinant poliovirus nucleic acid that had been passaged an additional 10 times (20 serial passages in all) and concentrated by pelleting through a 30% sucrose cushion prior to use in these experiments was used. Cells were infected with the encapsidated recombinant poliovirus nucleic acids, followed by metabolic radiolabeling for 1.5 h with [$^3$H]leucine since CEA contains more leucine amino acids than methionine or cysteine (Oikawa, S. et al. (1987) Biochim. Biophys. Acta. 142:511–518). This should increase the sensitivity of detection of the higher molecular mass CEA proteins. Three proteins were immunoprecipitated using the Col-1 antibody from [$^3$H]leucine-labeled cells infected with the stock of the encapsidated recombinant poliovirus nucleic acid (FIG. 25C). One of these proteins corresponded to the unglycosylated protein of a smaller molecular mass of approximately 80 kDa, while a protein of a smaller molecular mass, corresponding to approximately 52 kDa, was also immunoprecipitated. This protein is believed to represent a breakdown product of the CEA protein that was not detected previously because of the relatively few methionine or cysteine amino acids found in the CEA protein. A third protein of approximately 180 kDa was also immunoprecipitated, suggesting that glycosylated CEA protein might be produced in cells infected with the encapsidated recombinant poliovirus nucleic acids at low levels.

EXAMPLE 9

PRODUCTION OF ANTI-POLIOVIRUS AND ANTI-CARCINOEMBRYONIC ANTIGEN ANTIBODIES IN MICE IMMUNIZED WITH ENCAPSIDATED RECOMBINANT POLIOVIRUS NUCLEIC ACID CONTAINING THE GENE FOR CARCINOEMBRYONIC ANTIGEN

To evaluate the immunogenicity of the encapsidated recombinant poliovirus nucleic acids which express the CEA protein, transgenic mice that express the receptor for poliovirus and are susceptible to infection with poliovirus were used (Ren, R. et al. (1990)Cell 63:353–362). The mice were bred in a germ-free environment until use in the experiments. The four mice used in the experiment were bled prior to i.m. immunization with approximately 10$^4$ infectious units of the encapsidated recombinant poliovirus nucleic acid which expresses CEA. The serum samples from the mice at each of the pre- and postimmune time points were pooled and assayed using a solid-phase ELISA with whole poliovirus or recombinant CEA expressed in *E. coli* as the coating solution. The results are presented as absorbance 414-nm values at a fixed dilution and as end point titration values for anti-CEA (FIG. 26A) an antipoliovirus (FIG. 26B). By 28 days after the second booster immunization, a pronounced CEA-specific antibody response was detected as measured by the ELISA assay.

Figure 26A:
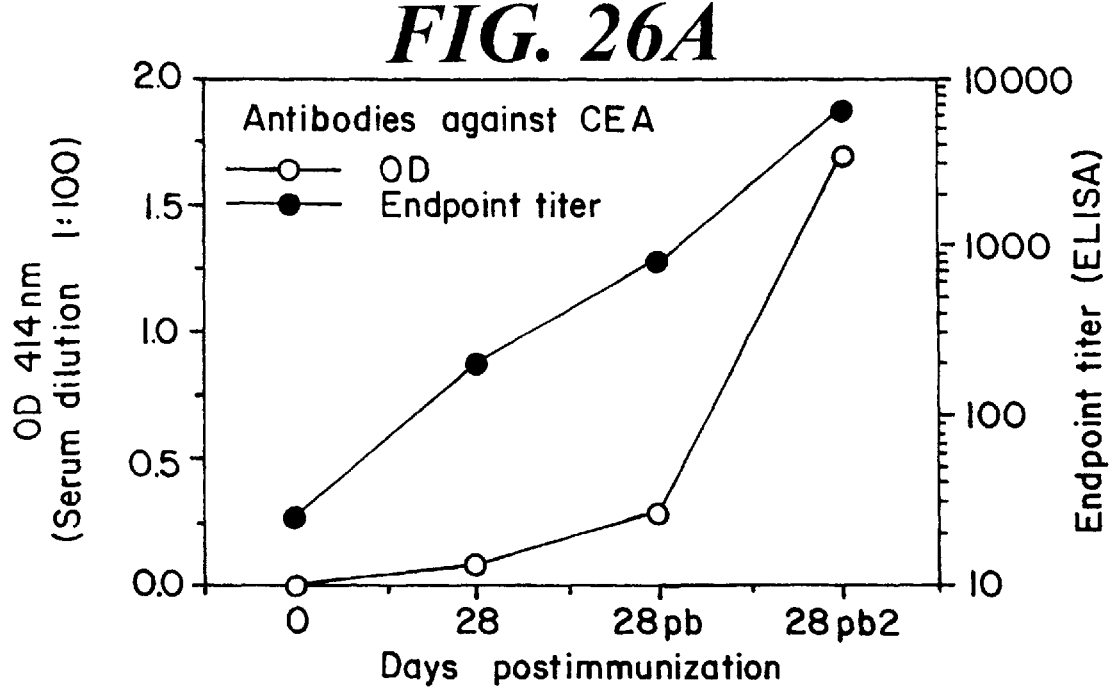
Figure 26B:
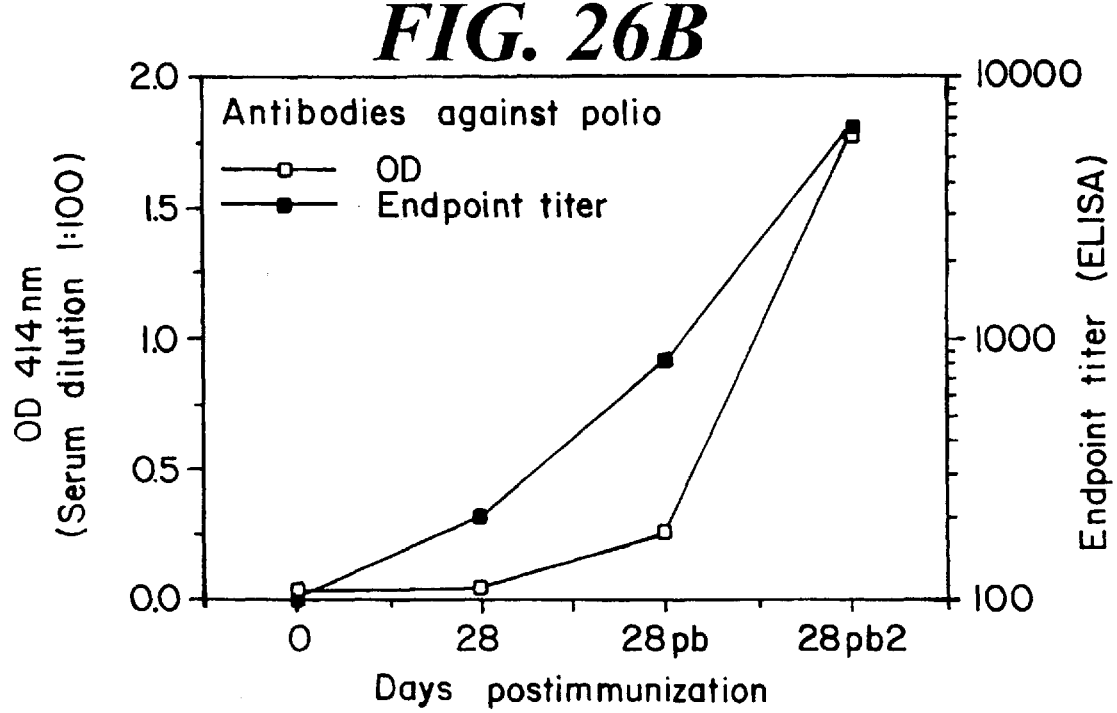

The end point titer had increased from 1:25 (preimmune) to 1:6400 (FIG. 26A). A similar increase was observed in the antipoliovirus in the serum samples (FIG. 26B). As a control, no increase in anti-CEA antibodies in the sera from mice immunized with the recombinant poliovirus nucleic acid expressing HIV-1 Gag was found. Taken together, these results demonstrate that the recombinant poliovirus nucleic acids infect cells, presumably the muscle myofibers at the site of injection, and express sufficient amounts of CEA to stimulate an anti-CEA antibody response.

The construction and characterization of RNA recombinant poliovirus nucleic acids which express the CEA protein when infected is described herein. A recombinant poliovirus nucleic acid encoding the signal-minus CEA protein was replication competent and expressed nonglycosylated CEA protein when transfected into cells. Using the methods of encapsidating recombinant poliovirus nucleic acids described herein, stocks of encapsidated recombinant poliovirus nucleic acids containing the signal-minus CEA gene were generated.

The use of encapsidated poliovirus recombinant poliovirus nucleic acids as a vaccine vehicle has several distinguishing features: (a) this is one of the few vector systems based entirely on an RNA virus. Since poliovirus replication does not involve DNA intermediates, in contrast to retroviruses, the possibility of recombination in the host cell DNA is virtually eliminated; (b) infection of cells with encapsidated recombinant poliovirus nucleic acids results in an amplification of the recombinant poliovirus nucleic acid RNA and preferential expression of the foreign gene over cellular gene products since poliovirus has evolved mechanisms to promote the synthesis of its own viral proteins (Ehrenfeld, E. et al. (1982)*Cell* 28:435–436); and (c) the encapsidated poliovirus recombinant poliovirus nucleic acids are noninfectious because they do not encode the viral P1 capsid proteins. The recombinant poliovirus nucleic acid requires capsid proteins to be propagated and transmitted from cell to cell. Infection of cells or an animal with the encapsidated recombinant poliovirus nucleic acids alone then results in a single round of infection without a chance for further spread. Because of this feature, the encapsidated recombinant poliovirus nucleic acids can be exploited to deliver nucleic acids to cells without risk of viral spread.

Equivalents

Those skilled in the art will recognize, or be able to ascertain using no more than routine experimentation, many equivalents to the specific embodiments of the invention described herein. Such equivalents are intended to be encompassed by the following claims.

All referenced patents and publications are hereby incorporated by reference in their entirety.

What is claimed is:

1. A method for stimulating an immune response to an immunogenic protein or fragment thereof, in a subject, comprising administering, in a physiologically acceptable carrier, an effective amount of a composition comprising a recombinant poliovirus nucleic acid having a foreign nucleotide sequence encoding, in an expressible form, an immunogenic protein or fragment thereof substituted for the entire P1 capsid precursor region of the poliovirus genome.

2. The method of claim 1 wherein the recombinant poliovirus nucleic acid is encapsidated.

3. The method of claim 1 wherein the composition is administered orally or by intramuscular injections.

4. The method of claim 1 wherein the immunogenic protein or fragment thereof is a human immunodeficiency virus type 1 protein or fragment thereof.

5. The method of claim 4 wherein the human immunodeficiency virus type 1 protein or fragment thereof is selected from the group consisting of the gag protein, the pol protein, and the env protein of human immunodeficiency virus type 1.

6. The method of claim 5 wherein the human immunodeficiency virus type 1 protein or fragment thereof comprises the human immunodeficiency virus type 1 gag protein (SEQ ID NO: 17).

7. The method of claim 1 wherein the immunogenic protein or fragment thereof is a tumor-associated antigen or fragment thereof.

8. The method of claim 7 wherein the tumor-associated antigen is carcinoembryonic antigen.

9. A method for stimulating in a subject an immune response to the gag protein of the human immunodeficiency virus type 1, comprising administering, in a physiologically acceptable carrier, an effective amount of a composition comprising an encapsidated recombinant poliovirus nucleic acid having the nucleotide sequence of the human immunodeficiency virus type 1 gag gene, in expressible form, substituted for the entire P1 capsid precursor region of the poliovirus genome.

10. A method for stimulating in a subject an immune response to carcinoembryonic antigen, comprising administering, in a physiologically acceptable carrier, an effective amount of a composition comprising an encapsidated recombinant poliovirus nucleic acid having the nucleotide sequence of the gene encoding the carcinoembryonic antigen, in expressible form, substituted for the entire P1 capsid precursor region of the poliovirus genome.

* * * * *

```
                         SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

TATTAGTAGA TCTG                                                  14

(2) INFORMATION FOR SEQ ID NO:2:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:2:

TACAGATGTA CTAA                                                  14
```

(2) INFORMATION FOR SEQ ID NO:3:

(i) SEQUENCE CHARACTERISTICS:
        (A) LENGTH: 845 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 20..845

(xi) SEQUENCE DESCRIPTION: SEQ ID NO:3:

```
ACACAGCAAT CAGGTCAGC CAA AAT TAC CCT ATA GTG CAG AAC ATC CAG GGG        52
                     Gln Asn Tyr Pro Ile Val Gln Asn Ile Gln Gly
                      1               5                  10

CAA ATG GTA CAT CAG GCC ATA TCA CCT AGA ACT TTA AAT GCA TGG GTA        100
Gln Met Val His Gln Ala Ile Ser Pro Arg Thr Leu Asn Ala Trp Val
         15                  20                  25

AAA GTA GTA GAA GAG AAG GCT TTC AGC CCA GAA GTG ATA CCC ATG TTT        148
Lys Val Val Glu Glu Lys Ala Phe Ser Pro Glu Val Ile Pro Met Phe
             30                  35                  40

TCA GCA TTA TCA GAA GGA GCC ACC CCA CAA GAT TTA AAC ACC ATG CTA        196
Ser Ala Leu Ser Glu Gly Ala Thr Pro Gln Asp Leu Asn Thr Met Leu
                 45                  50                  55

AAC ACA GTG GGG GGA CAT CAA GCA GCC ATG CAA ATG TTA AAA GAG ACC        244
Asn Thr Val Gly Gly His Gln Ala Ala Met Gln Met Leu Lys Glu Thr
 60                  65                  70                  75

ATC AAT GAG GAA GCT GCA GAA TGG GAT AGA GTG CAT CCA GTG CAT GCA        292
Ile Asn Glu Glu Ala Ala Glu Trp Asp Arg Val His Pro Val His Ala
                     80                  85                  90

GGG CCT ATT GCA CCA GGC CAG ATG AGA GAA CCA AGG GGA AGT GAC ATA        340
Gly Pro Ile Ala Pro Gly Gln Met Arg Glu Pro Arg Gly Ser Asp Ile
                 95                 100                 105

GCA GGA ACT ACT AGT ACC CTT CAG GAA CAA ATA GGA TGG ATG ACA AAT        388
Ala Gly Thr Thr Ser Thr Leu Gln Glu Gln Ile Gly Trp Met Thr Asn
             110                 115                 120

AAT CCA CCT ATC CCA GTA GGA GAA ATT TAT AAA AGA TGG ATA ATC CTG        436
Asn Pro Pro Ile Pro Val Gly Glu Ile Tyr Lys Arg Trp Ile Ile Leu
125                 130                 135

GGA TTA AAT AAA ATA GTA AGA ATG TAT AGC CCT ACC AGC ATT CTG GAC        484
Gly Leu Asn Lys Ile Val Arg Met Tyr Ser Pro Thr Ser Ile Leu Asp
140                 145                 150                 155

ATA AGA CAA GGA CCA AAG GAA CCC TTT AGA GAC TAT GTA GAC CGG TTC        532
Ile Arg Gln Gly Pro Lys Glu Pro Phe Arg Asp Tyr Val Asp Arg Phe
                 160                 165                 170

TAT AAA ACT CTA AGA GCC GAG CAA GCT TCA CAG GAG GTA AAA AAT TGG        580
Tyr Lys Thr Leu Arg Ala Glu Gln Ala Ser Gln Glu Val Lys Asn Trp
             175                 180                 185

ATG ACA GAA ACC TTG TTG GTC CAA AAT GCG AAC CCA GAT TGT AAG ACT        628
Met Thr Glu Thr Leu Leu Val Gln Asn Ala Asn Pro Asp Cys Lys Thr
         190                 195                 200

ATT TTA AAA GCA TTG GGA CCA GCG GCT ACA CTA GAA GAA ATG ATG ACA        676
Ile Leu Lys Ala Leu Gly Pro Ala Ala Thr Leu Glu Glu Met Met Thr
 205                 210                 215

GCA TGT CAG GGA GTA GGA GGA CCC GGC CAT AAG GCA AGA GTT TTG GCT        724
Ala Cys Gln Gly Val Gly Gly Pro Gly His Lys Ala Arg Val Leu Ala
220                 225                 230                 235

GAA GCA ATG AGC CAA GTA ACA AAT TCA GCT ACC ATA ATG ATG CAG AGA        772
Glu Ala Met Ser Gln Val Thr Asn Ser Ala Thr Ile Met Met Gln Arg
                     240                 245                 250
```

```
GGC AAT TTT AGG AAC CAA AGA AAG ATT GTT AAG TGT TTC AAT TGT GGC         820
Gly Asn Phe Arg Asn Gln Arg Lys Ile Val Lys Cys Phe Asn Cys Gly
            255                 260                 265

AAA GAA GGG CAC ACA GCC AGA AAG T                                       845
Lys Glu Gly His Thr Ala Arg Lys
        270                 275
```

(2) INFORMATION FOR SEQ ID NO:4:

(i) SEQUENCE CHARACTERISTICS:
        (A) LENGTH: 275 amino acids
        (B) TYPE: amino acid
        (D) TOPOLOGY: linear (ii) MOLECULE TYPE: protein (xi) SEQUENCE DESCRIPTION: SEQ ID NO:4:

```
Gln Asn Tyr Pro Ile Val Gln Asn Ile Gln Gly Gln Met Val His Gln
 1               5                  10                  15

Ala Ile Ser Pro Arg Thr Leu Asn Ala Trp Val Lys Val Val Glu Glu
            20                  25                  30

Lys Ala Phe Ser Pro Glu Val Ile Pro Met Phe Ser Ala Leu Ser Glu
        35                  40                  45

Gly Ala Thr Pro Gln Asp Leu Asn Thr Met Leu Asn Thr Val Gly Gly
    50                  55                  60

His Gln Ala Ala Met Gln Met Leu Lys Glu Thr Ile Asn Glu Glu Ala
65                  70                  75                  80

Ala Glu Trp Asp Arg Val His Pro Val His Ala Gly Pro Ile Ala Pro
                85                  90                  95

Gly Gln Met Arg Glu Pro Arg Gly Ser Asp Ile Ala Gly Thr Thr Ser
            100                 105                 110

Thr Leu Gln Glu Gln Ile Gly Trp Met Thr Asn Asn Pro Pro Ile Pro
        115                 120                 125

Val Gly Glu Ile Tyr Lys Arg Trp Ile Ile Leu Gly Leu Asn Lys Ile
    130                 135                 140

Val Arg Met Tyr Ser Pro Thr Ser Ile Leu Asp Ile Arg Gln Gly Pro
145                 150                 155                 160

Lys Glu Pro Phe Arg Asp Tyr Val Asp Arg Phe Tyr Lys Thr Leu Arg
                165                 170                 175

Ala Glu Gln Ala Ser Gln Glu Val Lys Asn Trp Met Thr Glu Thr Leu
            180                 185                 190

Leu Val Gln Asn Ala Asn Pro Asp Cys Lys Thr Ile Leu Lys Ala Leu
        195                 200                 205

Gly Pro Ala Ala Thr Leu Glu Glu Met Met Thr Ala Cys Gln Gly Val
    210                 215                 220

Gly Gly Pro Gly His Lys Ala Arg Val Leu Ala Glu Ala Met Ser Gln
225                 230                 235                 240

Val Thr Asn Ser Ala Thr Ile Met Met Gln Arg Gly Asn Phe Arg Asn
                245                 250                 255

Gln Arg Lys Ile Val Lys Cys Phe Asn Cys Gly Lys Glu Gly His Thr
            260                 265                 270

Ala Arg Lys
        275
```

(2) INFORMATION FOR SEQ ID NO:5:

(i) SEQUENCE CHARACTERISTICS:

(A) LENGTH: 948 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 4..946

(xi) SEQUENCE DESCRIPTION: SEQ ID NO:5:

```
AAC CAA TGG CCA TTG ACA GAA GAA AAA ATA AAA GCA TTA GTA GAA ATT        48
    Gln Trp Pro Leu Thr Glu Glu Lys Ile Lys Ala Leu Val Glu Ile
    1               5                  10                  15

TGT ACA GAG ATG GAA AAG GAA GGG AAA ATT TCA AAA ATT GGG CCT GAA        96
Cys Thr Glu Met Glu Lys Glu Gly Lys Ile Ser Lys Ile Gly Pro Glu
                20                  25                  30

AAT CCA TAC AAT ACT CCA GTA TTT GCC ATA AAG AAA AAA GAC AGT ACT       144
Asn Pro Tyr Asn Thr Pro Val Phe Ala Ile Lys Lys Lys Asp Ser Thr
            35                  40                  45

AAA TGG AGA AAA TTA GTA GAT TTC AGA GAA CTT AAT AAG AGA ACT CAA       192
Lys Trp Arg Lys Leu Val Asp Phe Arg Glu Leu Asn Lys Arg Thr Gln
        50                  55                  60

GAC TTC TGG GAA GTT CAA TTA GGA ATA CCA CAT CCC GCA GGG TTA AAA       240
Asp Phe Trp Glu Val Gln Leu Gly Ile Pro His Pro Ala Gly Leu Lys
    65                  70                  75

AAG AAA AAA TCA GTA ACA GTA CTG GAT GTG GGT GAT GCA TAT TTT TCA       288
Lys Lys Lys Ser Val Thr Val Leu Asp Val Gly Asp Ala Tyr Phe Ser
80                  85                  90                  95

GTT CCC TTA GAT GAA GAC TTC AGG AAG TAT ACT GCA TTT ACC ATA CCT       336
Val Pro Leu Asp Glu Asp Phe Arg Lys Tyr Thr Ala Phe Thr Ile Pro
                100                 105                 110

AGT ATA AAC AAT GAG ACA CCA GGG ATT AGA TAT CAG TAC AAT GTG CTT       384
Ser Ile Asn Asn Glu Thr Pro Gly Ile Arg Tyr Gln Tyr Asn Val Leu
            115                 120                 125

CCA CAG GGA TGG AAA GGA TCA CCA GCA ATA TTC CAA AGT AGC ATG ACA       432
Pro Gln Gly Trp Lys Gly Ser Pro Ala Ile Phe Gln Ser Ser Met Thr
        130                 135                 140

AAA ATC TTA GAG CCT TTT AGA AAA CAA AAT CCA GAC ATA GTT ATC TAT       480
Lys Ile Leu Glu Pro Phe Arg Lys Gln Asn Pro Asp Ile Val Ile Tyr
    145                 150                 155

CAA TAC ATG GAT GAT TTG TAT GTA GGA TCT GAC TTA GAA ATA GGG CAG       528
Gln Tyr Met Asp Asp Leu Tyr Val Gly Ser Asp Leu Glu Ile Gly Gln
160                 165                 170                 175

CAT AGA ACA AAA ATA GAG GAG CTG AGA CAA CAT CTG TTG AGG TGG GGA       576
His Arg Thr Lys Ile Glu Glu Leu Arg Gln His Leu Leu Arg Trp Gly
                180                 185                 190

CTT ACC ACA CCA GAC AAA AAA CAT CAG AAA GAA CCT CCA TTC CTT TGG       624
Leu Thr Thr Pro Asp Lys Lys His Gln Lys Glu Pro Pro Phe Leu Trp
            195                 200                 205

ATG GGT TAT GAA CTC CAT CCT GAT AAA TGG ACA GTA CAG CCT ATA GTG       672
Met Gly Tyr Glu Leu His Pro Asp Lys Trp Thr Val Gln Pro Ile Val
        210                 215                 220

CTG CCA GAA AAA GAC AGC TGG ACT GTC AAT GAC ATA CAG AAG TTA GTG       720
Leu Pro Glu Lys Asp Ser Trp Thr Val Asn Asp Ile Gln Lys Leu Val
    225                 230                 235

GGG AAA TTG AAT TGG GCA AGT CAG ATT TAC CCA GGG ATT AAA GTA AGG       768
Gly Lys Leu Asn Trp Ala Ser Gln Ile Tyr Pro Gly Ile Lys Val Arg
240                 245                 250                 255

CAA TTA TGT AAA CTC CTT AGA GGA ACC AAA GCA CTA ACA GAA GTA ATA       816
Gln Leu Cys Lys Leu Leu Arg Gly Thr Lys Ala Leu Thr Glu Val Ile
```

```
                    260                 265                 270
CCA CTA ACA GAA GAA GCA GAG CTA GAA CTG GCA GAA AAC AGA GAG ATT        864
Pro Leu Thr Glu Glu Ala Glu Leu Glu Leu Ala Glu Asn Arg Glu Ile
            275                 280                 285

CTA AAA GAA CCA GTA CAT GGA GTG TAT TAT GAC CCA TCA AAA GAC TTA        912
Leu Lys Glu Pro Val His Gly Val Tyr Tyr Asp Pro Ser Lys Asp Leu
            290                 295                 300

ATA GCA GAA ATA CAG AAG CAG GGG CAA GGC CTCGAG                         948
Ile Ala Glu Ile Gln Lys Gln Gly Gln Gly
            305                 310

(2) INFORMATION FOR SEQ ID NO:6:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:6:

Gln Trp Pro Leu Thr Glu Glu Lys Ile Lys Ala Leu Val Glu Ile Cys
 1               5                  10                  15

Thr Glu Met Glu Lys Glu Gly Lys Ile Ser Lys Ile Gly Pro Glu Asn
                20                  25                  30

Pro Tyr Asn Thr Pro Val Phe Ala Ile Lys Lys Lys Asp Ser Thr Lys
            35                  40                  45

Trp Arg Lys Leu Val Asp Phe Arg Glu Leu Asn Lys Arg Thr Gln Asp
        50                  55                  60

Phe Trp Glu Val Gln Leu Gly Ile Pro His Pro Ala Gly Leu Lys Lys
 65                  70                  75                  80

Lys Lys Ser Val Thr Val Leu Asp Val Gly Asp Ala Tyr Phe Ser Val
                85                  90                  95

Pro Leu Asp Glu Asp Phe Arg Lys Tyr Thr Ala Phe Thr Ile Pro Ser
            100                 105                 110

Ile Asn Asn Glu Thr Pro Gly Ile Arg Tyr Gln Tyr Asn Val Leu Pro
        115                 120                 125

Gln Gly Trp Lys Gly Ser Pro Ala Ile Phe Gln Ser Ser Met Thr Lys
130                 135                 140

Ile Leu Glu Pro Phe Arg Lys Gln Asn Pro Asp Ile Val Ile Tyr Gln
145                 150                 155                 160

Tyr Met Asp Asp Leu Tyr Val Gly Ser Asp Leu Glu Ile Gly Gln His
                165                 170                 175

Arg Thr Lys Ile Glu Glu Leu Arg Gln His Leu Leu Arg Trp Gly Leu
            180                 185                 190

Thr Thr Pro Asp Lys Lys His Gln Lys Glu Pro Pro Phe Leu Trp Met
        195                 200                 205

Gly Tyr Glu Leu His Pro Asp Lys Trp Thr Val Gln Pro Ile Val Leu
    210                 215                 220

Pro Glu Lys Asp Ser Trp Thr Val Asn Asp Ile Gln Lys Leu Val Gly
225                 230                 235                 240

Lys Leu Asn Trp Ala Ser Gln Ile Tyr Pro Gly Ile Lys Val Arg Gln
                245                 250                 255

Leu Cys Lys Leu Leu Arg Gly Thr Lys Ala Leu Thr Glu Val Ile Pro
            260                 265                 270

Leu Thr Glu Glu Ala Glu Leu Glu Leu Ala Glu Asn Arg Glu Ile Leu
        275                 280                 285
```

```
        Lys Glu Pro Val His Gly Val Tyr Tyr Asp Pro Ser Lys Asp Leu Ile
            290                 295                 300

Ala Glu Ile Gln Lys Gln Gly Gln Gly Leu
        305                 310

(2) INFORMATION FOR SEQ ID NO:7:

(i) SEQUENCE CHARACTERISTICS:
         (A) LENGTH: 1568 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 7..1565

(xi) SEQUENCE DESCRIPTION: SEQ ID NO:7:

GGGGCC TGT CCA AAG GTA TCC TTT GAG CCA ATT CCC ATA CAT TAT TGT             48
       Cys Pro Lys Val Ser Phe Glu Pro Ile Pro Ile His Tyr Cys
         1               5                  10

GCC CCG GCT GGT TTT GCG ATT CTA AAA TGT AAT AAT AAG ACG TTC AAT            96
Ala Pro Ala Gly Phe Ala Ile Leu Lys Cys Asn Asn Lys Thr Phe Asn
 15                  20                  25                  30

GGA ACA GGA CCA TGT ACA AAT GTC AGC ACA GTA CAA TGT ACA CAT GGA           144
Gly Thr Gly Pro Cys Thr Asn Val Ser Thr Val Gln Cys Thr His Gly
                 35                  40                  45

ATT AGG CCA GTA GTA TCA ACT CAA CTG CTG TTA AAT GGC AGT CTA GCA           192
Ile Arg Pro Val Val Ser Thr Gln Leu Leu Leu Asn Gly Ser Leu Ala
             50                  55                  60

GAA GAA GAG GTA GTA ATT AGA TCT GTC AAT TTC ACG GAC AAT GCT AAA           240
Glu Glu Glu Val Val Ile Arg Ser Val Asn Phe Thr Asp Asn Ala Lys
 65                  70                  75

ACC ATA ATA GTA CAG CTG AAC ACA TCT GTA GAA ATT AAT TGT ACA AGA           288
Thr Ile Ile Val Gln Leu Asn Thr Ser Val Glu Ile Asn Cys Thr Arg
     80                  85                  90

CCC AAC AAC AAT ACA AGA AAA AGA ATC CGT ATC CAG AGA GGA CCA GGG           336
Pro Asn Asn Asn Thr Arg Lys Arg Ile Arg Ile Gln Arg Gly Pro Gly
 95                 100                 105                 110

AGA GCA TTT GTT ACA ATA GGA AAA ATA GGA AAT ATG AGA CAA GCA CAT           384
Arg Ala Phe Val Thr Ile Gly Lys Ile Gly Asn Met Arg Gln Ala His
                115                 120                 125

TGT AAC ATT AGT AGA GCA AAA TGG AAT AAC ACT TTA AAA CAG ATA GAT           432
Cys Asn Ile Ser Arg Ala Lys Trp Asn Asn Thr Leu Lys Gln Ile Asp
            130                 135                 140

AGC AAA TTA AGA GAA CAA TTC GGA AAT AAT AAA ACA ATA ATC TTT AAG           480
Ser Lys Leu Arg Glu Gln Phe Gly Asn Asn Lys Thr Ile Ile Phe Lys
145                 150                 155

CAA TCC TCA GGA GGG GAC CCA GAA ATT GTA ACG CAC AGT TTT AAT TGT           528
Gln Ser Ser Gly Gly Asp Pro Glu Ile Val Thr His Ser Phe Asn Cys
    160                 165                 170

GGA GGG GAA TTT TTC TAC TGT AAT TCA ACA CAA CTG TTT AAT AGT ACT           576
Gly Gly Glu Phe Phe Tyr Cys Asn Ser Thr Gln Leu Phe Asn Ser Thr
175                 180                 185                 190

TGG TTT AAT AGT ACT TGG AGT ACT GAA GGG TCA AAT AAC ACT GAA GGA           624
Trp Phe Asn Ser Thr Trp Ser Thr Glu Gly Ser Asn Asn Thr Glu Gly
                195                 200                 205

AGT GAC ACA ATC ACC CTC CCA TGC AGA ATA AAA CAA ATT ATA AAC ATG           672
Ser Asp Thr Ile Thr Leu Pro Cys Arg Ile Lys Gln Ile Ile Asn Met
            210                 215                 220
```

```
TGG CAG AAA GTA GGA AAA GCA ATG TAT GCC CCT CCC ATC AGT GGA CAA        720
Trp Gln Lys Val Gly Lys Ala Met Tyr Ala Pro Pro Ile Ser Gly Gln
        225                 230                 235

ATT AGA TGT TCA TCA AAT ATT ACA GGG CTG CTA TTA ACA AGA GAT GGT        768
Ile Arg Cys Ser Ser Asn Ile Thr Gly Leu Leu Leu Thr Arg Asp Gly
        240                 245                 250

GGT AAT AGC AAC AAT GAG TCC GAG ATC TTC AGA CTT GGA GGA GGA GAT        816
Gly Asn Ser Asn Asn Glu Ser Glu Ile Phe Arg Leu Gly Gly Gly Asp
255                 260                 265                 270

ATG AGG GAC AAT TGG AGA AGT GAA TTA TAT AAA TAT AAA GTA GTA AAA        864
Met Arg Asp Asn Trp Arg Ser Glu Leu Tyr Lys Tyr Lys Val Val Lys
                275                 280                 285

ATT GAA CCA TTA GGA GTA GCA CCC ACC AAG GCA AAG AGA AGA GTG GTG        912
Ile Glu Pro Leu Gly Val Ala Pro Thr Lys Ala Lys Arg Arg Val Val
        290                 295                 300

CAG AGA GAA AAA AGA GCA GTG GGA ATA GGA GCT TTG TTC CTT GGG TTC        960
Gln Arg Glu Lys Arg Ala Val Gly Ile Gly Ala Leu Phe Leu Gly Phe
        305                 310                 315

TTG GGA GCA GCA GGA AGC ACT ATG GGC GCA GCC TCA ATG ACG CTG ACG       1008
Leu Gly Ala Ala Gly Ser Thr Met Gly Ala Ala Ser Met Thr Leu Thr
        320                 325                 330

GTA CAG GCC AGA CAA TTA TTG TCT GGT ATA GTG CAG CAG CAG AAC AAT       1056
Val Gln Ala Arg Gln Leu Leu Ser Gly Ile Val Gln Gln Gln Asn Asn
335                 340                 345                 350

TTG CTG AGG GCT ATT GAG GCG CAA CAG CAT CTG TTG CAA CTC ACA GTC       1104
Leu Leu Arg Ala Ile Glu Ala Gln Gln His Leu Leu Gln Leu Thr Val
                355                 360                 365

TGG GGC ATC AAG CAG CTC CAA GCA AGA ATC CTA GCT GTG GAA AGA TAC       1152
Trp Gly Ile Lys Gln Leu Gln Ala Arg Ile Leu Ala Val Glu Arg Tyr
        370                 375                 380

CTA AAG GAT CAA CAG CTC CTA GGG ATT TGG GGT TGC TCT GGA AAA CTC       1200
Leu Lys Asp Gln Gln Leu Leu Gly Ile Trp Gly Cys Ser Gly Lys Leu
        385                 390                 395

ATT TGC ACC ACT GCT GTG CCT TGG AAT GCT AGT TGG AGT AAT AAA TCT       1248
Ile Cys Thr Thr Ala Val Pro Trp Asn Ala Ser Trp Ser Asn Lys Ser
400                 405                 410

CTG GAA CAG ATC TGG AAT CAC ACG ACC TGG ATG GAG TGG GAC AGA GAA       1296
Leu Glu Gln Ile Trp Asn His Thr Thr Trp Met Glu Trp Asp Arg Glu
415                 420                 425                 430

ATT AAC AAT TAC ACA AGC TTA ATA CAC TCC TTA ATT GAA GAA TCG CAA       1344
Ile Asn Asn Tyr Thr Ser Leu Ile His Ser Leu Ile Glu Glu Ser Gln
                435                 440                 445

AAC CAG CAA GAA AAG AAT GAA CAA GAA TTA TTG GAA TTA GAT AAA TGG       1392
Asn Gln Gln Glu Lys Asn Glu Gln Glu Leu Leu Glu Leu Asp Lys Trp
        450                 455                 460

GCA AGT TTG TGG AAT TGG TTT AAC ATA ACA AAT TGG CTG TGG TAT ATA       1440
Ala Ser Leu Trp Asn Trp Phe Asn Ile Thr Asn Trp Leu Trp Tyr Ile
        465                 470                 475

AAA TTA TTC ATA ATG ATA GTA GGA GGC TTG GTA GGT TTA AGA ATA GTT       1488
Lys Leu Phe Ile Met Ile Val Gly Gly Leu Val Gly Leu Arg Ile Val
        480                 485                 490

TTT GCT GTA CTT TCT ATA GTG AAT AGA GTT AGG CAG GGA TAT TCA CCA       1536
Phe Ala Val Leu Ser Ile Val Asn Arg Val Arg Gln Gly Tyr Ser Pro
495                 500                 505                 510

TTA TCG TTT CAG ACC CAC CTC CCA ATC TCGAG                             1568
Leu Ser Phe Gln Thr His Leu Pro Ile
                515
```

(2) INFORMATION FOR SEQ ID NO:8:

(i) SEQUENCE CHARACTERISTICS:
    (A) LENGTH: 519 amino acids
    (B) TYPE: amino acid
    (D) TOPOLOGY: linear (ii) MOLECULE TYPE: protein (xi) SEQUENCE DESCRIPTION: SEQ ID NO:8:

```
Cys Pro Lys Val Ser Phe Glu Pro Ile Pro Ile His Tyr Cys Ala Pro
 1               5                  10                  15

Ala Gly Phe Ala Ile Leu Lys Cys Asn Asn Lys Thr Phe Asn Gly Thr
            20                  25                  30

Gly Pro Cys Thr Asn Val Ser Thr Val Gln Cys Thr His Gly Ile Arg
        35                  40                  45

Pro Val Val Ser Thr Gln Leu Leu Asn Gly Ser Leu Ala Glu Glu
    50                  55                  60

Glu Val Val Ile Arg Ser Val Asn Phe Thr Asp Asn Ala Lys Thr Ile
 65                  70                  75                  80

Ile Val Gln Leu Asn Thr Ser Val Glu Ile Asn Cys Thr Arg Pro Asn
                85                  90                  95

Asn Asn Thr Arg Lys Arg Ile Arg Ile Gln Arg Gly Pro Gly Arg Ala
            100                 105                 110

Phe Val Thr Ile Gly Lys Ile Gly Asn Met Arg Gln Ala His Cys Asn
        115                 120                 125

Ile Ser Arg Ala Lys Trp Asn Asn Thr Leu Lys Gln Ile Asp Ser Lys
    130                 135                 140

Leu Arg Glu Gln Phe Gly Asn Asn Lys Thr Ile Ile Phe Lys Gln Ser
145                 150                 155                 160

Ser Gly Gly Asp Pro Glu Ile Val Thr His Ser Phe Asn Cys Gly Gly
                165                 170                 175

Glu Phe Phe Tyr Cys Asn Ser Thr Gln Leu Phe Asn Ser Thr Trp Phe
            180                 185                 190

Asn Ser Thr Trp Ser Thr Glu Gly Ser Asn Asn Thr Glu Gly Ser Asp
        195                 200                 205

Thr Ile Thr Leu Pro Cys Arg Ile Lys Gln Ile Ile Asn Met Trp Gln
    210                 215                 220

Lys Val Gly Lys Ala Met Tyr Ala Pro Pro Ile Ser Gly Gln Ile Arg
225                 230                 235                 240

Cys Ser Ser Asn Ile Thr Gly Leu Leu Leu Thr Arg Asp Gly Gly Asn
                245                 250                 255

Ser Asn Asn Glu Ser Glu Ile Phe Arg Leu Gly Gly Gly Asp Met Arg
            260                 265                 270

Asp Asn Trp Arg Ser Glu Leu Tyr Lys Tyr Lys Val Val Lys Ile Glu
        275                 280                 285

Pro Leu Gly Val Ala Pro Thr Lys Ala Lys Arg Arg Val Val Gln Arg
    290                 295                 300

Glu Lys Arg Ala Val Gly Ile Gly Ala Leu Phe Leu Gly Phe Leu Gly
305                 310                 315                 320

Ala Ala Gly Ser Thr Met Gly Ala Ala Ser Met Thr Leu Thr Val Gln
                325                 330                 335

Ala Arg Gln Leu Leu Ser Gly Ile Val Gln Gln Asn Asn Leu Leu
            340                 345                 350

Arg Ala Ile Glu Ala Gln Gln His Leu Leu Gln Leu Thr Val Trp Gly
        355                 360                 365
```

Ile Lys Gln Leu Gln Ala Arg Ile Leu Ala Val Glu Arg Tyr Leu Lys
    370                 375                 380

Asp Gln Gln Leu Leu Gly Ile Trp Gly Cys Ser Gly Lys Leu Ile Cys
385                 390                 395                 400

Thr Thr Ala Val Pro Trp Asn Ala Ser Trp Ser Asn Lys Ser Leu Glu
                405                 410                 415

Gln Ile Trp Asn His Thr Thr Trp Met Glu Trp Asp Arg Glu Ile Asn
                420                 425                 430

Asn Tyr Thr Ser Leu Ile His Ser Leu Ile Glu Glu Ser Gln Asn Gln
            435                 440                 445

Gln Glu Lys Asn Glu Gln Glu Leu Leu Glu Leu Asp Lys Trp Ala Ser
450                 455                 460

Leu Trp Asn Trp Phe Asn Ile Thr Asn Trp Leu Trp Tyr Ile Lys Leu
465                 470                 475                 480

Phe Ile Met Ile Val Gly Gly Leu Val Gly Leu Arg Ile Val Phe Ala
                485                 490                 495

Val Leu Ser Ile Val Asn Arg Val Arg Gln Gly Tyr Ser Pro Leu Ser
                500                 505                 510

Phe Gln Thr His Leu Pro Ile
        515

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CACCCCTCTC CTACGTAACC AAGGATC                                27

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTACTGGTCA CCATATTGGT CAAC                                   24

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GGAGAGAGAT GGGAGCTCGA GCGTC                                  25

(2) INFORMATION FOR SEQ ID NO:12:

(i) SEQUENCE CHARACTERISTICS:

(A) LENGTH: 20 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO:12:

GCCCCCCTAT ACGTATTGTG                                                        20

(2) INFORMATION FOR SEQ ID NO:13:

(i) SEQUENCE CHARACTERISTICS:
                    (A) LENGTH: 41 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO:13:

CCAGTGAATT CCTAATACGA CTCACTATAG GTTAAAACAG C                                41

(2) INFORMATION FOR SEQ ID NO:14:

(i) SEQUENCE CHARACTERISTICS:
                    (A) LENGTH: 48 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO:14:

CTCTATCCTG AGCTCCATAT GTGTCGAGCA GTTTTTGGTT TAGCATTG                         48

(2) INFORMATION FOR SEQ ID NO:15:

(i) SEQUENCE CHARACTERISTICS:
                    (A) LENGTH: 8 amino acids
                    (B) TYPE: amino acid
                    (D) TOPOLOGY: linear (ii) MOLECULE TYPE: peptide (v) FRAGMENT TYPE: internal (xi) SEQUENCE DESCRIPTION: SEQ ID NO:15:

Thr Lys Asp Leu Thr Thr Tyr Gly
1               5

(2) INFORMATION FOR SEQ ID NO:16:

(i) SEQUENCE CHARACTERISTICS:
                    (A) LENGTH: 2220 base pairs
                    (B) TYPE: nucleic acid
                    (C) STRANDEDNESS: single
                    (D) TOPOLOGY: linear (ii) MOLECULE TYPE: cDNA (ix) FEATURE:
                    (A) NAME/KEY: CDS
                    (B) LOCATION: 1..2203

(xi) SEQUENCE DESCRIPTION: SEQ ID NO:16:

CGA CCA GCA GAC CAG ACA GTC ACA GCA GCC TTG ACA AAA CGT TCC TGG             48
Arg Pro Ala Asp Gln Thr Val Thr Ala Ala Leu Thr Lys Arg Ser Trp
1               5                   10                  15

```
AAC TCA AGC ACT TCT CCA CAG AGG AGG ACA GAG CAG ACA GCA GAG ACC      96
Asn Ser Ser Thr Ser Pro Gln Arg Arg Thr Glu Gln Thr Ala Glu Thr
            20                  25                  30

ATG GAG TCT CCC TCG GCC CCT CCC CAC AGA TGG TGC ATC CCC TGG CAG     144
Met Glu Ser Pro Ser Ala Pro Pro His Arg Trp Cys Ile Pro Trp Gln
        35                  40                  45

AGG CTC CTG CTC ACA GCC TCA CTT CTA ACC TTC TGG AAC CCG CCC ACC     192
Arg Leu Leu Leu Thr Ala Ser Leu Leu Thr Phe Trp Asn Pro Pro Thr
    50                  55                  60

ACT GCC AAG CTC ACT ATT GAA TCC ACG CCG TTC AAT GTC GCA GAG GGG     240
Thr Ala Lys Leu Thr Ile Glu Ser Thr Pro Phe Asn Val Ala Glu Gly
65                  70                  75                  80

AAG GAG GTG CTT CTA CTT GTC CAC AAT CTG CCC CAG CAT CTT TTT GGC     288
Lys Glu Val Leu Leu Leu Val His Asn Leu Pro Gln His Leu Phe Gly
                85                  90                  95

TAC AGC TGG TAC AAA GGT GAA AGA GTG GAT GGC AAC CGT CAA ATT ATA     336
Tyr Ser Trp Tyr Lys Gly Glu Arg Val Asp Gly Asn Arg Gln Ile Ile
            100                 105                 110

GGA TAT GTA ATA GGA ACT CAA CAA GCT ACC CCA GGG CCC GCA TAC AGT     384
Gly Tyr Val Ile Gly Thr Gln Gln Ala Thr Pro Gly Pro Ala Tyr Ser
        115                 120                 125

GGT CGA GAG ATA ATA TAC CCC AAT GCA TCC CTG CTG ATC CAG AAC ATC     432
Gly Arg Glu Ile Ile Tyr Pro Asn Ala Ser Leu Leu Ile Gln Asn Ile
    130                 135                 140

ATC CAG AAT GAC ACA GGA TTC TAC ACC CTA CAC GTC ATA AAG TCA GAT     480
Ile Gln Asn Asp Thr Gly Phe Tyr Thr Leu His Val Ile Lys Ser Asp
145                 150                 155                 160

CTT GTG AAT GAA GAA GCA ACT GGC CAG TTC CGG GTA TAC CCG GAG CTG     528
Leu Val Asn Glu Glu Ala Thr Gly Gln Phe Arg Val Tyr Pro Glu Leu
                165                 170                 175

CCC AAG CCC TCC ATC TCC AGC AAC AAC TCC AAA CCC GTG GAG GAC AAG     576
Pro Lys Pro Ser Ile Ser Ser Asn Asn Ser Lys Pro Val Glu Asp Lys
            180                 185                 190

GAT GCT GTG GCC TTC ACC TGT GAA CCT GAG ACT CAG GAC GCA ACC TAC     624
Asp Ala Val Ala Phe Thr Cys Glu Pro Glu Thr Gln Asp Ala Thr Tyr
        195                 200                 205

CTG TGG TGG GTA AAC AAT CAG AGC CTC CCG GTC AGT CCC AGG CTG CAG     672
Leu Trp Trp Val Asn Asn Gln Ser Leu Pro Val Ser Pro Arg Leu Gln
    210                 215                 220

CTG TCC AAT GGC AAC AGG ACC CTC ACT CTA TTC AAT GTC ACA AGA AAT     720
Leu Ser Asn Gly Asn Arg Thr Leu Thr Leu Phe Asn Val Thr Arg Asn
225                 230                 235                 240

GAC ACA GCA AGC TAC AAA TGT GAA ACC CAG AAC CCA GTG AGT GCC AGG     768
Asp Thr Ala Ser Tyr Lys Cys Glu Thr Gln Asn Pro Val Ser Ala Arg
                245                 250                 255

CGC AGT GAT TCA GTC ATC CTG AAT GTC CTC TAT GGC CCG GAT GCC CCC     816
Arg Ser Asp Ser Val Ile Leu Asn Val Leu Tyr Gly Pro Asp Ala Pro
            260                 265                 270

ACC ATT TCC CCT CTA AAC ACA TCT TAC AGA TCA GGG GAA AAT CTG AAC     864
Thr Ile Ser Pro Leu Asn Thr Ser Tyr Arg Ser Gly Glu Asn Leu Asn
        275                 280                 285

CTC TCC TGC CAT GCA GCC TCT AAC CCA CCT GCA CAG TAC TCT TGG TTT     912
Leu Ser Cys His Ala Ala Ser Asn Pro Pro Ala Gln Tyr Ser Trp Phe
    290                 295                 300

GTC AAT GGG ACT TTC CAG CAA TCC ACC CAA GAG CTC TTT ATC CCC AAC     960
Val Asn Gly Thr Phe Gln Gln Ser Thr Gln Glu Leu Phe Ile Pro Asn
305                 310                 315                 320

ATC ACT GTG AAT AAT AGT GGA TCC TAT ACG TGC CAA GCC CAT AAC TCA    1008
Ile Thr Val Asn Asn Ser Gly Ser Tyr Thr Cys Gln Ala His Asn Ser
                325                 330                 335
```

```
GAC ACT GGC CTC AAT AGG ACC ACA GTC ACG ACG ATC ACA GTC TAT GCA    1056
Asp Thr Gly Leu Asn Arg Thr Thr Val Thr Thr Ile Thr Val Tyr Ala
            340                 345                 350

GAG CCA CCC AAA CCC TTC ATC ACC AGC AAC AAC TCC AAC CCC GTG GAG    1104
Glu Pro Pro Lys Pro Phe Ile Thr Ser Asn Asn Ser Asn Pro Val Glu
            355                 360                 365

GAT GAG GAT GCT GTA GCC TTA ACC TGT GAA CCT GAG ATT CAG AAC ACA    1152
Asp Glu Asp Ala Val Ala Leu Thr Cys Glu Pro Glu Ile Gln Asn Thr
        370                 375                 380

ACC TAC CTG TGG TGG GTA AAT AAT CAG AGC CTC CCG GTC AGT CCC AGG    1200
Thr Tyr Leu Trp Trp Val Asn Asn Gln Ser Leu Pro Val Ser Pro Arg
385                 390                 395                 400

CTG CAG CTG TCC AAT GAC AAC AGG ACC CTC ACT CTA CTC AGT GTC ACA    1248
Leu Gln Leu Ser Asn Asp Asn Arg Thr Leu Thr Leu Leu Ser Val Thr
                405                 410                 415

AGG AAT GAT GTA GGA CCC TAT GAG TGT GGA ATC CAG AAC GAA TTA AGT    1296
Arg Asn Asp Val Gly Pro Tyr Glu Cys Gly Ile Gln Asn Glu Leu Ser
            420                 425                 430

GTT GAC CAC AGC GAC CCA GTC ATC CTG AAT GTC CTC TAT GGC CCA GAC    1344
Val Asp His Ser Asp Pro Val Ile Leu Asn Val Leu Tyr Gly Pro Asp
            435                 440                 445

GAC CCC ACC ATT TCC CCC TCA TAC ACC TAT TAC CGT CCA GGG GTG AAC    1392
Asp Pro Thr Ile Ser Pro Ser Tyr Thr Tyr Tyr Arg Pro Gly Val Asn
        450                 455                 460

CTC AGC CTC TCC TGC CAT GCA GCC TCT AAC CCA CCT GCA CAG TAT TCT    1440
Leu Ser Leu Ser Cys His Ala Ala Ser Asn Pro Pro Ala Gln Tyr Ser
465                 470                 475                 480

TGG CTG ATT GAT GGG AAC ATC CAG CAA CAC ACA CAA GAG CTC TTT ATC    1488
Trp Leu Ile Asp Gly Asn Ile Gln Gln His Thr Gln Glu Leu Phe Ile
                485                 490                 495

TCC AAC ATC ACT GAG AAG AAC AGC GGA CTC TAT ACC TGC CAG GCC AAT    1536
Ser Asn Ile Thr Glu Lys Asn Ser Gly Leu Tyr Thr Cys Gln Ala Asn
            500                 505                 510

AAC TCA GCC AGT GGC CAC AGC AGG ACT ACA GTC AAG ACA ATC ACA GTC    1584
Asn Ser Ala Ser Gly His Ser Arg Thr Thr Val Lys Thr Ile Thr Val
            515                 520                 525

TCT GCG GAG CTG CCC AAG CCC TCC ATC TCC AGC AAC AAC TCC AAA CCC    1632
Ser Ala Glu Leu Pro Lys Pro Ser Ile Ser Ser Asn Asn Ser Lys Pro
        530                 535                 540

GTG GAG GAC AAG GAT GCT GTG GCC TTC ACC TGT GAA CCT GAG GCT CAG    1680
Val Glu Asp Lys Asp Ala Val Ala Phe Thr Cys Glu Pro Glu Ala Gln
545                 550                 555                 560

AAC ACA ACC TAC CTG TGG TGG GTA AAT GGT CAG AGC CTC CCA GTC AGT    1728
Asn Thr Thr Tyr Leu Trp Trp Val Asn Gly Gln Ser Leu Pro Val Ser
                565                 570                 575

CCC AGG CTG CAG CTG TCC AAT GGC AAC AGG ACC CTC ACT CTA TTC AAT    1776
Pro Arg Leu Gln Leu Ser Asn Gly Asn Arg Thr Leu Thr Leu Phe Asn
            580                 585                 590

GTC ACA AGA AAT GAC GCA AGA GCC TAT GTA TGT GGA ATC CAG AAC TCA    1824
Val Thr Arg Asn Asp Ala Arg Ala Tyr Val Cys Gly Ile Gln Asn Ser
            595                 600                 605

GTG AGT GCA AAC CGC AGT GAC CCA GTC ACC CTG GAT GTC CTC TAT GGG    1872
Val Ser Ala Asn Arg Ser Asp Pro Val Thr Leu Asp Val Leu Tyr Gly
        610                 615                 620

CCG GAC ACC CCC ATC ATT TCC CCC CCA GAC TCG TCT TAC CTT TCG GGA    1920
Pro Asp Thr Pro Ile Ile Ser Pro Pro Asp Ser Ser Tyr Leu Ser Gly
625                 630                 635                 640

GCG AAC CTC AAC CTC TCC TGC CAC TCG GCC TCT AAC CCA TCC CCG CAG    1968
Ala Asn Leu Asn Leu Ser Cys His Ser Ala Ser Asn Pro Ser Pro Gln
```

```
          645                 650                    655
TAT TCT TGG CGT ATC AAT GGG ATA CCG CAG CAA CAC ACA CAA GTT CTC         2016
Tyr Ser Trp Arg Ile Asn Gly Ile Pro Gln Gln His Thr Gln Val Leu
                660                665             670

TTT ATC GCC AAA ATC ACG CCA AAT AAT AAC GGG ACC TAT GCC TGT TTT         2064
Phe Ile Ala Lys Ile Thr Pro Asn Asn Asn Gly Thr Tyr Ala Cys Phe
            675                 680              685

GTC TCT AAC TTG GCT ACT GGC CGC AAT AAT TCC ATA GTC AAG AGC ATC         2112
Val Ser Asn Leu Ala Thr Gly Arg Asn Asn Ser Ile Val Lys Ser Ile
        690                 695             700

ACA GTC TCT GCA TCT GGA ACT TCT CCT GGT CTC TCA GCT GGG GCC ACT         2160
Thr Val Ser Ala Ser Gly Thr Ser Pro Gly Leu Ser Ala Gly Ala Thr
705                 710                 715                 720

GTC GGC ATC ATG ATT GGA GTG CTG GTT GGG GTT GCT CTG ATA                 2202
Val Gly Ile Met Ile Gly Val Leu Val Gly Val Ala Leu Ile
                725                 730

TAGCAGCCCTGGTGTAGT                                                      2220
```

(2) INFORMATION FOR SEQ ID NO:17:

(i) SEQUENCE CHARACTERISTICS:
        (A) LENGTH: 734 amino acids
        (B) TYPE: amino acid
        (D) TOPOLOGY: linear (ii) MOLECULE TYPE: protein (xi) SEQUENCE DESCRIPTION: SEQ ID NO:17:

```
Arg Pro Ala Asp Gln Thr Val Thr Ala Ala Leu Thr Lys Arg Ser Trp
 1               5                  10                  15

Asn Ser Ser Thr Ser Pro Gln Arg Arg Thr Glu Gln Thr Ala Glu Thr
                20                  25                  30

Met Glu Ser Pro Ser Ala Pro Pro His Arg Trp Cys Ile Pro Trp Gln
            35                  40                  45

Arg Leu Leu Leu Thr Ala Ser Leu Leu Thr Phe Trp Asn Pro Pro Thr
        50                  55                  60

Thr Ala Lys Leu Thr Ile Glu Ser Thr Pro Phe Asn Val Ala Glu Gly
65                  70                  75                  80

Lys Glu Val Leu Leu Val His Asn Leu Pro Gln His Leu Phe Gly
                85                  90                  95

Tyr Ser Trp Tyr Lys Gly Glu Arg Val Asp Gly Asn Arg Gln Ile Ile
                100                 105                 110

Gly Tyr Val Ile Gly Thr Gln Gln Ala Thr Pro Gly Pro Ala Tyr Ser
            115                 120                 125

Gly Arg Glu Ile Ile Tyr Pro Asn Ala Ser Leu Leu Ile Gln Asn Ile
        130                 135                 140

Ile Gln Asn Asp Thr Gly Phe Tyr Thr Leu His Val Ile Lys Ser Asp
145                 150                 155                 160

Leu Val Asn Glu Glu Ala Thr Gly Gln Phe Arg Val Tyr Pro Glu Leu
                165                 170                 175

Pro Lys Pro Ser Ile Ser Ser Asn Asn Ser Lys Pro Val Glu Asp Lys
            180                 185                 190

Asp Ala Val Ala Phe Thr Cys Glu Pro Glu Thr Gln Asp Ala Thr Tyr
        195                 200                 205

Leu Trp Trp Val Asn Asn Gln Ser Leu Pro Val Ser Pro Arg Leu Gln
    210                 215                 220

Leu Ser Asn Gly Asn Arg Thr Leu Thr Leu Phe Asn Val Thr Arg Asn
```

-continued

```
            225                 230                 235                 240
    Asp Thr Ala Ser Tyr Lys Cys Glu Thr Gln Asn Pro Val Ser Ala Arg
                        245                 250                 255
    Arg Ser Asp Ser Val Ile Leu Asn Val Leu Tyr Gly Pro Asp Ala Pro
                    260                 265                 270
    Thr Ile Ser Pro Leu Asn Thr Ser Tyr Arg Ser Gly Glu Asn Leu Asn
                275                 280                 285
    Leu Ser Cys His Ala Ala Ser Asn Pro Pro Ala Gln Tyr Ser Trp Phe
            290                 295                 300
    Val Asn Gly Thr Phe Gln Gln Ser Thr Gln Glu Leu Phe Ile Pro Asn
    305                 310                 315                 320
    Ile Thr Val Asn Asn Ser Gly Ser Tyr Thr Cys Gln Ala His Asn Ser
                        325                 330                 335
    Asp Thr Gly Leu Asn Arg Thr Val Thr Ile Thr Val Tyr Ala
                    340                 345                 350
    Glu Pro Pro Lys Pro Phe Ile Thr Ser Asn Asn Ser Asn Pro Val Glu
                355                 360                 365
    Asp Glu Asp Ala Val Ala Leu Thr Cys Glu Pro Glu Ile Gln Asn Thr
            370                 375                 380
    Thr Tyr Leu Trp Trp Val Asn Asn Gln Ser Leu Pro Val Ser Pro Arg
    385                 390                 395                 400
    Leu Gln Leu Ser Asn Asp Asn Arg Thr Leu Thr Leu Leu Ser Val Thr
                        405                 410                 415
    Arg Asn Asp Val Gly Pro Tyr Glu Cys Gly Ile Gln Asn Glu Leu Ser
                    420                 425                 430
    Val Asp His Ser Asp Pro Val Ile Leu Asn Val Leu Tyr Gly Pro Asp
                435                 440                 445
    Asp Pro Thr Ile Ser Pro Ser Tyr Thr Tyr Arg Pro Gly Val Asn
            450                 455                 460
    Leu Ser Leu Ser Cys His Ala Ala Ser Asn Pro Pro Ala Gln Tyr Ser
    465                 470                 475                 480
    Trp Leu Ile Asp Gly Asn Ile Gln Gln His Thr Gln Glu Leu Phe Ile
                        485                 490                 495
    Ser Asn Ile Thr Glu Lys Asn Ser Gly Leu Tyr Thr Cys Gln Ala Asn
                    500                 505                 510
    Asn Ser Ala Ser Gly His Ser Arg Thr Thr Val Lys Thr Ile Thr Val
                515                 520                 525
    Ser Ala Glu Leu Pro Lys Pro Ser Ile Ser Ser Asn Asn Ser Lys Pro
            530                 535                 540
    Val Glu Asp Lys Asp Ala Val Ala Phe Thr Cys Glu Pro Glu Ala Gln
    545                 550                 555                 560
    Asn Thr Thr Tyr Leu Trp Trp Val Asn Gly Gln Ser Leu Pro Val Ser
                        565                 570                 575
    Pro Arg Leu Gln Leu Ser Asn Gly Asn Arg Thr Leu Thr Leu Phe Asn
                    580                 585                 590
    Val Thr Arg Asn Asp Ala Arg Ala Tyr Val Cys Gly Ile Gln Asn Ser
                595                 600                 605
    Val Ser Ala Asn Arg Ser Asp Pro Val Thr Leu Asp Val Leu Tyr Gly
            610                 615                 620
    Pro Asp Thr Pro Ile Ile Ser Pro Pro Asp Ser Ser Tyr Leu Ser Gly
    625                 630                 635                 640
    Ala Asn Leu Asn Leu Ser Cys His Ser Ala Ser Asn Pro Ser Pro Gln
                        645                 650                 655
```

```
Tyr Ser Trp Arg Ile Asn Gly Ile Pro Gln Gln His Thr Gln Val Leu
            660                 665                 670

Phe Ile Ala Lys Ile Thr Pro Asn Asn Asn Gly Thr Tyr Ala Cys Phe
        675                 680                 685

Val Ser Asn Leu Ala Thr Gly Arg Asn Asn Ser Ile Val Lys Ser Ile
    690                 695                 700

Thr Val Ser Ala Ser Gly Thr Ser Pro Gly Leu Ser Ala Gly Ala Thr
705                 710                 715                 720

Val Gly Ile Met Ile Gly Val Leu Val Gly Val Ala Leu Ile
                725                 730
```

(2) INFORMATION FOR SEQ ID NO:18:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CCAGTGAATT CCTAATACGA CTACCTATAG GTTAAAACAG C                    41

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GATGAACCCT CGAGACCCAT TATG                                    24

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CCACCAAGTA CGTAACCACA TATGG                              25

(2) INFORMATION FOR SEQ ID NO:21:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GTGAGGACTG CTGG                                                14

(2) INFORMATION FOR SEQ ID NO:22:

```
     (i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:22:

CACCACTGCC CTCGAGAAGC TCACTATTG                                              29

(2) INFORMATION FOR SEQ ID NO:23:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:23:

CACCACTGCC CTCGAGAAGC TCACTATTG                                              29
```